United States Patent [19]
Maddon et al.

[11] Patent Number: 6,034,223
[45] Date of Patent: Mar. 7, 2000

[54] NON-PEPTIDYL MOIETY-CONJUGATED CD4-GAMMA2 AND CD4-IGG2 IMMUNOCONJUGATES, AND USES THEREOF

[75] Inventors: Paul J. Maddon, New York; Graham P. Allaway, Mohegan Lake, both of N.Y.

[73] Assignee: Progenics Pharmaceuticals, Inc., Tarrytown, N.Y.

[21] Appl. No.: 08/477,460

[22] Filed: Jun. 7, 1995

Related U.S. Application Data

[63] Continuation-in-part of application No. 08/379,516, filed as application No. PCT/US93/07422, Aug. 6, 1993, which is a continuation-in-part of application No. 07/927,931, Aug. 7, 1992, abandoned.

[51] Int. Cl.[7] ............................. C07K 16/00; C12P 21/04
[52] U.S. Cl. ................. 530/391.7; 435/69.7; 530/388.35
[58] Field of Search ...................... 435/69.7; 530/388.35, 530/391.7

[56] References Cited

FOREIGN PATENT DOCUMENTS

WO8801304  2/1988  WIPO .
WO8902922  4/1989  WIPO .

OTHER PUBLICATIONS

Fahey et al., Status of immune–based therapies in HIV infection and AIDS Clin. Exp. Immunol. (1992) 88, 1–5 Jan. 1992.

Fox, J.L., No winners against AIDS, Bio/Technology, (1994) vol. 12, Feb. p. 128 1994.

Ashorn, P., et al.,Elimination Of Infectious Human Immunodeficiency Virus From Human T–Cell Cultures By Synergistic Action Of CD4–Pseudomonas Exotoxin And Reverse Transcriptase Inhibitors, Proc. Nat'l. Acad. Sci. USA 87:8889–8893 (1990).

Aullo, P., et al., A Recombinant Diptheria Toxin Related Human CD4 Fusion Protein Specifically Kills HIV Infected Cells Which Express gp120 But Selects Fusion Toxin Resistant Cells Which Carry HIV, EMBO Journal 11, No. 11(2):575–583 (1992).

Byrn, R.A., et al., Biological Properties Of A CD4 Immunoadhesin, Nature 344:667–670 (1990).

Capon, D.J., et al., Designing CD4 Immunoadhesins for AIDS Therapy, Nature 337:525–531 (1989) (Exhibit B).

Chaudhary, V.K., et al., Selective Killing Of HIV–Infected Cells By Recombinant Human CD4–Pseudomonas Exotoxin Hybrid Protein, Nature 335:369–372 (1988).

(List continued on next page.)

*Primary Examiner*—Ponnathapura Achutamurthy
*Assistant Examiner*—Hankyel T. Park
*Attorney, Agent, or Firm*—John P. White; Cooper & Dunham LLP

[57] ABSTRACT

This invention provides an immunoconjugate which comprises 1) a non-peptidyl toxin and 2) a CD4-gamma2 chimeric heavy chain homodimer linked thereto. This invention also provides an immunoconjugate which comprises 1) a gamma radiation-emitting radionuclide of low to moderate cytotoxicity and 2) a CD4-gamma2 chimeric heavy chain homodimer linked thereto. This invention further provides an immunoconjugate which comprises 1) a non-peptidyl toxin and 2) a heterotetramer comprising two heavy chains and two light chains, both heavy chains being either a) IgG2 heavy chains or b) chimeric CD4-IgG2 heavy chains, and both light chains being either a) kappa light chains or b) chimeric CD4-kappa light chains. This invention further provides an immunoconjugate which comprises 1) a gamma radiation- emitting radionuclide of low to moderate cytotoxicity and 2) a heterotetramer comprising two heavy chains and two light chains, both heavy chains being either a) IgG2 heavy chains or b) chimeric CD4-IgG2 heavy chains, and both light chains being either a) kappa light chains or b) chimeric CD4 kappa light chains. Finally, this invention provides methods of using the immunoconjugates of the subject invention.

8 Claims, 26 Drawing Sheets

OTHER PUBLICATIONS

Gartner, S. et al., The Role of Mononuclear Phagocytes in HTLV–III/LAV Infection, Science 233:215–219 (1986) (Exhibit C).

Houghton, A.N. and Scheinberg, D.A., Monoclonal Antibodies: Potential Applications to the Treatment of Cancer, Seminars in Oncology, 13(2):165–178 (1986) (Exhibit D).

Jarman, M., A Radical Approach To Cancer, Nature 349:566–567 (1991).

Lasky, L.A., et al., Delineation Of A Region Of The Human Immunodeficiency Virus Type 1 gp120 Glycoprotein Critical For Interaction With The CD4 Receptor, Cell 50:975–985 (1987).

Moore, J.P., et al., Dissociation of gp120 From HIV–1 Virions Induced By Soluble CD4, Science 250:1139–1142 (1990).

Morrison, S.L., et al., Chimeric Human Antibody Molecules: Mouse Antigen–Binding Domains With Human Constant Region Domains, Proc. Natl. Acad. Sci. USA 81:6851–6855 (1984).

Nicolaou, K.C., et al., Designed Enediynes: A New Class Of DNA–Cleaving Molecules With Potent And Selective Anticancer Activity, Science 256:1172–1178 (1992).

Pound, J.D. and Walker M.R., Membrane Fc Receptors For IgG Subclasses, in The Human IgG Subclasses: Molecular Analysis Of Structure, Function and Regulation, Pergamon Press, Oxford, U.K. 111–133 (1990).

Schooley, R.T., et al., Recombinant Soluble CD4 Therapy In Patients With The Acquired Immunodeficiency Syndrome (AIDS) And AIDS–Related Complex, Ann. Internal Med. 112:247–253 (1990).

Till, M.A., et al., HIV–Infected Cells Are Killed By rCD4–Ricin A Chain, Science 242:1166–1168 (1988).

Traunecker, A., et al., Highly Efficient Neutralization Of HIV With Recombinant CD4–Immunoglobulin Molecules, Nature 339:68–70 (1989).

Magerstadt, M., et al., Antibody Conjugates and Malignant Disease, CRC Press, Boca Raton, FL. (1991).

FIG. 3A

```
CAAGCCCAGAGCCCTGCCATTTCTGTGGGCTCAGGTCCCCTACTGCTCAGCCCCTT                                55
              →CD4           -20
              M   N   R   G   V   P   F   R   H
CCTCCCTCGGCAAGGCCACAATG AAC CGG GGA GTC CCT TTT AGG CAC          102
        -10
 L   L   L   V   L   Q   L   A   L   L   P   A   A   T
TTG CTT CTG GTG CTG CAA CTG GCG CTC CTC CCA GCA GCC ACT         144
                                            +10
 -1  +1                                      G   D   T   V
 Q   G   K   K   V   V   L   G   K   K   K
CAG GGA AAG AAA GTG GTG CTG GGC AAA AAA AAA GGG GAT ACA GTG     186
                        +20
 E   L   T   C   T   A   S   Q   K   K   S   I   Q   F
GAA CTG ACC TGT ACA GCT TCC CAG AAG AAG AGC ATA CAA TTC         228
                                                    +40
         +30                                         Q
 H   W   K   N   S   N   Q   I   K   I   L   G   N   R
CAC TGG AAA AAC TCC AAC CAG ATA AAG ATT CTG GGA AAT CAG         270
                                    +50
 G   S   F   L   T   K   G   P   S   K   L   N   D   R
GGC TCC TTC TTA ACT AAA GGT CCA TCC AAG CTG AAT GAT CGC         312
```

FIG. 3B

```
  G   S   F   L   T   K   G   P   S   K   L   N   D   R
GGC TCC TTC TTA ACT AAA GGT CCA TCC AAG CTG AAT GAT CGC   312
                        +60

A   D   S   R   R   S   L   W   D   Q   G   N   F   P
GCT GAC TCA AGA AGA AGC CTT TGG GAC CAA GGA AAC TTC CCC   354
        +70                                     +80

L   I   I   K   N   L   K   I   E   D   S   D   T   Y
CTG ATC ATC AAG AAT CTT AAG ATA GAA GAC TCA GAT ACT TAC   396
                                +90

I   C   E   V   E   D   Q   K   E   E   V   Q   L   L
ATC TGT GAA GTG GAG GAC CAG AAG GAG GAG GTG CAA TTG CTA   438
                        +100                       +110

V   F   G   L   T   A   N   S   D   T   H   L   Q
GTG TTC GGA TTG ACT GCC AAC TCT GAC ACC CAC CTG CTT CAG   480

G   Q   S   L   T   L   T   L   E   S   P   P   G   S
GGG CAG AGC CTG ACC CTG ACC TTG GAG AGC CCC CCT GGT AGT   522
                                        +120

S   P   S   V   Q   C   R   S   P   R   G   K   N   I
AGC CCC TCA GTG CAA TGT AGG AGT CCA AGG GGT AAA AAC ATA   564
                +130
```

FIG. 3C

```
    +140                                    +150
 Q   G    G    K    T    L    S    V    S    Q    L    E    L    Q
CAG GGG  GGG  AAG  ACC  CTC  TCC  GTG  TCT  CAG  CTG  GAG  CTC  CAG      606
                                  +160
 D   S    G    T    W    T    C    T    V    L    Q    N    Q    K
GAT AGT  GGC  ACC  TGG  ACA  TGC  ACT  GTC  TTG  CAG  AAC  CAG  AAG      648
                                                              ⌐→Hinge
               +170                                         +180
 K   V    E    F    K    I    D    I    V    V    L    A    F    E
AAG GTG  GAG  TTC  AAA  ATA  GAC  ATC  GTG  GTG  CTA  GCT  TTC  GAG      690
                                        +190
 R   K    C    C    V    E    C    P    P    C    P
CGC AAA  TGT  TGT  GTC  GAG  TGC  CCA  CCG  TGC  CCAGGTAAGCCAGCC         705

CAGGCCCTCGCCCCTCCAGCTTCAAGGCGGGACAGGTGCCCCTAGAGTAGCCTGCATCC              760
                                                         ⌐→CH2
                                                        A
AGGGACAGGCCCCAGCTGGGTGCTGACACGTCCACCTCCATCTCTTCCTCAGCA                   814
                         +200
 P   P    V    A    G    P    S    V    F    L    F    P    P    K
CCA CCT  GTG  GCA  GGA  CCG  TCA  GTC  TTC  CTC  TTC  CCC  CCA  AAA      856
```

FIG. 3D

```
        +210
    P   K   D   T   L   M   I   S   R   T   P   E   V   T
    CCC AAG GAC ACC CTC ATG ATC TCC CGG ACC CCT GAG GTC ACG    898
+220                                        +230
    C   V   V   D   V   S   H   E   D   P   E   V   Q
    TGC GTG GTG GAC GTG AGC CAC GAA GAC CCC GAG GTC CAG        940
                            +240
    F   N   W   Y   V   D   G   V   E   V   H   N   A   K
    TTC AAC TGG TAC GTG GAC GGC GTG GAG GTG CAT AAT GCC AAG    982
            +250                                    +260
    T   K   P   R   E   E   Q   F   N   S   T   F   R   V
    ACA AAG CCA CGG GAG GAG CAG TTC AAC AGC ACG TTC CGT GTG   1024
                                    +270
    V   S   V   L   T   V   V   H   Q   D   W   L   N   G
    GTC AGC GTC CTC ACC GTT GTG CAC CAG GAC TGG CTG AAC GGC   1066
                    +280
    K   E   Y   K   C   K   V   S   N   K   G   L   P   A
    AAG GAG TAC AAG TGC AAG GTC TCC AAC AAA GGC CTC CCA GCC   1108
+290
    P   I   E   K   T   I   S   K   T   K
    CCC ATC GAG AAA ACC ATC TCC AAA ACC AAA AAGGTGGGACCCCGGGGG 1154
```

FIG. 3E

```
TATGAGGGCCACATGGACAGAGGGCCGGCTCGGGCCCACCCTCTGCCCTGGGAGTGA          1209
                                  ┌→CH3
                                 +300
                                  G  Q  P  R  E  P  Q
CCGCTGTGCCAACCTCTGTCCCTACAGGG CAG CCC CGA GAA CCA CAG              1256
                                                        +320
 V  Y  T  L  P  P  S  R  E  E  M  T  K  N
GTG TAC ACC CTG CCC CCA TCC CGG GAG GAG ATG ACC AAG AAC            1298
                            +330
 Q  V  S  L  T  C  L  V  K  G  F  Y  P  S
CAG GTC AGC CTG ACC TGC CTG GTC AAA GGC TTC TAC CCC AGC            1340
             +340                               +360
 D  I  A  V  E  W  E  S  N  G  Q  P  E  N
GAC ATC GCC GTG GAG TGG GAG AGC AAT GGG CAG CCG GAG AAC            1382
      +350                                      +360
 N  Y  K  T  T  P  P  M  L  D  S  D  G  S
AAC TAC AAG ACC ACA CCT CCC ATG CTG GAC TCC GAC GGC TCC            1424
                             +370
 F  F  L  Y  S  K  L  T  V  D  K  S  R  W
TTC TTC CTC TAC AGC AAG CTC ACC GTG GAC AAG AGC AGG TGG            1466
```

FIG. 3F

```
     +380                                    +400
  Q   Q   G   N   V   F   S   C   S   V   M   H   E   A
 CAG CAG GGG AAC GTC TTC TCA TGC TCC GTG ATG CAT GAG GCT   1508

+410
  L   H   N   H   Y   T   Q   K   S   L   S   L   S   P
 CTG CAC AAC CAC TAC ACG CAG AAG AGC CTC TCC CTG TCT CCG   1550

G   K  stop
 GGT AAA TGAGTGCCACGGCCGGCAAGCCCCGCTCCCCAGGCTCTCGGGGTCG   1603

CGTGAGGATGCTTGGCACGTACCCCCGTGTACATACTTCCCAGGCACCCAGTGG   1658

AAATAAAGCACCCCAGCGTGCCCTGGGCCCCTGCGAGACTGTGATGGTTCTTTCC  1713

GTGGGTCAGGCCCGAGTCTGAGGCCTGAGTGGCATGAGGGAGGCAGAGTGGGTC...  1766
```

FIG. 4A

```
CAAGCCCAGAGCCCTGCCATTTCTGTGGGCTCAGGTCCCTACTGCTCAGCCCCTT        55
         └─►CD4
                         -20
            M   N   R   G   V   P   F   R   H
CCTCCCTCGGCAAGGCCACAATG AAC CGG GGA GTC CCT TTT AGG CAC       102

-10                              +10
    L   L   V   L   Q   L   A   L   L   P   A   A   T
    TTG CTT GTG CTG CAA CTG GCG CTC CTC CCA GCA GCC ACT       144

-1  +1
    Q   G   K   K   V   V   L   G   K   K   G   D   T   V
    CAG GGA AAG AAA GTG GTG CTG GGC AAA AAA GGG GAT ACA GTG   186

+20
    E   L   T   C   T   A   S   Q   K   K   S   I   Q   F
    GAA CTG ACC TGT ACA GCT TCA CAG AAG AAG AGC ATA CAA TTC   228

+30                                       +40
    H   W   K   N   S   N   Q   I   K   I   L   G   N   Q
    CAC TGG AAA AAC TCC AAC CAG ATA AAG ATT CTG GGA AAT CAG   270

+50
    G   S   F   L   T   K   G   P   S   K   L   N   D   R
    GGC TCC TTC TTA ACT AAA GGT CCA TCC AAG CTG AAT GAT CGC   312
```

FIG. 4B

```
 A   D   S   R   R   S   L   W   D   Q   G   N   F   P
                    +60
GCT GAC TCA AGA AGA AGC CTT TGG GAC CAA GGA AAC TTC CCC    354

L   I   I   K   N   L   K   I   E   D   S   D   T   Y
        +70                              +80
CTG ATC ATC AAG AAT CTT AAG ATA GAA GAC TCA GAT ACT TAC    396

I   C   E   V   E   D   Q   K   E   E   V   Q   L   L
                            +90
ATC TGT GAA GTG GAG GAC CAG AAG GAG GAG GTG CAA TTG CTA    438

V   F   G   L   T   A   N   S   D   T   H   L   L   Q
            +100                                +110
GTG TTC GGA TTG ACT GCC AAC TCT GAC ACC CAC CTG CTT CAG    480

G   Q   S   L   T   L   E   S   P   P   G   S
                            +120
GGG CAG AGC CTG ACC TTG GAG AGC CCC CCT GGT AGT            522

S   P   V   Q   C   R   S   P   R   G   K   N   I
            +130
AGC CCC TCA GTG CAA TGT AGG AGT CCA AGG GGT AAA AAC ATA    564
```

FIG. 4C

```
      +140
      Q     G     G     K     T     L     S     V     S     Q     L     Q              606
      CAG   GGG   GGG   AAG   ACC   CTC   TCC   GTG   TCT   CAG   CTG   CAG
                                          +150
                                          E                       L     Q

D     S     G     T     W     T     C     T     V     L     Q     N     Q     K  648
      GAT   AGT   GGC   ACC   TGG   ACA   TGC   ACT   GTC   TTG   CAG   AAC   CAG   AAG
                              +160                                                  →CH1
                                                                                   +180
      K     V     E     F     K     I     D     I     V     V     L     A     F     A  690
      AAG   GTG   GAG   TTC   AAA   ATA   GAC   ATC   GTG   GTG   CTA   GCT   TTC   GCC
                        +170                                +190

S     T     K     G     P     S     V     F     P     L     A     P     C     S  732
      TCC   ACC   AAG   GGC   CCA   TCG   GTC   TTC   CCC   CTG   GCG   CCC   TGC   TCC

R     S     T     S     E     S     T     A     A     L     G     C     L     V  774
      AGG   AGC   ACC   TCC   GAG   AGC   ACA   GCC   GCC   CTG   GGC   TGC   CTG   GTC
                              +200                                      +220

K     D     Y     F     P     E     P     V     T     V     S     W     N     S  816
      AAG   GAC   TAC   TTC   CCC   GAA   CCG   GTG   ACG   GTG   TCG   TGG   AAC   TCA
      +210                                            +230

G     A     L     T     S     G     V     H     T     F     P     A     V     L  858
      GGC   GCT   CTG   ACC   AGC   GGC   GTG   CAC   ACC   TTC   CCA   GCT   GTC   CTA
```

FIG. 4D

```
      +240                              +250
  Q   S   S   G   L   Y   S   L   S   V   V   T   V
CAG TCC TCA GGA CTC TAC TCC CTC AGC AGC GTG GTG ACC GTG    900

+260
  P   S   S   N   F   G   T   Q   T   Y   T   C   N   V
CCC TCC AGC AAC TTC GGC ACC CAG ACC TAC ACC TGC AAC GTA    942

+270
  D   H   K   P   S   N   T   K   V   D   K   T   V
GAT CAC AAG CCC AGC AAC ACC AAG GTG GAC AAG ACA GTTGGTG    985

AGAGGCCAGTCTCAGGGAGGGTGTCTGCTGGAAGCCAGGCTCAGCCCTCCTG      1040

CCTGGACGCACCCCGGCTGTGCAGCCCCAGGGCCAAGGCAGCAGCCCCCAT       1095

CTGTCTCCTCACCCGGAGGCCCTGCCCGCCCCACTCATGCTCAGGGAGAGGGTC    1150

TTCTGGCTTTTCCACCAGGCTCCAGGCACAGGCTGGGTGCCCCCTACCCCA       1205

GGCCCTTCACACAGGGGCAGGTGCTTGGCTCAGACCTGCCAAAAGCCATATCC     1260
```

FIG. 4E

```
GGGAGGACCCTGCCCCTGACCTAAGCCGACCCCAAAGGCCAAACTGTCCACTCCC                     1315

TCAGCTCGGACACCTTCTCTCCTCCCAGATCCGAGTAACTCCCAATCTTCTCTCT                     1370
    →Hinge
       +280
    E    R    K    C    C    V    E    C    P    P    C    P
GCAGAG CGC AAA TGT TGT GTC GAG TGC CCA CCG TGC CCAGTAAG            1415

CCAGCCCCAGGCCTCGCCCCTCCAGCTCAAGGCGGGACACAGGTGCCCTAGAGTAGCCT                 1470

GCATCCAGGGACAGGCCCCAGCTGGGTGCTGACACGTCCACCTCCATCTCTTCCT                     1525
  →CH2                                            +300
 +290                                   F    L    F    P    P
  A    P    P    V    A    G    P    S    V    F    L    F    P    P
CAGCA CCA CCT GTG GCA GGA CCG TCA GTC TTC CTC TTC CCC CCA                    1569

+310
  K    P    K    D    T    L    M    I    S    R    T    P    E    V
AAA CCC AAG GAC ACC CTC ATG ATC TCC CGG ACC CCT GAG GTC                     1611

+320                                 +330
  T    C    V    V    V    D    V    S    H    E    D    P    E    V
ACG TGC GTG GTG GTG GAC GTG AGC CAC GAA GAC CCC GAG GTC                     1653
```

FIG. 4F

```
      Q   F   N   W   Y   V   D   G   V   E   V   H   N   A
     CAG TTC AAC TGG TAC GTG GAC GGC GTG GAG GTG CAT AAT GCC         1695
                     +350
      K   T   K   P   R   E   E   Q   F   N   S   T   F   R
     AAG ACA AAG CCA CGG GAG GAG CAG TTC AAC AGC ACG TTC CGT         1737
     +360                                        +370
      V   V   S   V   L   T   V   V   H   Q   D   W   L   N
     GTG GTC AGC GTC CTC ACC GTT GTG CAC CAG GAC TGG CTG AAC         1779
                                 +380
      G   K   E   Y   K   C   K   V   S   N   K   G   L   P
     GGC AAG GAG TAC AAG TGC AAG GTC TCC AAC AAA GGC CTC CCA         1821
              +390
      A   P   I   E   K   T   I   S   K   T   K
     GCC CCC ATC GAG AAA ACC ATC TCC AAA ACC AAA GGTGGGACCCGC        1866

GGGGTATGAGGGCCACATGGACAGAGGCCGGCTCGG CCCCACCCTCTGCCCTGGGA       1921
                                         ┌─►CH3
                                         │  +400
                                         G   Q   P   R   E   P   Q
     GTGACCGCTGTGCCAACCTCTGTCCCTACAGGG CAG CCC CGA GAA CCA CAG       1972
```

FIG. 4G

```
     V   Y   T   L   P   P   S   R   E   E   M   T   K   N
    GTG TAC ACC CTG CCC CCA TCC CGG GAG GAG ATG ACC AAG AAC    2014
        +410
    +420
     Q   V   S   L   T   C   L   V   K   G   F   Y   P   S
    CAG GTC AGC CTG ACC TGC CTG GTC AAA GGC TTC TAC CCC AGC    2056
                            +430
     D   I   A   V   E   W   E   S   N   G   Q   P   E   N
    GAC ATC GCC GTG GAG TGG GAG AGC AAT GGG CAG CCG GAG AAC    2098
                    +440
         +450                                    +460
     N   Y   K   T   T   P   P   M   L   D   S   D   G   S
    AAC TAC AAG ACC ACA CCT CCC ATG CTG GAC TCC GAC GGC TCC    2140
                                        +470
     F   F   L   Y   S   K   L   T   V   D   K   S   R   W
    TTC TTC CTC TAC AGC AAG CTC ACC GTG GAC AAG AGC AGG TGG    2182
            +480
     Q   Q   G   N   V   F   S   C   S   V   M   H   E   A
    CAG CAG GGG AAC GTC TTC TCA TGC TCC GTG ATG CAT GAG GCT    2224
        +490                                +500
     L   H   N   H   Y   T   Q   K   S   L   S   L   S   P
    CTG CAC AAC CAC TAC ACG CAG AAG AGC CTC TCC CTG TCT CCG    2266
```

FIG. 4H

```
  G   K  stop
GGT AAA TGAGTGCCACGGCCGGCAAGCCCCGCTCCCCAGGCTCTCGGGGTCG    2319

CGTGAGGATGCTTGGCACGTACCCCGTGTACATACTTCCCAGGCACCCAGCATGG    2374

AAATAAAGCACCCAGCGCTGCCCTGGGCCCCCTGCCGAGACTGTGATGGTTCTTTCC    2429

GTGGGTCAGGCCCGAGTCTGAGGCCTGAGTGGCATGAGGGAGGCAGAGTGGGTC...   2482
```

FIG. 5A

```
CAAGCCCAGAGCCCTGCCATTTCTGTGGGCTCAGGTCCCTACTGCTCAGCCCCTT                      55
                     →CD4
                                        -20
             M   N   R   G   V   P   F   R   H
CCTCCCTCGGCAAGGCCACAATG AAC CGG GGA GTC CCT TTT AGG CAC                      102

-10
 L   L   V   L   Q   L   A   L   L   P   A   A   T
TTG CTT CTG GTG CTG CAA CTG GCG CTC CTC CCA GCA GCC ACT                      144
  -1  +1                                            +10
 Q   G   K   K   V   V   L   G   K   K   G   D   T   V
CAG GGA AAG AAG GTG GTG CTG GGC AAA AAA GGG GAT ACA GTG                      186

+20
 E   L   T   C   T   A   S   Q   K   K   S   I   Q   F
GAA CTG ACC TGT ACA GCT TCC CAG AAG AAG AGC ATA CAA TTC                      228

+40
 H   W   K   N   S   N   Q   I   K   I   L   G   N   Q
CAC TGG AAA AAC TCC AAC CAG ATA AAG ATT CTG GGA AAT CAG                      270

+50
 G   S   F   L   T   K   G   P   S   K   L   N   D   R
GGC TCC TTC TTA ACT AAA GGT CCA TCC AAG CTG AAT GAT CGC                      312
```

FIG. 5B

```
     A   D   S   R   R   S   L   W   D   Q   G   N   F   P
    GCT GAC TCA AGA AGA AGC CTT TGG GAC CAA GGA AAC TTC CCC    354
                        +60
         +70                                +80
     L   I   I   K   N   L   K   I   E   D   S   D   T   Y
    CTG ATC ATC AAG AAT CTT AAG ATA GAA GAC TCA GAT ACT TAC    396

+90
     I   C   E   V   E   D   Q   K   E   E   V   Q   L   L
    ATC TGT GAA GTG GAG GAC CAG AAG GAG GAG GTG CAA TTG CTA    438

+100                                     +110
     V   F   G   S   L   T   A   N   S   D   T   H   L   Q
    GTG TTC GGA AGC CTG ACT GCC AAC TCT GAC ACC CAC CTT CAG    480

+120
     G   Q   S   L   T   L   T   L   E   S   P   P   G   S
    GGG CAG AGC CTG ACC CTG ACC TTG GAG AGC CCC CCT GGT AGT    522

+130
     S   P   S   V   Q   C   R   S   P   R   G   K   N   I
    AGC CCC TCA GTG CAA TGT AGG AGT CCA AGG GGT AAA AAC ATA    564
```

FIG. 5C

```
      +140
      Q    G    G    K    T    L    S    V    S    Q    L    E    L    Q
      CAG  GGG  GGG  AAG  ACC  CTC  TCC  GTG  TCT  CAG  CTG  GAG  CTC  CAG    606
                                          +150

D    S    G    T    W    T    C    T    V    L    Q    N    Q    K
      GAT  AGT  GGC  ACC  TGG  ACA  TGC  ACT  GTC  TTG  CAG  AAC  CAG  AAG    648
                     +160                                            →Ckappa
                                                                     +180
      K    V    E    F    K    I    D    I    V    V    L    A    F    T
      AAG  GTG  GAG  TTC  AAA  ATA  GAC  ATC  GTG  GTG  CTA  GCT  TTC  ACT    690
                +170

V    A    A    P    S    V    F    I    F    P    P    S    D    E
      GTG  GCT  GCA  CCA  TCT  GTC  TTC  ATC  TTC  CCG  CCA  TCT  GAT  GAG    732
                                                    +190

Q    L    K    S    G    T    A    S    V    V    C    L    L    N
      CAG  TTG  AAA  TCT  GGA  ACT  GCC  TCT  GTT  GTG  TGC  CTG  CTG  AAT    774
                               +200

N    F    Y    P    R    E    A    K    V    Q    W    K    V    D
      AAC  TTC  TAT  CCC  AGA  GAG  GCC  AAA  GTA  CAG  TGG  AAG  GTG  GAT    716
           +210                                            +220

N    A    L    Q    S    G    N    S    Q    E    S    V    T    E
      AAC  GCC  CTC  CAA  TCG  GGT  AAC  TCC  CAG  GAG  AGT  GTC  ACA  GAG    758
                                     +230
```

FIG. 5D

```
      +240
  Q   D   S   K   D   S   T   Y   S   L   S   S   T   L
CAG GAC AGC AAG GAC AGC ACC TAC AGC CTC AGC AGC ACC CTG    900
                              +260
  T   L   S   K   A   D   Y   E   K   H   K   V   Y   A
ACG CTG AGC AAA GCA GAC TAC GAG AAA CAC AAA GTC TAC GCC    942
                  +270
  C   E   V   T   H   Q   G   L   S   S   P   V   T   K
TGC GAA GTC ACC CAT CAG GGC CTG AGC TCG CCC GTC ACA AAG    984
  +280
  S   F   N   R   G   E   C  stop
AGC TTC AAC AGG GGA GAG TGT TAG AGGGAGAAGTGCCCCACCTGCTC   1032

CTCAGTTCCAGCCCTGACCCCTTTGGCCCTCTGACCCTTTTCCACAGG         1088

GGACCCTACCCCCTATTGCGGTCCTCCAAGCTCATCTTTCACCTCACCCCCTCCTCC 1144

TCCTT
```

CD4IgG$_2$ chimeric heterotetramer (H$_2$L$_2$)

CD4IgG$_2$ chimeric homodimer (H$_2$L$_2$)

CD4IgG$_2$ chimeric heavy chains

CD4kappa chimeric light chains

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 1796 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: Homo sapiens
        (G) CELL TYPE: Lymphocyte (xi) SEQUENCE DESCRIPTION: SEQ ID NO:1:

```
CAAGCCCAGA GCCCTGCCAT TTCTGTGGGC TCAGGTCCCT ACTGCTCAGC CCCTTCCTCC      60

CTCGGCAAGG CCACAATGAA CCGGGGAGTC CCTTTTAGGC ACTTGCTTCT GGTGCTGCAA     120

CTGGCGCTCC TCCCAGCAGC CACTCAGGGA AGAAAGTGG TGCTGGGCAA AAAAGGGGAT     180

ACAGTGGAAC TGACCTGTAC AGCTTCCCAG AAGAAGAGCA TACAATTCCA CTGGAAAAAC     240

TCCAACCAGA TAAAGATTCT GGGAAATCAG GGCTCCTTCT TAACTAAAGG TCCATCCAAG     300

CTGAATGATC GCGCTGACTC AAGAAGAAGC CTTTGGGACC AAGGAAACTT CCCCCTGATC     360

ATCAAGAATC TTAAGATAGA AGACTCAGAT ACTTACATCT GTGAAGTGGA GGACCAGAAG     420

GAGGAGGTGC AATTGCTAGT GTTCGGATTG ACTGCCAACT CTGACACCCA CCTGCTTCAG     480

GGGCAGAGCC TGACCCTGAC CTTGGAGAGC CCCCCTGGTA GTAGCCCCTC AGTGCAATGT     540

AGGAGTCCAA GGGGTAAAAA CATACAGGGG GGAAGACCC TCTCCGTGTC TCAGCTGGAG     600

CTCCAGGATA GTGGCACCTG GACATGCACT GTCTTGCAGA ACCAGAAGAA GGTGGAGTTC     660

AAAATAGACA TCGTGGTGCT AGCTTTCGAG CGCAAATGTT GTGTCGAGTG CCCACCGTGC     720

CCAGGTAAGC CAGCCCAGGC CTCGCCCTCC AGCTCAAGGC GGGACAGGTG CCCTAGAGTA     780

GCCTGCATCC AGGGACAGGC CCCAGCTGGG TGCTGACACG TCCACCTCCA TCTCTTCCTC     840

AGCACCACCT GTGGCAGGAC CGTCAGTCTT CCTCTTCCCC CCAAAACCCA AGGACACCCT     900

CATGATCTCC CGGACCCCTG AGGTCACGTG CGTGGTGGTG GACGTGAGCC ACGAAGACCC     960

CGAGGTCCAG TTCAACTGGT ACGTGGACGG CGTGGAGGTG CATAATGCCA AGACAAAGCC    1020

ACGGGAGGAG CAGTTCAACA GCACGTTCCG TGTGGTCAGC GTCCTCACCG TTGTGCACCA    1080

GGACTGGCTG AACGGCAAGG AGTACAAGTG CAAGGTCTCC AACAAAGGCC TCCCAGCCCC    1140

CATCGAGAAA ACCATCTCCA AAACCAAAGG TGGGACCCGC GGGGTATGAG GGCCACATGG    1200

ACAGAGGCCG GCTCGGCCCA CCCTCTGCCC TGGGAGTGAC CGCTGTGCCA ACCTCTGTCC    1260

CTACAGGGCA GCCCCGAGAA CCACAGGTGT ACACCCTGCC CCCATCCCGG GAGGAGATGA    1320

CCAAGAACCA GGTCAGCCTG ACCTGCCTGG TCAAAGGCTT CTACCCCAGC GACATCGCCG    1380

TGGAGTGGGA GAGCAATGGG CAGCCGGAGA ACAACTACAA GACCACACCT CCCATGCTGG    1440

ACTCCGACGG CTCCTTCTTC CTCTACAGCA AGCTCACCGT GGACAAGAGC AGGTGGCAGC    1500

AGGGGAACGT CTTCTCATGC TCCGTGATGC ATGAGGCTCT GCACAACCAC TACACGCAGA    1560

AGAGCCTCTC CCTGTCTCCG GGTAAATGAG TGCCACGGCC GGCAAGCCCC CGCTCCCCAG    1620

GCTCTCGGGG TCGCGTGAGG ATGCTTGGCA CGTACCCCGT GTACATACTT CCCAGGCACC    1680
```

```
CAGCATGGAA ATAAAGCACC CAGCGCTGCC CTGGGCCCCT GCGAGACTGT GATGGTTCTT    1740

TCCGTGGGTC AGGCCGAGTC TGAGGCCTGA GTGGCATGAG GGAGGCAGAG TGGGTC         1796
```

(2) INFORMATION FOR SEQ ID NO:2:

(i) SEQUENCE CHARACTERISTICS:
        (A) LENGTH: 432 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: homo sapien
        (G) CELL TYPE: lymphocyte (xi) SEQUENCE DESCRIPTION: SEQ ID NO:2:

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Glu Arg Lys Cys
        195                 200                 205

Cys Val Glu Cys Pro Pro Cys Pro Ala Pro Val Ala Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Asp Val Ser His Glu Asp Pro
                245                 250                 255

Glu Val Gln Phe Asn Trp Tyr Val Asp Gly Val Glu Val His Asn Ala
            260                 265                 270

Lys Thr Lys Pro Arg Glu Glu Gln Phe Asn Ser Thr Phe Arg Val Val
        275                 280                 285

Ser Val Leu Thr Val Val His Gln Asp Trp Leu Asn Gly Lys Glu Tyr
    290                 295                 300

Lys Cys Lys Val Ser Asn Lys Gly Leu Pro Ala Pro Ile Glu Lys Thr
305                 310                 315                 320
```

```
Ile Ser Lys Thr Lys Gly Gln Pro Arg Glu Pro Gln Val Tyr Thr Leu
            325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Met Leu Asp
            370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                    405                 410                 415

Leu His Asn His Tyr Thr Gln Lys Ser Leu Ser Leu Ser Pro Gly Lys
            420                 425                 430
```

(2) INFORMATION FOR SEQ ID NO:3:

(i) SEQUENCE CHARACTERISTICS:
        (A) LENGTH: 2482 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:3:

```
CAAGCCCAGA GCCCTGCCAT TTCTGTGGGC TCAGGTCCCT ACTGCTCAGC CCCTTCCTCC    60
CTCGGCAAGG CCACAATGAA CCGGGGAGTC CCTTTTAGGC ACTTGCTTCT GGTGCTGCAA   120
CTGGCGCTCC TCCCAGCAGC CACTCAGGGA AGAAAGTGG TGCTGGGCAA AAAAGGGGAT   180
ACAGTGGAAC TGACCTGTAC AGCTTCCCAG AAGAAGAGCA TACAATTCCA CTGGAAAAAC   240
TCCAACCAGA TAAAGATTCT GGGAAATCAG GGCTCCTTCT TAACTAAAGG TCCATCCAAG   300
CTGAATGATC GCGCTGACTC AAGAAGAAGC CTTTGGGACC AAGGAAACTT CCCCCTGATC   360
ATCAAGAATC TTAAGATAGA AGACTCAGAT ACTTACATCT GTGAAGTGGA GGACCAGAAG   420
GAGGAGGTGC AATTGCTAGT GTTCGGATTG ACTGCCAACT CTGACACCCA CCTGCTTCAG   480
GGGCAGAGCC TGACCCTGAC CTTGGAGAGC CCCCCTGGTA GTAGCCCCTC AGTGCAATGT   540
AGGAGTCCAA GGGGTAAAAA CATACAGGGG GGGAAGACCC TCTCCGTGTC TCAGCTGGAG   600
CTCCAGGATA GTGGCACCTG GACATGCACT GTCTTGCAGA ACCAGAAGAA GGTGGAGTTC   660
AAAATAGACA TCGTGGTGCT AGCTTTCGCC TCCACCAAGG GCCCATCGGT CTTCCCCCTG   720
GCGCCCTGCT CCAGGAGCAC CTCCGAGAGC ACAGCCGCCC TGGGCTGCCT GGTCAAGGAC   780
TACTTCCCCG AACCGGTGAC GGTGTCGTGG AACTCAGGCG CTCTGACCAG CGGCGTGCAC   840
ACCTTCCCAG CTGTCCTACA GTCCTCAGGA CTCTACTCCC TCAGCAGCGT GGTGACCGTG   900
CCCTCCAGCA ACTTCGGCAC CCAGACCTAC ACCTGCAACG TAGATCACAA GCCCAGCAAC   960
ACCAAGGTGG ACAAGACAGT TGGTGAGAGG CCAGCTCAGG GAGGGAGGGT GTCTGCTGGA  1020
AGCCAGGCTC AGCCCTCCTG CCTGGACGCA CCCCGGCTGT GCAGCCCCAG CCCAGGGCAG  1080
CAAGGCAGGC CCCATCTGTC TCCTCACCCG GAGGCCTCTG CCCGCCCCAC TCATGCTCAG  1140
GGAGAGGGTC TTCTGGCTTT TTCCACCAGG CTCCAGGCAG GCACAGGCTG GGTGCCCCTA  1200
CCCCAGGCCC TTCACACACA GGGGCAGGTG CTTGGCTCAG ACCTGCCAAA AGCCATATCC  1260
```

```
GGGAGGACCC TGCCCCTGAC CTAAGCCGAC CCCAAAGGCC AAACTGTCCA CTCCCTCAGC    1320

TCGGACACCT TCTCTCCTCC CAGATCCGAG TAACTCCCAA TCTTCTCTCT GCAGAGCGCA    1380

AATGTTGTGT CGAGTGCCCA CCGTGCCCAG GTAAGCCAGC CCAGGCCTCG CCCTCCAGCT    1440

CAAGGCGGGA CAGGTGCCCT AGAGTAGCCT GCATCCAGGG ACAGGCCCCA GCTGGGTGCT    1500

GACACGTCCA CCTCCATCTC TTCCTCAGCA CCACCTGTGG CAGGACCGTC AGTCTTCCTC    1560

TTCCCCCCAA AACCCAAGGA CACCCTCATG ATCTCCCGGA CCCCTGAGGT CACGTGCGTG    1620

GTGGTGGACG TGAGCCACGA AGACCCCGAG GTCCAGTTCA ACTGGTACGT GGACGGCGTG    1680

GAGGTGCATA ATGCCAAGAC AAAGCCACGG GAGGAGCAGT TCAACAGCAC GTTCCGTGTG    1740

GTCAGCGTCC TCACCGTTGT GCACCAGGAC TGGCTGAACG GCAAGGAGTA CAAGTGCAAG    1800

GTCTCCAACA AAGGCCTCCC AGCCCCCATC GAGAAAACCA TCTCCAAAAC CAAAGGTGGG    1860

ACCCGCGGGG TATGAGGGCC ACATGGACAG AGGCCGGCTC GGCCCACCCT CTGCCCTGGG    1920

AGTGACCGCT GTGCCAACCT CTGTCCCTAC AGGGCAGCCC CGAGAACCAC AGGTGTACAC    1980

CCTGCCCCCA TCCCGGGAGG AGATGACCAA GAACCAGGTC AGCCTGACCT GCCTGGTCAA    2040

AGGCTTCTAC CCCAGCGACA TCGCCGTGGA GTGGGAGAGC AATGGGCAGC CGGAGAACAA    2100

CTACAAGACC ACACCTCCCA TGCTGGACTC CGACGGCTCC TTCTTCCTCT ACAGCAAGCT    2160

CACCGTGGAC AAGAGCAGGT GGCAGCAGGG GAACGTCTTC TCATGCTCCG TGATGCATGA    2220

GGCTCTGCAC AACCACTACA CGCAGAAGAG CCTCTCCCTG TCTCCGGGTA AATGAGTGCC    2280

ACGGCCGGCA AGCCCCCGCT CCCCAGGCTC TCGGGGTCGC GTGAGGATGC TTGGCACGTA    2340

CCCCGTGTAC ATACTTCCCA GGCACCCAGC ATGGAAATAA AGCACCCAGC GCTGCCCTGG    2400

GCCCCTGCGA GACTGTGATG GTTCTTTCCG TGGGTCAGGC CGAGTCTGAG GCCTGAGTGG    2460

CATGAGGGAG GCAGAGTGGG TC                                              2482

(2) INFORMATION FOR SEQ ID NO:4:

(i) SEQUENCE CHARACTERISTICS:
        (A) LENGTH: 530 amino acids
        (B) TYPE: amino acid
        (C) STRANDEDNESS: unknown
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:4:

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110
```

-continued

```
Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Leu Ala Phe Ala Ser Thr Lys
            195                 200                 205

Gly Pro Ser Val Phe Pro Leu Ala Pro Cys Ser Arg Ser Thr Ser Glu
            210                 215                 220

Ser Thr Ala Ala Leu Gly Cys Leu Val Lys Asp Tyr Phe Pro Glu Pro
225                 230                 235                 240

Val Thr Val Ser Trp Asn Ser Gly Ala Leu Thr Ser Gly Val His Thr
                245                 250                 255

Phe Pro Ala Val Leu Gln Ser Ser Gly Leu Tyr Ser Leu Ser Ser Val
                260                 265                 270

Val Thr Val Pro Ser Ser Asn Phe Gly Thr Gln Thr Tyr Thr Cys Asn
            275                 280                 285

Val Asp His Lys Pro Ser Asn Thr Lys Val Asp Lys Thr Val Glu Arg
            290                 295                 300

Lys Cys Cys Val Glu Cys Pro Pro Cys Pro Ala Pro Pro Val Ala Gly
305                 310                 315                 320

Pro Ser Val Phe Leu Phe Pro Pro Lys Pro Lys Asp Thr Leu Met Ile
                325                 330                 335

Ser Arg Thr Pro Glu Val Thr Cys Val Val Val Asp Val Ser His Glu
                340                 345                 350

Asp Pro Glu Val Gln Phe Asn Trp Tyr Val Asp Gly Val Glu Val His
            355                 360                 365

Asn Ala Lys Thr Lys Pro Arg Glu Glu Gln Phe Asn Ser Thr Phe Arg
370                 375                 380

Val Val Ser Val Leu Thr Val Val His Gln Asp Trp Leu Asn Gly Lys
385                 390                 395                 400

Glu Tyr Lys Cys Lys Val Ser Asn Lys Gly Leu Pro Ala Pro Ile Glu
                405                 410                 415

Lys Thr Ile Ser Lys Thr Lys Gly Gln Pro Arg Glu Pro Gln Val Tyr
            420                 425                 430

Thr Leu Pro Pro Ser Arg Glu Glu Met Thr Lys Asn Gln Val Ser Leu
            435                 440                 445

Thr Cys Leu Val Lys Gly Phe Tyr Pro Ser Asp Ile Ala Val Glu Trp
            450                 455                 460

Glu Ser Asn Gly Gln Pro Glu Asn Asn Tyr Lys Thr Thr Pro Pro Met
465                 470                 475                 480

Leu Asp Ser Asp Gly Ser Phe Phe Leu Tyr Ser Lys Leu Thr Val Asp
                485                 490                 495

Lys Ser Arg Trp Gln Gln Gly Asn Val Phe Ser Cys Ser Val Met His
                500                 505                 510

Glu Ala Leu His Asn His Tyr Thr Gln Lys Ser Leu Ser Leu Ser Pro
            515                 520                 525

Gly Lys
```

(2) INFORMATION FOR SEQ ID NO:5:

(i) SEQUENCE CHARACTERISTICS:
        (A) LENGTH: 1149 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:5:

```
CAAGCCCAGA GCCCTGCCAT TTCTGTGGGC TCAGGTCCCT ACTGCTCAGC CCCTTCCTCC      60
CTCGGCAAGG CCACAATGAA CCGGGGAGTC CCTTTTAGGC ACTTGCTTCT GGTGCTGCAA     120
CTGGCGCTCC TCCCAGCAGC CACTCAGGGA AGAAAGTGG TGCTGGGCAA AAAGGGGAT      180
ACAGTGGAAC TGACCTGTAC AGCTTCCCAG AAGAAGAGCA TACAATTCCA CTGGAAAAAC     240
TCCAACCAGA TAAAGATTCT GGGAAATCAG GGCTCCTTCT TAACTAAAGG TCCATCCAAG     300
CTGAATGATC GCGCTGACTC AAGAAGAAGC CTTTGGGACC AAGGAAACTT CCCCCTGATC     360
ATCAAGAATC TTAAGATAGA AGACTCAGAT ACTTACATCT GTGAAGTGGA GGACCAGAAG     420
GAGGAGGTGC AATTGCTAGT GTTCGGATTG ACTGCCAACT CTGACACCCA CCTGCTTCAG     480
GGGCAGAGCC TGACCCTGAC CTTGGAGAGC CCCCCTGGTA GTAGCCCCTC AGTGCAATGT     540
AGGAGTCCAA GGGGTAAAAA CATACAGGGG GGGAAGACCC TCTCCGTGTC TCAGCTGGAG     600
CTCCAGGATA GTGGCACCTG GACATGCACT GTCTTGCAGA ACCAGAAGAA GGTGGAGTTC     660
AAAATAGACA TCGTGGTGCT AGCTTTCACT GTGGCTGCAC CATCTGTCTT CATCTTCCCG     720
CCATCTGATG AGCAGTTGAA ATCTGGAACT GCCTCTGTTG TGTGCCTGCT GAATAACTTC     780
TATCCCAGAG AGGCCAAAGT ACAGTGGAAG GTGGATAACG CCCTCCAATC GGGTAACTCC     840
CAGGAGAGTG TCACAGAGCA GGACAGCAAG GACAGCACCT ACAGCCTCAG CAGCACCCTG     900
ACGCTGAGCA AAGCAGACTA CGAGAAACAC AAAGTCTACG CCTGCGAAGT CACCCATCAG     960
GGCCTGAGCT CGCCCGTCAC AAAGAGCTTC AACAGGGGAG AGTGTTAGAG GGAGAAGTGC    1020
CCCCACCTGC TCCTCAGTTC CAGCCTGACC CCCTCCCATC CTTTGGCCTC TGACCCTTTT    1080
TCCACAGGGG ACCTACCCCT ATTGCGGTCC TCCAAGCTCA TCTTTCACCT CACCCCCCTC    1140
CTCCTCCTT                                                           1149
```

(2) INFORMATION FOR SEQ ID NO:6:

(i) SEQUENCE CHARACTERISTICS:
        (A) LENGTH: 310 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: homo sapien
        (G) CELL TYPE: lymphocyte (xi) SEQUENCE DESCRIPTION: SEQ ID NO:6:

```
Met Asn Arg Gly Val Pro Phe Arg His Leu Leu Leu Val Leu Gln Leu
1               5                  10                  15

Ala Leu Leu Pro Ala Ala Thr Gln Gly Lys Lys Val Val Leu Gly Lys
```

-continued

```
                20                  25                  30
Lys Gly Asp Thr Val Glu Leu Thr Cys Thr Ala Ser Gln Lys Lys Ser
             35                  40                  45
Ile Gln Phe His Trp Lys Asn Ser Asn Gln Ile Lys Ile Leu Gly Asn
 50                  55                  60
Gln Gly Ser Phe Leu Thr Lys Gly Pro Ser Lys Leu Asn Asp Arg Ala
 65                  70                  75                  80
Asp Ser Arg Arg Ser Leu Trp Asp Gln Gly Asn Phe Pro Leu Ile Ile
                 85                  90                  95
Lys Asn Leu Lys Ile Glu Asp Ser Asp Thr Tyr Ile Cys Glu Val Glu
            100                 105                 110
Asp Gln Lys Glu Glu Val Gln Leu Leu Val Phe Gly Leu Thr Ala Asn
            115                 120                 125
Ser Asp Thr His Leu Leu Gln Gly Gln Ser Leu Thr Leu Thr Leu Glu
            130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Thr Val Ala Ala
            195                 200                 205
Pro Ser Val Phe Ile Phe Pro Pro Ser Asp Glu Gln Leu Lys Ser Gly
            210                 215                 220
Thr Ala Ser Val Val Cys Leu Leu Asn Asn Phe Tyr Pro Arg Glu Ala
225                 230                 235                 240
Lys Val Gln Trp Lys Val Asp Asn Ala Leu Gln Ser Gly Asn Ser Gln
                245                 250                 255
Glu Ser Val Thr Glu Gln Asp Ser Lys Asp Ser Thr Tyr Ser Leu Ser
            260                 265                 270
Ser Thr Leu Thr Leu Ser Lys Ala Asp Tyr Glu Lys His Lys Val Tyr
            275                 280                 285
Ala Cys Glu Val Thr His Gln Gly Leu Ser Ser Pro Val Thr Lys Ser
290                 295                 300
Phe Asn Arg Gly Glu Cys
305                 310
```

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: unknown (ii) MOLECULE TYPE: DNA (vi) ORIGINAL SOURCE:
        (A) ORGANISM: Homo sapiens
        (G) CELL TYPE: Lymphocyte (xi) SEQUENCE DESCRIPTION: SEQ ID NO:7:

GACACAACAT TTGCGCTCGA AAGCTAGCAC CACG                    34

(2) INFORMATION FOR SEQ ID NO:8:

(i) SEQUENCE CHARACTERISTICS:
        (A) LENGTH: 33 base pairs (B) TYPE: nucleic acid
        (C) STRANDEDNESS: single
        (D) TOPOLOGY: unknown (ii) MOLECULE TYPE: DNA (vi) ORIGINAL SOURCE:
        (A) ORGANISM: Homo sapiens
        (G) CELL TYPE: Lymphocyte (xi) SEQUENCE DESCRIPTION: SEQ ID NO:8:

GGGCCCTTGG TGGAGGCGAA AGCTAGCACC ACG                33

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: DNA (vi) ORIGINAL SOURCE:
        (A) ORGANISM: Homo sapiens
        (G) CELL TYPE: Lymphocyte (xi) SEQUENCE DESCRIPTION: SEQ ID NO:9:

GATGGTGCAG CCACAGTGAA AGCTAGCACC ACG                33

NON-PEPTIDYL MOIETY-CONJUGATED CD4-GAMMA2 AND CD4-IGG2 IMMUNOCONJUGATES, AND USES THEREOF

This application is a continuation-in-part of U.S. Ser. No. 08/379,516, filed Feb. 3, 1995 which is a 371 of PCT international Application No. PCT/US93/07422, International filing date: Aug. 6, 1993, which is a continuation-in-part of U.S. Ser. No. 07/927,931, filed Aug. 7, 1992, now abandoned.

BACKGROUND OF THE INVENTION

Throughout this application, various publications are referenced by Arabic numerals. Full citations for these publications may be found at the end of the specification immediately preceding the claims. The disclosure of these publications is hereby incorporated by reference into this application to describe more fully the state of the art to which this invention pertains.

The life cycle of animal viruses is characterized by a series of events that are required for the productive infection of the host cell. The initial step in the replicative cycle is the attachment of the virus to the cell surface which is mediated by the specific interaction of the viral attachment protein (VAP) to receptors on the surface of the target cell. The pattern of expression of these receptors is largely responsible for the host range and tropic properties of viruses. The interaction of the VAP with cellular receptors therefore plays a critical role in infection and pathogenesis of viral diseases and represents an important area to target the development of anti-viral therapeutics.

Cellular receptors may comprise of all of the components of membranes, including proteins, carbohydrates, and lipids. Identification of the molecules mediating the attachment of viruses to the target cell surface has been made in a few instances. The most extensively characterized viral receptor protein is CD4 (T4) (1). CD4 is a nonpolymorphic cell surface glycoprotein that is expressed primarily on the surface of helper T lymphocytes, cells of the monocyte/macrophage lineage and dendritic cells. CD4 associates with major histocompatibility complex (MHC) class II molecules on the surface of antigen-presenting cells to mediate efficient cellular immune response interactions. In humans, CD4 is also the target of interaction with the human immunodeficiency virus (HIV).

HIV primarily infects helper T lymphocytes, monocytes, macrophages and dendritic cells—cells that express surface CD4. HIV-infected helper T lymphocytes die, and the loss of these CD4+T lymphocytes is one marker of the progress of HIV infection. The depletion of these cells is probably an important cause of the loss of immune function which results in the development of the human acquired immune deficiency syndrome (AIDS). In contrast to helper T lymphocytes, other CD4+ cells, notably dendritic cells, monocyte and macrophages, are chronically infected by HIV. They produce virus over a long period of time and appear to be major reservoirs of virus in vivo (2, 3).

The initial phase of the HIV replicative cycle involves the high affinity interaction between the HIV exterior envelope glycoprotein gp120 and surface CD4 (Kd approximately $4 \times 10^{-9}$ M) (4). Several lines of evidence demonstrate the requirement of this interaction for viral infectivity. In vitro, the introduction of a functional cDNA encoding CD4 into human cells which do not express CD4 is sufficient to render otherwise resistant cells susceptible to HIV infection (5). In vivo, viral infection appears to be restricted to cells expressing CD4. Following the binding of HIV gp120 to cell surface CD4, viral and target cell membranes fuse, resulting in the introduction of the viral nucleocapsid into the target cell cytoplasm.

Characterization of the interaction between HIV gp120 and CD4 has been facilitated by the isolation of cDNA clones encoding both molecules (6,7). CD4 is a nonpolymorphic, lineage-restricted cell surface glycoprotein that is a member of the immunoglobulin gene superfamily. High-level expression of both full-length CD4 and truncated, soluble versions of CD4 (sCD4) have been described in stable expression systems. The availability of large quantities of purified sCD4 has permitted a detailed understanding of the structure of this complex glycoprotein. Mature CD4 has a relative molecular mass (Mr) of 55 kilodaltons and consists of an amino-terminal 372 amino acid extracellular domain containing four tandem immunoglobulin-like regions denoted V1–V4, followed by a 23 amino acid transmembrane domain and a 38 amino acid cytoplasmic segment. The amino-terminal immunoglobulin-like Vi domain bears 32% homology with kappa light chain variable domains. Three of the four immunoglobulin-like domains contain a disulphide bond (V1, V2 and V4), and both N-linked glycosylation sites in the carboxy-terminal portion of the molecule are utilized (4, 8).

Experiments using truncated sCD4 proteins demonstrate that the determinants of high-affinity binding to HIV gp120 lie within the V1 domain (9–11). Mutational analysis of V1 has defined a discrete gp120 binding site (residues 38–52 of the mature CD4 protein) that comprises a region structurally homologous to the second complementarity-determining region (CDR2) of immunoglobulins (11). The production of large quantities of V1V2 has permitted a structural analysis of the two amino-terminal immunoglobulin-like domains. The structure determined at 2.3 angstrom resolution reveals that the molecule has two tightly associated domains containing the immunoglobulin-fold connected by a continuous beta strand. The putative binding sites for monoclonal antibodies, class II MHC molecules and HIV gp120 (as determined by mutational analysis) map on the molecular surface (12, 13).

A number of therapeutic strategies have been proposed using CD4-based molecules to target HIV or HIV-infected cells which express gp120. These strategies have the advantage that they depend on the interaction between CD4 and gp120. This interaction is essential for virus infection, so CD4-based strategies should be effective against all strains of HIV. Moreover, it is highly unlikely that escape mutants would develop with mutations in gp120 which eliminate CD4 binding. This is in marked contrast with therapeutic strategies which target other regions of gp120 (e.g. vaccine approaches) or other viral proteins (e.g reverse transcriptase) where the therapy is effective against a limited subset of HIV strains, and/or the virus can mutate and become resistant to the therapy.

In one example of CD4-based therapies, a soluble version of the entire extracellular segment of CD4 (V1–V4, termed sCD4) has been developed (14). In vitro experiments demonstrate that: 1) SCD4 acts as a "molecular decoy" by binding to HIV gp120 and inhibiting viral attachment to and subsequent infection of human cells; 2) sCD4 "strips" the viral envelope glycoprotein gp120 from the viral surface (although this is more important with laboratory isolates of HIV than with clinical isolates of the virus); and 3) sCD4 blocks the intercellular spread of virus from HIV-infected cells to uninfected cells by inhibiting virus-mediated cell fusion (1, 15).

In addition to in vitro results, experiments with sCD4 in simian immunodeficiency virus (SIV)-infected rhesus monkeys have been described. These studies demonstrated that administration of sCD4 to SIV-infected rhesus monkeys leads to a diminution of the viral reservoir.

Phase I human clinical trials with sCD4 demonstrated that there is no significant toxicity or immunogenicity associated with administration of sCD4 at doses as high as 30 mg/day. Preliminary antiviral studies were inconclusive with respect to CD4 cell count and levels of HIV antigen (16, 17).

Although these in vitro, primate and human studies with sCD4 produced encouraging results, they also defined some limitations. In particular, the measured serum half-life of sCD4 is very short (30–45 minutes in humans following intravenous administration (16,17)). It is hard to imagine that sCD4 administration could eliminate HIV from the body, but rather it would be used to delay or prevent the spread of infection and the development of disease. Therefore a therapeutic regimen might involve regular treatment with the protein. However, the short half-life of sCD4 might make it difficult to maintain sufficient levels in the plasma to give a therapeutic effect. This problem is compounded by the fact that much higher levels of sCD4 are required to neutralize clinical isolates of HIV compared to laboratory isolates, although all clinical isolates can be neutralized at some concentration (18). To make a CD4-based molecule with a longer half-life, several groups have now made chimeric CD4-based molecules which comprise the gp120 binding region of CD4 and another protein such as an immunoglobulin molecule. These molecules are described in greater detail below. Another drawback to sCD4 is that it does not kill HIV-infected cells such as monocytes/macrophages and dendritic cells. These cells act as reservoirs for HIV and chronically produce virus which infects other cells such as helper T lymphocytes. The CD4-based chimeras mentioned above may also have limited efficacy in killing HIV-infected cells. While a chimera between CD4 and human immunoglobulin gamma 1 may kill HIV infected cells by antibody-dependent cellular cytotoxicity (ADCC) in vitro, experience with anti-tumor monoclonal antibodies suggests that monoclonal antibody-mediated ADCC is rarely effective in vivo. Therefore, another CD4-based approach has been developed where sCD4 is linked to a toxin molecule. These chimeras can bind to, and kill, HIV-infected cells which express gp120 on their surfaces.

In one study, sCD4 was coupled to the deglycosylated A chain of ricin which inactivates ribosomes, therefore inhibiting protein synthesis and killing the cell. This fusion protein was reported to lyse cells infected with five different isolates of HIV, but was nontoxic to uninfected cells (19).

In another study, the V1V2 domains of CD4 were coupled to domains II and III of Pseudomonas exotoxin A (sCD4-PE40) (20). This toxin also blocks protein synthesis, in this case by inactivating elongation factor 2. The sCD4-PE40 fusion protein bound to, and inhibited protein synthesis in, cells expressing the HIV envelope glycoprotein gp120 (20). It has been shown that the sCD4-PE40 conjugate kills cells infected with both laboratory and clinical HIV isolates. This is in contrast to the fact that sCD4 and other CD4-based molecules are much less effective at neutralizing clinical isolates than laboratory isolates of HIV (18). The mechanism for the difference in susceptibility of primary and laboratory isolates appears to be that sCD4 strips gp120 from the virions of laboratory isolates much more efficiently than from clinical isolates (21). However, the resistance to stripping of gp120 in clinical isolates is an asset when using sCD4-toxin molecules to target HIV-infected cells in vivo.

Further studies of CD4-PE40 have shown that this conjugate is capable of eliminating HIV from cultures of infected cells when used in combination with the reverse transcriptase blocker AZT (22). This effect has now been seen with laboratory and clinical isolates, as well as in a variety of different cell types.

In yet another study, a fragment of Diphtheria toxin was genetically fused with the V1 and V2 domains of CD4 (23). This toxin also acts by inactivating elongation factor 2. The CD4-diphtheria toxin fusion protein was effective and specific in killing HIV-infected cells. HIV-infected cultures became resistant to the CD4-Diphtheria conjugate after long term treatment (18 days) for unknown reasons. The significance of this observation is unclear, as the phenomenon was not seen with the other toxin conjugates. Moreover, the CD4-diphtheria toxin study has only been performed using a laboratory isolate of HIV and it will be important to assess its activity against primary clinical isolates, as well as in other cell types.

These CD4-toxin conjugates have some major drawbacks. First, being based on SCD4 or a smaller fragment of CD4, the half-life of the molecules are very short, resulting in a need for higher and more frequent doses than would otherwise be the case. A second drawback is that the toxin moieties are foreign proteins which are highly immunogenic. The development of a strong immune response to the conjugate limits the number of repeat treatments which might be used in one patient. In a similar context, it has been suggested that immunosuppressive agents will have to be administered together with monoclonal anti-tumor antibody-toxin conjugates for tumor therapy (24). However, in the case of HIV infections where the immune system is already compromised, this approach may not be viable. New families of CD4-based molecules which are toxic to HIV-infected cells are provided in the subject invention. These molecules have many advantages for use in HIV-infected patients to destroy cells which chronically produce HIV, thereby slowing or halting the progress of HIV infections and AIDS. Moreover, the molecules might also be of value in blocking the initial infection of some individuals, for example in babies born of HIV-positive mothers, or in the case of health workers exposed to HIV-positive body fluids. It is likely that transmission in these cases is mainly cell-cell in mechanism, and that killing the infected cells shortly after they enter the target individual could limit or prevent infection.

These CD4-based molecules are based on the conjugation of a non-peptidic toxin or a cytotoxic radioactive moiety with fusion proteins consisting of portions of CD4 and portions of a human immunoglobulin molecule of the gamma 2 subclass. These molecules have considerable advantages over all previously described CD4-based molecules. The properties of immunoglobulins make them a suitable "backbone" for these CD4-based cytotoxic molecules. Immunoglobulins, or antibodies, are the antigen-binding molecules produced by B lymphocytes which comprise the humoral immune response. The basic unit of an immunoglobulin molecule consists of two identical heavy chains and two identical light chains. The amino-terminus of each chain contains a region of variable amino acid sequence (variable region). The variable regions of the heavy and light chains interact to form two antigen binding sites. The carboxy-terminus of each chain contains a region of constant amino acid sequence (constant domain) . The light chain contains a single constant domain, whereas the heavy chain constant domain is subdivided into four separate domains (CH1, hinge, CH2, and CH3). The heavy chains of immunoglobulin molecules are of several types, including mu (M), delta (D), gamma (G), alpha (A) and epsilon (E) . The light chains of immunoglobulin molecules are of two types, either kappa or lambda. Within the individual types of heavy and light chains exist subtypes which may differ in effector function. An assembled immunoglobulin molecule derives its name from the type of heavy chain that it possesses.

The development of monoclonal antibodies has circumvented the inherent heterogeneity of antibodies obtained from serum of animals or humans. However, most monoclonal antibodies are derived from cells of mouse origin and therefore are immunogenic when administered to humans. More recent developments combining the techniques of molecular genetics with monoclonal antibody technology has lead to the production of "humanized" chimeric antibodies in vitro. In these chimeric antibodies, the variable domains of human immunoglobulin heavy and light chains are replaced with specific heavy and light chain variable domains from a murine monoclonal antibody (25–27). The result of this genetic manipulation is a molecule with specificity for a particular antigen and the characteristics of human immunoglobulins.

Sequence and structural analyses of CD4 indicate that the four extracellular domains are immunoglobulin-like. Since the Fc portion of immunoglobulins controls the rate of catabolism of the molecules (serum half-life ranging from 14 to 21 days) and provides various effector functions, several reports describe the replacement of variable and constant domains of immunoglobulins with the immunoglobulin-like domains of CD4 (21–24).

CD4-IgG1 heavy chain fusion proteins resulting in chimeric gammal heavy chain dimers have been described (28). These molecules contain the gammal heavy chain CH1 domain in addition to the hinge, CH2 and CH3 domains. However, heavy chain assembly and secretion from mammalian cells is less efficient if the CH1 domain is expressed in the absence of light chains (32). Subsequently, a CD4-IgG1 heavy chain fusion protein lacking the CH1 domain and the first five amino acids of the hinge region was described which was secreted to high levels (29).

CD4-IgG1 fusion proteins have also been described. Here the V1V2 domains of CD4 were fused to the CH1, hinge, CH2 and CH3 domains of a gammal heavy chain, and the V1V2 domains of CD4 were fused to the constant region of a kappa light chain (33). CD4-IgM heavy chain fusion proteins have also been described (34).

These fusion proteins have been successfully used to block HIV infection in vitro, and in one case to block the infection of Chimpanzees by a laboratory strain of HIV. As expected, the CD4-immunoglobulin chimeras have a much longer half-life in vivo than does sCD4. As discussed above, however, it is unlikely that these molecules can destroy HIV-infected cells in patients who are already infected with HIV. Their efficacy against primary isolates of HIV has yet also to be established.

These fusion proteins retain various effector functions of immunoglobulin molecules, such as Fc receptor binding, cell-mediated transfer via an Fc receptor-dependent mechanism and complement activation (29). While these effector functions might have utility in some therapeutic regimens, they are a disadvantage in the present context of developing cytotoxic drugs consisting of toxins or radionuclides linked to CD4-immunoglobulin chimeras.

Many of the functions of antibodies are mediated through their interaction with Fc receptors. These receptors are found on a variety of cells including macrophages, other leucocytes, platelets and placental trophoblasts (35). The Fc receptor binds to the Fc portion of immunoglobulins and the complex can trigger a variety of responses depending on cell type. In the case of macrophages, the response can include phagocytosis and ADCC. With placental trophoblasts, IgG1 binding leads to transfer of the antibody to the fetus.

Human cells express a number of different Fc receptors which are specific for different immunoglobulin isotypes. Three types of human Fc receptor have been described which bind human IgG (Fc$\gamma$RI, Fc$\gamma$RII and Fc$\gamma$RIII) (35). Fc$\delta$RI has a much higher affinity for monomeric IgG than do Fc$\gamma$RII and Fc$\gamma$RIII. The rank order of activity of Fc$\gamma$RI for IgG isotypes is IgG1=IgG3>IgG4. IgG2 does not bind to this receptor. Fc$\gamma$RII binds IgG1 and IgG3 more strongly than IgG2 or IgG4. Fc$\gamma$RIII recognizes only IgG1 and IgG3 (35).

A cytotoxic molecule with FcR-binding capability may kill FcR-bearing cells in an indiscriminate manner. To construct a CD4-based molecule which specifically kills HIV-infected cells, it would be ideal to base it on IgG2 which exhibits little or no FcR binding. Moreover, human IgG2 antibodies exhibit minimal allotypic variation while human IgG1 antibodies have considerable variation. Therefore, to avoid potential immunogenic responses to recombinant molecules containing immunoglobulin domains, a molecule which is the least polymorphic was chosen.

The CD4-IgG2 molecules have advantages relative to the CD4-IgG1 heavy chain dimers which have been described previously. They are also superior to the CD4-toxin molecules which have been developed in the past. Specifically, a CD4-gamma2 chimeric heavy chain homodimer was constructed which contains the V1V2 domains of CD4 and which is efficiently assembled intracellularly and efficiently secreted from mammalian cells as a homodimer, enabling high recovery and purification from the medium of cells expressing this chimeric heavy chain homodimer. To construct this homodimer, the entire hinge, CH2, and CH3 domains from a human gamma2 heavy chain were used, resulting in a chimeric molecule containing the constant domains of a human IgG2 molecule responsible for dimerization and efficient secretion. This is in contrast to the heavy chain dimers described by Capon and Gregory (36) which include the CH1 domain in the CD4-IgG1 heavy chain dimer, resulting in poor secretion and recovery from cell culture medium of the recombinant molecule. Also included is the entire hinge domain of gamma2 heavy chain in the CD4-gamma2 chimeric heavy chain homodimer of this invention to provide efficient dimerization, since the cysteine residues contained in this domain are responsible for forming the disulphide links to the second chain of the homodimer, positioning the two chains in the correct spatial alignment and facilitating formation of the antigen combining site.

In addition to the CD4-gamma2 chimeric heavy chain homodimers, CD4-IgG2 heavy chains were also constructed, which contain the V1V2 domains of CD4 fused to the CH1, hinge, CH2 and CH3 domains of human gamma2 heavy chain. CD4-kappa chimeric light chains were also constructed which contain the Vi and V2 domains of CD4 fused to the entire constant domain of human kappa light chains. When these vectors are co-expressed, they produce a heterotetramer comprising two CD4-IgG2 chimeric heavy chains and two CD4-kappa chimeric light chains. Producing heavy chains which contain the CH1 domain enables efficient association with the CD4-kappa chimeric light chains, resulting in efficient secretion of a CD4-IgG2 chimeric heterotetramer. These CD4-IgG2 chimeric heterotetramers possess increased serum half-lives and increased avidity for HIV as compared with heavy chain dimers.

These CD4-gamma 2 chimeric heavy chain dimers and CD4-IgG2 chimeric heterotetramers are linked to non-immunogenic toxic moieties. Two classes of cytotoxic conjugates have been invented. In the first class, the dimers or tetramers are linked to a non-protein toxin.

One example of this toxin is a member or derivative of the enediyne family of anti-tumor antibiotics, including calicheamicin, esperamicins or dynemicins (37, 38). These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the conjugates. Such site-directed linking methods have the advantage of reducing the possible effects of linkage on the binding properties of the CD4 portion of the conjugate.

The second class of cytotoxic conjugates consists of the dimers or tetramers linked to a radionuclide which produces cytotoxic radiation. Examples of the radionuclides which are used include β-particle and α-particle emitters such as $^{125}I$, $^{131}I$, $^{90}Y$ and $^{212}Bi$.

These isotopes are chemically-linked to the dimers or tetramers by techniques which have been used successfully to label monoclonal antibodies and other molecules. These linking technologies include random labeling and site-directed labeling. In the latter case, the labeling is directed at specific sites on the dimer or tetramer, such as the N-linked sugar residues present only on the Fc portion of the conjugates.

In previous studies, anti-tumor antibodies labelled with these isotopes have been used successfully to destroy cells in solid tumors as well as lymphomas/leukemias in animal models, and in some cases in humans (39). The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example HIV-infected cells to which the conjugate has attached or has entered. They have little or no effect on neighboring cells. Radionuclides are essentially non-immunogenic.

Both classes of cytotoxic dimer and tetramer conjugates described above have several advantages over other therapeutics which have been described for use against HIV infections. They have a CD4-based mode of action which permits the targeting of all HIV strains and prevents the selection of viral escape mutants. Like other CD4-based molecules, the conjugates may exhibit synergism when used in combination with other anti-HIV drugs such as AZT. Being conjugated to fragments of IgG2, the molecules have much longer half-lives in vivo than do sCD4-based molecules. They also have the advantage of being dimeric or tetrameric, which increases the avidity of binding to HIV-infected cells. The conjugates kill HIV-infected cells, thereby reducing the rate of spread of HIV infection in vivo, or eliminating infection entirely. All components of the conjugates have been selected for minimal immunogenicity. Being based on IgG2, the conjugates bind minimally, if at all, to Fc receptors, thereby reducing non-specific cell killing.

One use of these radio-conjugates is in the therapy of HIV infections as discussed supra. However, another important application is the use of similar conjugates to detect and localize HIV-infected cells in patients. In this case the conjugates are linked to a γ-radiation emitting isotope such as $^{111}In$, $^{131}I$ or $^{99m}Tc$. These isotopes emit I-radiation which passes through tissues for detection/imaging purposes, but causes little ionization or cell death. In the case of an isotope such as $^{131}I$, both high energy β-particles and γ-radiation are produced. This isotope can be used in therapeutic or imaging contexts, depending on the number of $^{131}I$ atoms attached to each dimer or tetramer (the specific activity), which governs the cytotoxicity of the dimer or tetramer. Lower specific activities are used for imaging purposes. Such isotopes have been used to image mouse erythroid tumors using leukemia cell-specific monoclonal antibodies labeled with bifunctional radioactive metal chelates (48).

Radioconjugates for diagnostic/imaging purposes would be of value in clinical research to understand the course of HIV infections, as well as in clinical diagnostic applications. For example, imaging could be done in conjunction with treatment using the toxin-conjugated or cytotoxic radionuclide-conjugated dimers and tetramers.

The CD4-gamma2 chimeric heavy chain homodimer or CD4-IgG2 chimeric heterotetramer have advantages as imaging agents when compared with antibodies to HIV, since CD4 binds the envelope glycoprotein of all HIV strains with high affinity, whether the envelope glycoprotein is present on the surface of HIV or an HIV-infected cell.

SUMMARY OF THE INVENTION

This invention provides an immunoconjugate which comprises 1) a non-peptidyl toxin and 2) a CD4-gamma2 chimeric heavy chain homodimer linked thereto.

This invention also provides a method of killing HIV-infected cells which comprises contacting HIV-infected cells with the immunoconjugate of the subject invention in an amount effective to kill the cells.

This invention further provides a method of treating an HIV-infected subject so as to reduce the population of HIV-infected cells in the subject which comprises administering to the HIV-infected subject an amount of immunoconjugate of the subject invention effective to kill HIV-infected cells and thereby reduce the population of HIV-infected cells in the HIV-infected subject.

This invention also provides a method of treating a subject so as to reduce the likelihood of the subject's becoming infected with HIV which comprises administering to the subject the immunoconjugate of the subject invention in an amount effective to reduce the likelihood of the subject's becoming infected with HIV.

This invention also provides a pharmaceutical composition which comprises the immunoconjugate of the subject invention in an amount effective to kill HIV-infected cells and thereby reduce the population of HIV-infected cells in an HIV-infected subject and a pharmaceutically acceptable carrier.

This invention also provides an immunoconjugate which comprises 1) a gamma radiation-emitting radionuclide of low to moderate cytotoxicity and 2) a CD4-gamma2 chimeric heavy chain homodimer linked thereto.

This invention also provides a method for imaging HIV-infected tissue present in an HIV-infected subject which comprises administering to the subject an amount of the immunoconjugate of the subject invention effective to permit determining the location of HIV-infected tissue present in the subject under conditions permitting the immunoconjugate to specifically bind to HIV-infected tissue present in the subject, and determining the location of the immunoconjugate specifically bound to HIV-infected tissue present in the subject after a suitable period of time, so as to thereby image HIV-infected tissue present in the HIV-infected subject.

This invention also provides a method for determining the stage of an HIV infection in an HIV-infected subject which comprises imaging HIV-infected tissue present in the HIV-infected subject by the method of the subject invention, and comparing the image so obtained with the image of an HIV-infected subject having an HIV infection at a known stage, so as to thereby determine the stage of the HIV infection in the HIV-infected subject.

This invention also provides a method for determining the prognosis of an HIV-infected subject which comprises imaging HIV-infected tissue present in the HIV-infected subject by the method of the subject invention, and comparing the image so obtained with the image of an HIV-infected subject having a known prognosis, so as to thereby determine the prognosis of the HIV-infected subject.

This invention also provides a method for determining the efficacy of an anti-HIV treatment in an HIV-infected subject which comprises imaging HIV-infected tissue present in the HIV-infected subject by the method of the subject invention, and comparing the image so obtained with the image of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit imaging HIV-infected tissue present in an HIV-infected subject and a pharmaceutically acceptable carrier.

This invention also provides a method for determining the HIV envelope glycoprotein burden in an HIV-infected subject which comprises administering to the subject an amount of the immunoconjugate of the subject invention effective to permit determining the amount of cell membrane-associated or viral membrane-associated HIV envelope glycoprotein present in the subject under conditions permitting the immunoconjugate to specifically bind to cell membrane-associated or viral membrane-associated HIV envelope glycoprotein in the subject, and determining the amount of the immunoconjugate specifically bound to cell membrane-associated or viral membrane-associated HIV envelope glycoprotein in the subject, so as to thereby determine the HIV envelope glycoprotein burden in the HIV-infected subject.

This invention also provides a method for determining the stage of an HIV infection in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having an HIV infection at a known stage, so as to thereby determine the stage of the HIV infection in the HIV-infected subject.

This invention also provides a method for determining the prognosis of an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having a known prognosis, so as to thereby determine the prognosis of the HIV-infected subject.

This invention also provides a method for determining the efficacy of an anti-HIV treatment in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit determining the HIV envelope glycoprotein burden of an HIV-infected subject and a pharmaceutically acceptable carrier. This invention also provides an immunoconjugate which comprises 1) a non-peptidyl toxin and 2) a heterotetramer comprising two heavy chains and two light chains, both heavy chains being either a) IgG2 heavy chains or b) chimeric CD4-IgG2 heavy chains, and both light chains being either a) kappa light chains or b) chimeric CD4kappa light chains, with the proviso that either both heavy chains or both light chains or all four chains are CD4 chimeras, the non-peptidyl toxin being linked either to the heavy chains or to the light chains, or to all four chains.

This invention also provides a method of killing HIV-infected cells which comprises contacting HIV-infected cells with the immunoconjugate of the subject invention in an amount effective to kill the cells.

This invention further provides a method of treating an HIV-infected subject so as to reduce the population of HIV-infected cells in the subject which comprises administering to the HIV-infected subject an amount of immunoconjugate of the subject invention effective to kill HIV-infected cells and thereby reduce the population of HIV-infected cells in the HIV-infected subject.

This invention also provides a method of treating a subject so as to reduce the likelihood of the subject's becoming infected with HIV which comprises administering to the subject the immunoconjugate of the subject invention in an amount effective to reduce the likelihood of the subject's becoming infected with HIV.

This invention also provides a pharmaceutical composition which comprises the immunoconjugate of the subject invention in an amount effective to kill HIV-infected cells and thereby reduce the population of HIV-infected cells in an HIV-infected subject and a pharmaceutically acceptable carrier.

This invention also provides an immunoconjugate which comprises 1) a gamma radiation-emitting radionuclide of low to moderate cytotoxicity and 2) a heterotetramer comprising two heavy chains and two light chains, both heavy chains being either a) IgG2 heavy chains or b) chimeric CD4-IgG2 heavy chains, and both light chains being either a) kappa light chains or b) chimeric CD4kappa light chains, with the proviso that either both heavy chains or both light chains or all four chains are CD4 chimeras, the radionuclide being linked either to the heavy chains or to the light chains, or to all four chains.

This invention also provides a method for imaging HIV-infected tissue present in an HIV-infected subject which comprises administering to the subject an amount of the immunoconjugate of the subject invention effective to permit determining the location of HIV-infected tissue present in the subject under conditions permitting the immunoconjugate to specifically bind to HIV-infected tissue present in the subject, and determining the location of the immunoconjugate specifically bound to HIV-infected tissue present in the subject after a suitable period of time, so as to thereby image HIV-infected tissue present in the HIV-infected subject.

This invention also provides a method for determining the stage of an HIV infection in an HIV-infected subject which comprises imaging HIV-infected tissue present in the HIV-infected subject by the method of the subject invention, and comparing the image so obtained with the image of an HIV-infected subject having an HIV infection at a known stage, so as to thereby determine the stage of the HIV infection in the HIV-infected subject.

This invention also provides a method for determining the prognosis of an HIV-infected subject which comprises imaging HIV-infected tissue present in the HIV-infected subject by the method of the subject invention, and comparing the image so obtained with the image of an HIV-infected subject having a known prognosis, so as to thereby determine the prognosis of the HIV-infected subject.

This invention also provides a method for determining the efficacy of an anti-HIV treatment in an HIV-infected subject which comprises imaging HIV-infected tissue present in the HIV-infected subject by the method of the subject invention, and comparing the image so obtained with the image of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit imaging HIV-infected tissue present in an HIV-infected subject and a pharmaceutically acceptable carrier.

This invention also provides a method for determining the HIV envelope glycoprotein burden in an HIV-infected subject which comprises administering to the subject an amount of the immunoconjugate of the subject invention effective to permit determining the amount of cell membrane-associated or viral membrane-associated HIV envelope glycoprotein present in the subject under conditions permitting the immunoconjugate to specifically bind to cell membrane-associated or viral membrane-associated HIV envelope glycoprotein in the subject, and determining the amount of the immunoconjugate specifically bound to cell membrane-associated or viral membrane-associated HIV envelope glycoprotein in the subject, so as to thereby determine the HIV envelope glycoprotein burden in the HIV-infected subject.

This invention also provides a method for determining the stage of an HIV infection in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having an HIV infection at a known stage, so as to thereby determine the stage of the HIV infection in the HIV-infected subject.

This invention also provides a method for determining the prognosis of an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having a known prognosis, so as to thereby determine the prognosis of the HIV-infected subject.

This invention also provides a method for determining the efficacy of an anti-HIV treatment in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit determining the HIV envelope glycoprotein burden of an HIV-infected subject and a pharmaceutically acceptable carrier.

BRIEF DESCRIPTION OF THE FIGURES

FIG. 3A–3F DNA (SEQ ID NO:1) and predicted protein sequence (SEQ ID NO:2) of a CD4-gamma2 chimeric heavy chain homodimer (one chain). The numbers at the end of each line indicate the nucleotide positions. The numbers above each line indicate the amino acid positions (given in single letter code). The protein domains are indicated above the sequences by arrows.

FIG. 4A–4H DNA (SEQ ID NO:3) and predicted protein sequence (SEQ ID NO:4) of a CD4-IgG2 chimeric heavy chain of the CD4-IgG2 chimeric heterotetramer. The numbers at the end of each line indicate the nucleotide positions. The numbers above each line indicate the amino acid positions (given in single letter code). The protein domains are indicated above the sequences by arrows.

FIG. 5A–5D DNA (SEQ ID NO:5) and predicted protein sequence (SEQ ID NO:6) of a CD4-kappa chimeric light chain of the CD4-IgG2 chimeric heterotetramer. The numbers at the end of each line indicate the nucleotide positions. The numbers above each line indicate the amino acid positions (given in single letter code). The protein domains are indicated above the sequences by arrows.

DETAILED DESCRIPTION OF THE INVENTION

Figure 1A:
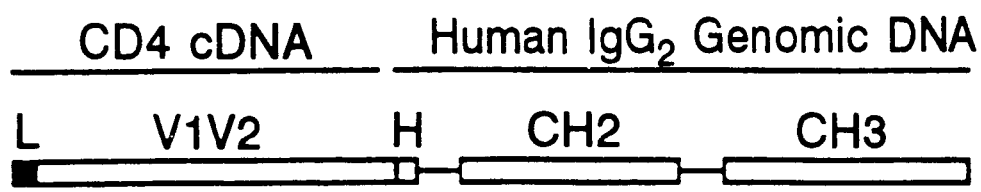
FIG. 1A–1B) Domain structure of CD4-gamma2 chimeric heavy chain gene; B) Protein structure of CD4-gamma2 chimeric heavy chain homodimer. The sequence shown below is the single letter amino acid code of the junction between CD4 (phe179) and the hinge region of human gamma2 heavy chain. Note that the hinge region of a gamma2 heavy chain contains four cysteines (see text for discussion). Abbreviations: L, leader (signal) sequence of human CD4; V1V2, amino-terminal variable-like domains of human CD4; H, hinge region of human gamma2 heavy chain; CH2 and CH3, second and third constant regions of human gamma2 heavy chain; *, predicted N-linked glycosylation sites on CH2 domain (residues 256–258).

Two expression vectors and one plasmid designated CD4-IgG2HC-pRcCMV, CD4-kLC-pRcCMV and CD4-IgG2-pcDNA1, respectively, have been deposited with the American Type Culture Collection, Rockville, Md., U.S.A. 20852, under ATCC Accession Nos. 75193, 75194 and 40952, respectively. These deposits were made pursuant to the provisions of the Budapest Treaty on the International Recognition of the Deposit of Microorganisms for the Purposes of Patent Procedure (Budapest Treaty).

This invention provides an immunoconjugate which comprises 1) a toxin and 2) an HIV glycoprotein recognizing molecule capable of specifically binding to the HIV envelope glycoprotein gp120/gp41. An example of a HIV glycoprotein recognizing molecule is a CD4 containing molecule. It is well known that CD4 is capable of specifically binding to the HIV envelope glycoprotein. Another example of the HIV glycoprotein recognizing molecule is an antibody which is capable of specifically binding to the HIV envelope glycoprotein gp120/gp41. Examples of such antibodies include but are not limited to human monoclonal antibodies that specifically bind to the V3 loop, the CD4-binding site, or other exposed epitopes of gp120, as well as exposed epitopes of gp41.

Specifically, this invention provides an immunoconjugate which comprises 1) a non-peptidyl toxin and 2) a CD4-gamma2 chimeric heavy chain homodimer linked thereto. In one embodiment of the invention, the CD4-gamma2 chimeric heavy chain homodimer is encoded by the expression vector designated CD4-IgG2-pcDNA1 (ATCC No. 40952).

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have stably integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by Okayama (40).

The CD4-gamma2 chimeric heavy chain homodimer may be produced by a) transfecting a mammalian cell with an expression vector for producing the CD4-gamma2 chimeric heavy chain homodimer; b) culturing the resulting transfected mammalian cell under conditions such that CD4-gamma2 chimeric heavy chain homodimer is produced; and c) recovering the CD4-gamma2 chimeric heavy chain homodimer so produced.

Once the vector or DNA sequence containing the constructs has been prepared for expression, the expression vector may be transfected or introduced into an appropriate mammalian cell host. Various techniques for transfection and introduction may be employed, such as protoplast fusion, calcium phosphate precipitation, electroporation or other conventional techniques. In the case of protoplast fusion, the cells are grown in media and screened for the appropriate activity. Expression of the gene(s) results in the production of the fusion protein which corresponds to one chain of the CD4-gamma2 chimeric heavy chain homodimer. This fusion protein may then be treated according to methods known to those skilled in the art to form the chimeric heavy chain homodimer.

Further, methods and conditions for culturing the resulting transfected cells and for recovering the chimeric heavy chain homodimer so produced are well known to those skilled in the art, and may be varied or optimized depending upon the specific expression vector and mammalian host cell employed.

For the purposes of this invention, the preferred host cells for expressing the chimeric heavy chain homodimers of this invention are mammalian cell lines, including, for example, monkey kidney CV1 line transformed by SV40 (COS-7); human embryonic kidney line 293; baby hamster kidney cells (BHK); Chinese hamster ovary-cells-DHFR (CHO); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127) ; and myeloma cell lines.

As used in the subject invention, "non-peptidyl toxin" means any atom, molecule, or combination thereof not comprising an amino acid or its residue which, when in contact with or in proximity to a cell, is capable of killing the cell. As used in the subject invention, "killing" means perturbing the cellular structure or function so as to render the perturbed cell incapable of carrying out at least one of its vital functions. Vital functions include functions necessary for the survival of the cell or of the infecting virus.

The non-peptidyl toxin may be an enediyne anti-cancer antibiotic or derivative thereof. In one embodiment of the subject invention, the enediyne anti-cancer antibiotic is calicheamicin. In another embodiment of the invention, the non-peptidyl toxin is selected from the group consisting of Methotrexate, Doxorubicin, Melphalan, Chlorambucil, ARA-C, Vindesine, Mitomycin C, cis-Platinum, Etoposide, Bleomycin, or 5-Fluorouracil.

The enediyne anticancer antibiotic family of molecules includes calicheamicin, esperamicins, and the dynemicins as well as derivatives and analogues of these molecules. These toxins may be linked to the CD4-gamma2 chimeric heavy chain homodimer by various techniques. These techniques include site-specific linkage of the toxins to the N-linked oligosaccharide side chains on the Fc portion of the CD4-gamma2 chimeric heavy chain homodimers. Alternatively, the toxin may be linked to amino acid residues such as lysine present on both the CD4 and the gamma2 portions of the dimer.

The non-peptidyl toxin may also be a cytotoxic radionuclide. The cytotoxic radionuclide may be an alpha-emitting isotope such as $^{225}$Ac, $^{211}$At, $^{212}$Bi or $^{213}$B. Alternatively, the cytotoxic radionuclide may be an beta-emitting isotope such as $^{186}$Rh, $^{188}$Rh, $^{90}$Y, $^{131}$I or $^{67}$Cu. Furthermore, the cytotoxic radionuclide may be emitting Auger and low energy electron, such as $^{121}$I, $^{123}$I, or $^{77}$Br.

These cytotoxic radionuclides may be conjugated to the dimer by a variety of techniques. These techniques include site-specific linkage to the N-glycosylation sites on the Fc portion of the dimer. Alternatively, the radionuclides may be linked to amino acid residues such as tyrosine or lysine present on both the CD4 and gamma2 portions of the dimer.

This invention also provides a method of killing HIV-infected cells which comprises contacting HIV-infected cells with the immunoconjugate of the subject invention in an amount effective to kill the cells. The amount of immunoconjugate effective to kill the cells may be readily determined using methods known to those skilled in the art.

This invention also provides a method of treating an HIV-infected subject so as to reduce the population of HIV-infected cells in the subject which comprises administering to the HIV-infected subject an amount of immunoconjugate of the subject invention effective to kill HIV-infected cells and thereby reduce the population of HIV-infected cells in the HIV-infected subject.

In the preferred embodiment, the HIV-infected subject is a human.

Methods of administering protein-containing pharmaceuticals are well known to those skilled in the art and include, merely by way of example, subcutaneous, intramuscular and intravascular injection, alone or in combination with other agents, including but not limited to AZT, DDI and D4T.

The amount of immunoconjugate effective to kill HIV-infected cells and thereby reduce the population of HIV-infected cells in the HIV-infected subject may be readily determined using methods known to those skilled in the art.

In the preferred embodiment of the subject invention, the amount of immunoconjugate administered is effective to eliminate the population of HIV-infected cells in the HIV-infected subject. The amount of immunoconjugate effective to eliminate the population of HIV-infected cells in the HIV-infected subject may be readily determined using methods known to those skilled in the art.

This invention also provides a method of treating a subject so as to reduce the likelihood of the subject's becoming infected with HIV which comprises administering to the subject the immunoconjugate of the subject invention in an amount effective to reduce the likelihood of the subject's becoming infected with HIV.

As used in the subject invention, "infection" means the invasion of the subject's own CD4+cells by HIV. As used herein, "HIV" is synonymous with the terms "HIV particle," [11]"HIV virion" or "HIV virus." Thus, the immunoconjugate of the subject invention functions in preventing HIV infection by killing exogenous HIV-infected CD4+cells present in the subject's body before these exogenous cells are able to infect the subject's own CD4+cells.

As used in the subject invention, "reducing the likelihood" means reducing the likelihood of infection by a factor of at least 1.25. The amount of immunoconjugate effective to reduce the likelihood of the subject's becoming infected with HIV may be readily determined using methods known to those skilled in the art.

This invention also provides a pharmaceutical composition which comprises the immunoconjugate of the subject invention in an amount effective to kill HIV-infected cells and thereby reduce the population of HIV-infected cells in an HIV-infected subject and a pharmaceutically acceptable carrier.

Pharmaceutically acceptable carriers are well known to those skilled in the art. In the subject invention, pharmaceutically acceptable carriers include, but are not limited to, 0.01–0.1M and preferably 0.05M phosphate buffer or 0.8% saline. Additionally, pharmaceutically acceptable carriers may be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions including saline and buffered media. Parenteral vehicles include sodium chloride solution, Ringer's dextrose, dextrose and sodium chloride, lactated Ringer's or fixed oils. Intravenous vehicles include fluid and nutrient replenishers, and electrolyte replenishers such as those based on Ringer's dextrose. Preservatives and other additives may also be present, such as antimicrobials, antioxidants, chelating agents and inert gases (41).

This invention provides an immunoconjugate which comprises 1) an imaging readionuclide and 2) an HIV glycoprotein recognizing molecule capable of specifically binding to the HIV envelope glycoprotein gp120/gp41. An example of a HIV glycoprotein recognizing molecule is a CD4 containing molecule. It is well known that CD4 is capable of specifically binding to the HIV envelope glycoprotein. Another example of the HIV glycoprotein recognizing molecule is an antibody which is capable of specifically binding to the HIV envelope glycoprotein gp120/gp41. Examples of such antibodies include but are not limited to human monoclonal antibodies that specifically bind to the V3 loop, the CD4-binding site, or other exposed epitopes of gp120, as well as exposed epitopes of gp41.

Specifically, this invention provides an immunoconjugate which comprises 1) a gamma radiation-emitting radionuclide of low to moderate cytotoxicity and 2) a CD4-gamma2 chimeric heavy chain homodimer linked thereto. In one embodiment of the invention, the CD4-gamma2 chimeric heavy chain homodimer is encoded by the expression vector designated CD4-IgG2-pcDNA1 (ATCC No. 40952).

The gamma radiation-emitting radionuclide may be $^{131}$I, $^{125}$I, $^{123}$I, $^{111}$In, $^{99m}$Tc or $^{188}$Rh. These gamma radiation-emitting radionuclides may be conjugated to the dimer by a variety of techniques. These techniques include site-specific linkage to the N-glycosylation sites on the Fc portion of the dimer, or to sulphydryl groups generated from the disulphide bonds on the dimer. Alternatively, the radionuclides may be linked to amino acid residues such as tyrosine or lysine present on both the CD4 and gamma2 portions of the dimer.

The imaging isotopes may include positron-emitting isotopes such as $^{86}$y, $^{66}$Ga and $^{124}$I. They may also include paramagnetic metals such as Gadolinium which is a stable isotope.

This invention also provides a method for imaging HIV-infected tissue present in an HIV-infected subject which comprises administering to the subject an amount of the immunoconjugate of the subject invention effective to permit determining the location of HIV-infected tissue present in the subject under conditions permitting the immunoconjugate to specifically bind to HIV-infected tissue present in the subject, and determining the location of the immunoconjugate specifically bound to HIV-infected tissue present in the subject after a suitable period of time, so as to thereby image HIV-infected tissue present in the HIV-infected subject.

As used herein, "imaging" means determining the physical location of HIV-infected tissue present in the HIV-infected subject. General methods of imaging using radionuclides are well known to those skilled in the art. The signal detected in the imaging method of the subject invention consists of signal from immunoconjugate bound both to HIV and to HIV-infected cells. The signals from immunoconjugate bound to HIV and from immunoconjugate bound to HIV-infected cells are indistinguishable. Therefore, it is not known what percentage of a given signal is due to immunoconjugate bound to HIV and what percentage is due to immunoconjugate bound to HIV-infected cells.

As used herein, "tissue" means any tissue capable of being infected by HIV, i.e., any tissue comprising CD4+ cells.

The amount of the immunoconjugate of the subject invention effective to permit determining the location of HIV-infected tissue present in an HIV-infected subject is determined according to methods well known to those skilled in the art. The amount of immunoconjugate may be saturating or non-saturating. As used herein, "saturating" means that the number of immunoconjugate HIV envelope glycoprotein-binding sites exceeds the number of HIV envelope glycoprotein sites. Conditions permitting the immunoconjugate to specifically bind to HIV-infected tissue present in an HIV-infected subject are also determined according to methods well known to those skilled in the art, and are illustrated by way of example in the Example section, infra.

Determining the location of the immunoconjugate specifically bound to HIV-infected tissue present in the subject is accomplished according to methods well known to those skilled in the art. Such methods include, by way of example, using a gamma camera to measure the signal emitted by the immunoconjugate bound to HIV-infected tissue present in an HIV-infected subject. The imaging methods and quantitative methods of the subject invention can be combined, and means of doing so are well known in the art. As used herein, a "suitable period of time" means a period of time after which substantially all of the non-specifically bound immunoconjugate has be excreted from the HIV-infected subject, but by which a detectable amount of immunoconjugate remains bound to the HIV-infected tissue present in the HIV-infected subject.

This invention also provides a method for determining the stage of an HIV infection in an HIV-infected subject which comprises imaging HIV-infected tissue present in the HIV-infected subject by the method of the subject invention, and comparing the image so obtained with the image of an HIV-infected subject having an HIV infection at a known stage, so as to thereby determine the stage of the HIV infection in the HIV-infected subject. The image of an HIV-infected subject having an HIV infection at a known stage may be obtained according to methods well known to those skilled in the art. In the subject invention, images from more than one HIV-infected subject having an HIV infection at a known stage may be used.

This invention also provides a method for determining the prognosis of an HIV-infected subject which comprises imaging HIV-infected tissue present in the HIV-infected subject by the method of the subject invention, and comparing the image so obtained with the image of an HIV-infected subject having a known prognosis, so as to thereby determine the prognosis of the HIV-infected subject.

The image of an HIV-infected subject having a known prognosis may be obtained according to methods well known to those skilled in the art. In the subject invention, images from more than one HIV-infected subject having a known prognosis may be used.

This invention also provides a method for determining the efficacy of an anti-HIV treatment in an HIV-infected subject which comprises imaging HIV-infected tissue present in the HIV-infected subject by the method of the subject invention, and comparing the image so obtained with the image of an HIV-infected subject for whom the anti-HIV treatment has a known efficacy, so as to thereby determine the efficacy of the anti-HIV treatment in the HIV-infected subject.

The image of an HIV-infected subject for whom the anti-HIV treatment has a known efficacy may be obtained according to methods well known to those skilled in the art. In the subject invention, images from more than one HIV-infected subject for whom the anti-HIV treatment has a known efficacy may be used. Anti-HIV treatment includes, by way of example, drug therapy.

The subject invention also provides a method for imaging HIV in an HIV-infected subject which comprises administering to the subject an amount of the immunoconjugate of the subject invention effective to permit determining the location of HIV present in the subject under conditions permitting the immunoconjugate to specifically bind to HIV present in the subject, and determining the location of the immunoconjugate specifically bound to HIV present in the subject after a suitable period of time, so as to thereby image HIV present in the HIV-infected subject. The subject invention further provides methods of determining the stage of an HIV infection, determining the prognosis, and determining the efficacy of an anti-HIV treatment in an HIV-infected subject using the imaging method of the subject invention.

This invention also provides a composition which comprises the immunoconjugate of the subject invention in an amount, effective to permit imaging HIV-infected tissue present in an HIV-infected subject and a pharmaceutically acceptable carrier.

This invention also provides a method for determining the HIV envelope glycoprotein burden in an HIV-infected subject which comprises administering to the subject an amount of the immunoconjugate of the subject invention effective to permit determining the amount of cell membrane-associated or viral membrane-associated HIV envelope glycoprotein present in the subject under conditions permitting the immunoconjugate to specifically bind to cell membrane-associated or viral membrane-associated HIV envelope glycoprotein in the subject, and determining the amount of the immunoconjugate specifically bound to cell membrane-associated or viral membrane-associated HIV envelope glycoprotein in the subject, so as to thereby determine the HIV envelope glycoprotein burden in the HIV-infected subject.

HIV envelope glycoprotein burden is not an absolute number, in the sense that it is not the actual number of HIV and HIV-infected cells in the HIV-infected subject. Rather, the burden merely correlates with this number. "HIV envelope glycoprotein burden" means the total cell membrane- and HIV membrane-boung HIV envelope glycoprotein in the subject. The amount of the immunoconjugate of the subject invention effective to permit determining the amount of cell membrane-associated or viral membrane-associated HIV envelope glycoprotein present in the subject must be saturating, and may be determined by methods well known to those skilled in the art. Determining the immunoconjugate specifically bound to cell membrane-associated or viral membrane-associated HIV envelope glycoprotein in the subject is accomplished according to methods well known to those skilled in the art. Such methods include, by way of example, using a gamma camera.

This invention also provides a method for determining the stage of an HIV infection in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having an HIV infection at a known stage, so as to thereby determine the stage of the HIV infection in the HIV-infected subject.

This invention also provides a method for determining the prognosis of an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having a known prognosis, so as to thereby determine the prognosis of the HIV-infected subject.

This invention also provides a method for determining the efficacy of an anti-HIV treatment in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit determining the HIV envelope glycoprotein burden of an HIV-infected subject and a pharmaceutically acceptable carrier.

This invention also provides an immunoconjugate which comprises 1) a non-peptidyl toxin and 2) a heterotetramer comprising two heavy chains and two light chains, both heavy chains being either a) IgG2 heavy chains or b) chimeric CD4-IgG2 heavy chains, and both light chains being either a) kappa light chains or b) chimeric CD4kappa light chains, with the proviso that either both heavy chains or both light chains or all four chains are CD4 chimeras, the non-peptidyl toxin being linked either to the heavy chains or to the light chains, or to all four chains. In one embodiment of the invention, the chimeric CD4-IgG2 heavy chains are encoded by the expression vector designated CD4-IgG2HC-pRcCMV (ATCC No. 75193), and the chimeric CD4-kappa light chains are encoded by the expression vector designated CD4-kLC-pRcCMV (ATCC No. 75194).

The CD4-IgG2 chimeric heterotetramer comprising heavy chains encoded by the expression vector designated CD4-IgG2HC-pRcCMV may be produced by a) cotransfecting a mammalian cell with the expression vector for producing the heavy chains of a CD4-IgG2 chimeric heterotetramer and an expression vector encoding a light chain; b) culturing the resulting cotransfected mammalian cell under conditions such that CD4-IgG2 chimeric heterotetramer is produced; and c) recovering the CD4-IgG2 chimeric heterotetramer so produced.

Methods of cotransfecting mammalian cells are well known in the art and include those discussed hereinabove. Similarly, expression vectors encoding light chains are well known to those skilled in the art.

The CD4-IgG2 chimeric heterotetramer comprising light chains encoded by the expression vector designated CD4kLC-pRcCMV may be produced by a) cotransfecting a mammalian cell with the expression vector for producing the light chains of a CD4-IgG2 chimeric heterotetramer and with an expression vector encoding an IgG2 heavy chain; b) culturing the resulting cotransfected mammalian cell under conditions such that a CD4-IgG2 chimeric hetero-tetramer is produced; and c) recovering the CD4-IgG2 chimeric heterotetramer so produced.

The CD4-IgG2 chimeric heterotetramer comprising heavy chains encoded by the expression vector designated CD4-IgG2HC-pRcCMV and light chains encoded by the expression vector designated CD4-kLC-pRcCMV may be produced by a) cotransfecting a mammalian cell with the expression vector for producing the heavy chains of a CD4-IgG2 chimeric heterotetramer and an expression vector for producing the light chains of an CD4-IgG2 chimeric heterotetramer; b)culturing the resulting cotransfected mammalian cell under conditions such that the CD4-IgG2 chimeric heterotetramer is produced; and c) recovering the CD4-IgG2 chimeric heterotetramer so produced.

The non-peptidyl toxin may be an enediyne anti-cancer antibiotic or derivative thereof. In one embodiment of the subject invention, the enediyne anti-cancer antibiotic is calicheamicin.

These toxins may be linked to the CD4-IgG2 chimeric heterotetramer by various techniques. These techniques include site-specific linkage of the toxins to the N-linked oligosaccharide side chains on the Fc portion of the CD4-IgG2 chimeric heterotetramer. Alternatively, the toxin may be linked to amino acid residues such as lysine present on both the CD4 and the IgG2 portions of the tetramer.

The non-peptidyl toxin may also be a cytotoxic radionuclide. The cytotoxic radionuclide may be an alpha-emitting isotope such as $^{225}$Ac, $^{211}$At, $^{212}$Bi, or $^{213}$B. Alternatively, the cytotoxic radionuclide may be an beta-emitting isotope such as $^{186}$Rh, $^{188}$Rh, $^{90}$y, $^{131}$I or $^{67}$Cu. Furthermore, the cytotoxic radionuclide may be emitting Auger and low energy electron, such as $^{125}$I, $^{123}$I, or $^{77}$Br.

These radionuclides may be conjugated to the CD4-IgG2 chimeric heterotetramer by a variety of techniques. These techniques include site-specific linkage to the N-glycosylation sites on the Fc portion of the tetramer. Alternatively, the radionuclides may be linked to amino acid residues such as tyrosine or lysine present on both the CD4 and the IgG2 portions of the tetramer.

This invention also provides a method of killing HIV-infected cells which comprises contacting HIV-infected cells with the immunoconjugate of the subject invention in an amount effective to kill the cells. The amount effective to kill the cells may be readily determined using methods known to those skilled in the art.

This invention also provides a method of treating an HIV-infected subject so as to reduce the population of HIV-infected cells in the subject which comprises administering to the HIV-infected subject an amount of immunoconjugate of the subject invention effective to kill HIV-infected cells and thereby reduce the population of HIV-infected cells in the HIV-infected subject. The amount of immunoconjugate effective to kill HIV-infected cells and thereby reduce the population of HIV-infected cells in the HIV-infected subject may be readily determined using methods known to those skilled in the art.

In the preferred embodiment of the subject invention, the amount of immunoconjugate administered is effective to eliminate the population of HIV-infected cells in the HIV-infected subject. The amount of immunoconjugate effective to eliminate the population of HIV-infected cells in the HIV-infected subject may be readily determined using methods known to those skilled in the art.

This invention also provides a method of treating a subject so as to reduce the likelihood of the subject's becoming infected with HIV which comprises administering to the subject the immunoconjugate of the subject invention in an amount effective to reduce the likelihood of the subject's becoming infected with HIV. The amount of immunoconjugate effective to reduce the likelihood of the subject's becoming infected with HIV may be readily determined using methods known to those skilled in the art.

This invention also provides a pharmaceutical composition which comprises the immunoconjugate of the subject invention in an amount effective to kill HIV-infected cells and thereby reduce the population of HIV-infected cells in an HIV-infected subject and a pharmaceutically acceptable carrier.

This invention also provides an immunoconjugate which comprises 1) a gamma radiation-emitting radionuclide of low to moderate cytotoxicity and 2) a heterotetramer comprising two heavy chains and two light chains, both heavy chains being either a) IgG2 heavy chains or b) chimeric CD4-IgG2 heavy chains, and both light chains being either a) kappa light chains or b) chimeric CD4kappa light chains, with the proviso that either both heavy chains or both light chains or all four chains are CD4 chimeras, the radionuclide being linked either to the heavy chains or to the light chains, or to all four chains. In one embodiment of the subject invention, the chimeric CD4-IgG2 heavy chains are encoded by the expression vector designated CD4-IgG2HC-pRcCMV (ATCC No. 75193), and the chimeric CD4-kappa light chains are encoded by the expression vector designated CD4-kLC-pRcCMV (ATCC No. 75194).

The gamma radiation-emitting radionuclide may be $^{131}$I, $^{125}$I, $^{123}$I, $^{111}$In, $^{99m}$Tc or $^{188}$Rh. These gamma radiation-emitting radionuclides may be conjugated to the CD4-IgG2 chimeric heterotetramer by a variety of techniques. These techniques include site-specific linkage to the N-glycosylation sites on the Fc portion of the tetramer, or to sulphydryl groups generated from the disulphide bonds on the tetramer. Alternatively, the radionuclides may be linked to amino acid residue such as tyrosine or lysine present on both the CD4 and IgG2 portions of the tetramer.

The imaging isotopes may include positron-emitting isotopes such as $^{86}$Y, $^{66}$Ga and 124I. They may also include paramagnetic metals such as Gadolinium which is a stable isotope.

This invention also provides a method for imaging HIV-infected tissue present in an HIV-infected subject which comprises administering to the subject an amount of the immunoconjugate of the subject invention effective to permit determining the location of HIV-infected tissue present in the subject under conditions permitting the immunoconjugate to specifically bind to HIV-infected tissue present in the subject, and determining the location of the immunoconjugate specifically bound to HIV-infected tissue present in the subject after a suitable period of time, so as to thereby image HIV-infected tissue present in the HIV-infected subject.

This invention also provides a method for determining the stage of an HIV infection in an HIV-infected subject which comprises imaging HIV-infected tissue present in the HIV-infected subject by the method of the subject invention, and comparing the image so obtained with the image of an HIV-infected subject having an HIV infection at a known stage, so as to thereby determine the stage of the HIV infection in the HIV-infected subject.

This invention also provides a method for determining the prognosis of an HIV-infected subject which comprises imaging HIV-infected tissue present in the HIV-infected subject by the method of the subject invention, and comparing the image so obtained with the image of an HIV-infected subject having a known prognosis, so as to thereby determine the prognosis of the HIV-infected subject.

This invention also provides a method for determining the efficacy of an anti-HIV treatment in an HIV-infected subject which comprises imaging HIV-infected tissue present in the HIV-infected subject by the method of the subject invention, and comparing the image so obtained with the image of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit imaging HIV-infected tissue present in an HIV-infected subject and a pharmaceutically acceptable carrier.

This invention also provides a method for determining the HIV envelope glycoprotein burden in an HIV-infected subject which comprises administering to the subject an amount of the immunoconjugate of the subject invention effective to permit determining the amount of cell membrane-associated or viral membrane-associated HIV envelope glycoprotein present in the subject under conditions permitting the immunoconjugate to specifically bind to cell membrane-associated or viral membrane-associated HIV envelope glycoprotein in the subject, and determining the amount of the immunoconjugate specifically bound to cell membrane-associated or viral membrane-associated HIV envelope glycoprotein in the subject, so as to thereby determine the HIV envelope glycoprotein burden in the HIV-infected subject.

This invention also provides a method for determining the stage of an HIV infection in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having an HIV infection at a known stage, so as to thereby determine the stage of the HIV infection in the HIV-infected subject.

This invention also provides a method for determining the prognosis of an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject having a known prognosis, so as to thereby determine the prognosis of the HIV-infected subject.

This invention also provides a method for determining the efficacy of an anti-HIV treatment in an HIV-infected subject which comprises determining the HIV envelope glycoprotein burden in the subject by the method of the subject invention, and comparing the HIV envelope glycoprotein burden so determined with the HIV envelope glycoprotein burden of an HIV-infected subject for whom the anti-HIV treatment has a known efficacy, so as to thereby determine the efficacy of the anti-HIV treatment in the HIV-infected subject.

This invention also provides a composition which comprises the immunoconjugate of the subject invention in an amount effective to permit determining the HIV envelope glycoprotein burden of an HIV-infected subject and a pharmaceutically acceptable carrier.

The methods of the subject invention for imaging and determining the HIV envelope glycoprotein burden in an entire subject may be analogously applied to individual organs in an HIV-infected subject.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

In order to facilitate understanding of the following Experimental Details, certain frequently occurring methods and terms are best described in Maniatis et al. (42).

A. Materials and Methods

1. Construction of CD4-gamma2 chimeric heavy chain gene encoding CD4-gamma2 chimeric heavy chain homodimer: The human CD4 cDNA was excised from the plasmid pSP6T4 (6) as an EcoR1/Stu1 restriction fragment. The 0.70 kilobase fragment was isolated and cloned into EcoR1/Sma1-digested M13mp18. This intermediate vector (M13mp18(CD4)) was then isolated, linearized with Pst1, purified, and treated with Bacterial Alkaline Phosphatase (BAP). The 2.0 Kb Pst1/Pst1 fragment from the plasmid pBr gamma2 containing the human gamma2 heavy chain gene (43) (containing the hinge, CH2, and CH3 exons) was isolated and cloned into the BAP-treated M13mp18/CD4 vector. Resulting recombinants were then screened for the correct orientation of the Pst1 fragment (with respect to the CD4 sequence) to obtain a vector which contains in tandem CD4(EcoR1/Stu1)—gamma2(Pst1/Pst1). To obtain a CD4-gamma2 chimeric heavy chain gene, oligonucleotide-mediated site-directed mutagenesis was performed to juxtapose the CD4 and gamma2 heavy chain DNA sequences, ligating the CD4 sequence in frame to the hinge exon. The resulting chimeric DNA molecule encodes a protein containing the V1V2 domains of CD4 followed by the hinge, CH2, and CH3 domains of gamma2 heavy chain (FIG. 1A). Mutagenesis was performed on single-stranded DNA isolated from recombinant phage from transformed TG1 cells (Amersham). Briefly, template DNA was annealed with a 34-mer oligonucleotide (5'GACACAACATTTGCGCTCGAAAGCTAGCACCACG-3') (SEQ ID NO:7) containing sequences which join the last codon encoding Phe(179) from V1V2 of CD4 to the first codon of the hinge for IgG2 (encoding Glu) (FIGS. 1A and 3). After second strand synthesis, double stranded DNA was transformed into competent TG1 cells. Isolated plaques were then grown in fresh TG1 cells and single stranded DNA was purified for DNA sequencing. All mutations were verified and confirmed by dideoxy sequencing using the Sequenase system (USB). Plaques containing the chimeric gene with the correct sequence were then grown in TG1 cells, and Rf DNA (designated CD4-IgG2-Rf) was isolated from the cells.

2. Construction of Mammalian Expression Vector encoding CD4-gamma2 chimeric heavy chain homodimer:

The CD4-gamma2 chimeric heavy chain gene was isolated from the recombinant Rf DNA following Rf linearization with EcoR1. The EcoR1 sites in the linearized DNA were filled in with the Klenow fragment of DNA polymerase I. The flush ended DNA was then ligated overnight at 15 degrees Celsius with T4 DNA ligase to a 100-fold molar excess of HindIII linkers. After heat inactivation of T4 DNA ligase for 15 minutes at 70 degrees Celsius, the HindIII-linkered DNA was extensively digested with HindIII to liberate a fragment containing the CD4-gamma2 chimeric heavy chain gene. This HindIII fragment was then purified and ligated to the expression vector pcDNA-1 (Invitrogen), which was previously digested with HindIII and BAP treated. The resulting plasmid was then transformed into MC1061/P3 cells. Plasmid DNA was isolated from recombinant clones, and verification of the presence of the HindIII insert and orientation of the insert with respect to the cytomegalovirus (CMV) promoter in the plasmid was made by restriction enzyme analysis. The resulting mammalian expression plasmid which encodes a CD4-gamma2 chimeric heavy chain homodimer is designated CD4-IgG2-pcDNA1.

3. Expression of CD4-IgG2-pcDNA1 in mammalian cells:

a. Transient expression.

Figure 6:
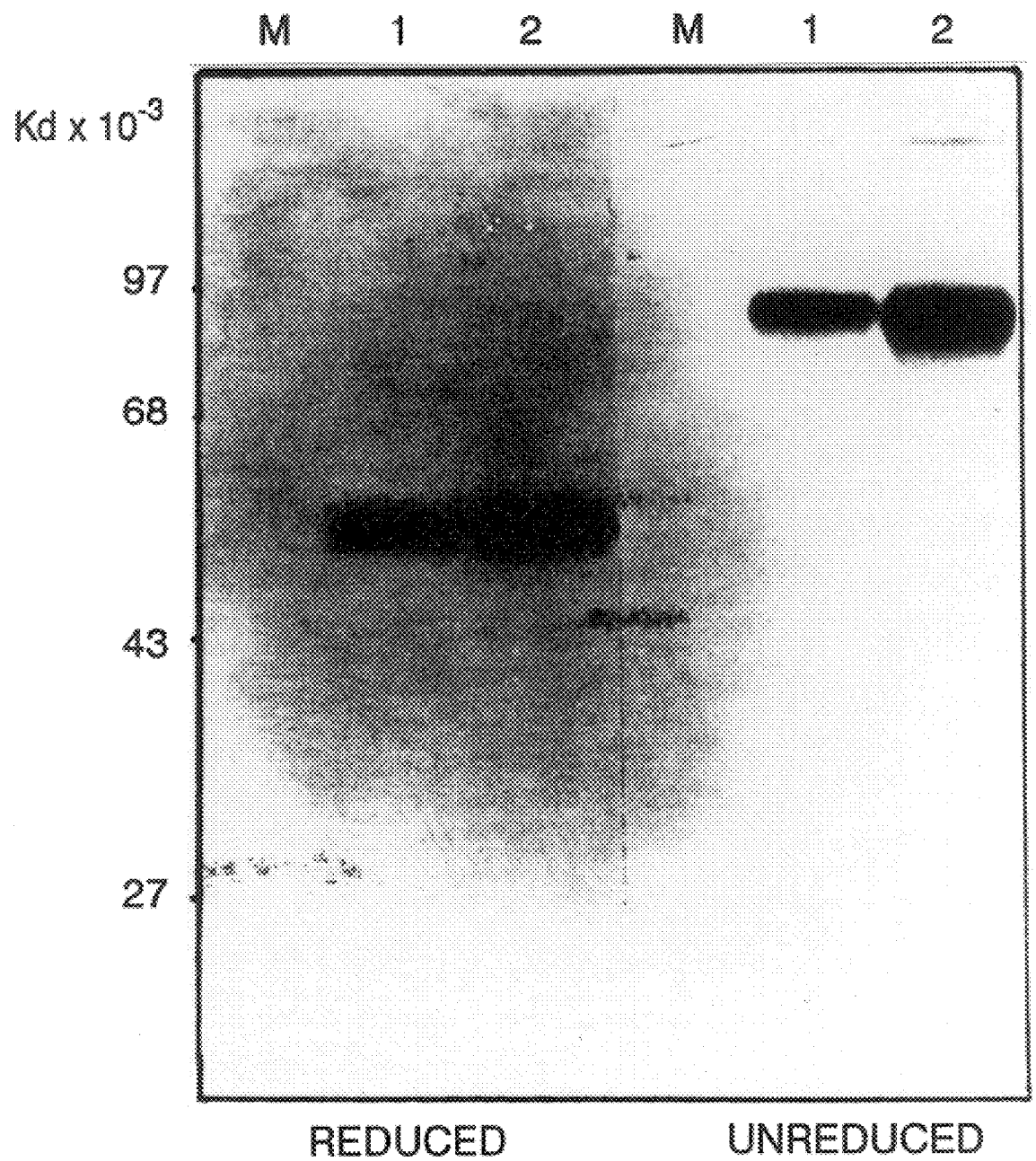
FIG. 6 Secretion of CD4-gamma2 chimeric heavy chain homodimer from transfected cells. Cos-M5 cells were mock transfected, transfected with CD4-gammal chimeric heavy chain mammalian expression vector DNA, or transfected with CD4-IgG2-pcDNA1. At 48–72 hours post-transfection, the cells were radiolabelled with $^{35}$S-methionine. Radiolabelled medium was precipitated with Protein-A sepharose beads. The precipitated proteins were analyzed by SDS-PAGE under reducing or non-reducing conditions and were visualized by fluorography. Lane M, medium from mock transfected cells; Lane 1, medium from cells transfected with CD4-gammal chimeric heavy chain mammalian expression vector DNA; Lane 2, medium from cells transfected with CD4-IgG2-pcDNA1 DNA.

CosM5 cells grown in DMEM containing 10% fetal calf serum were split to 75% confluence. On the following day, the cells were transfected for 16–20 hours with 10 micrograms of CsCl-purified plasmid CD4IgG2-pcDNA1 DNA by the standard CaPO (6) precipitation technique. After transfection, fresh medium was added to the cells. Analysis of the products synthesized 48-72 hours post-transfection was performed by radiolabelling of transfectants with $^3$S-methionine for 12-18 hours followed by precipitation of media and cell lysates using anti-CD4 antibodies or by incubation with Protein A-sepharose beads alone followed by SDS-PAGE under reducing or non-reducing conditions (FIG. 6). In addition, analysis of media and cell lysates was performed 48-72 hours post-transfection by standard Western blotting procedures.

b. Stable expression.

Dhfr-Chinese hamster ovary cells (CHO) were transfected with 20 micrograms of CsCl purified DNA in a 1000:1 molar ratio of CD4IgG2-pcDNA1:p410 (p410 is an expression plasmid containing the dhfr gene), although other ratios may also be used. Approximately 3–5 days post-transfection, cells were placed in selective medium (nucleoside-free alpha MEM containing 10 dialyzed fetal calf serum). Approximately 10–15 days post-selection, individual cell clones were picked and analyzed for stable expression of CD4-gamma2 chimeric heavy chain homodimer by several screening techniques, such as ELISA and precipitation with Protein A-sepharose beads followed by SDS-PAGE under reducing and non-reducing conditions. Clones expressing the highest levels were subjected to successive rounds of amplification of the newly introduced DNA sequences in increasing concentrations of methotrexate. Stable CHO cell lines were thus generated which secrete between 10–100 micrograms/milliliter of CD4-gamma2 chimeric heavy chain homodimer.

4. Purification of CD4-gamma2 chimeric heavy chain homodimer from CHO-conditioned media:

CHO cells secreting CD4-gamma2 chimeric heavy chain homodimer were grown to high density in roller bottles in medium containing alpha MEM with 10% IgG-free fetal calf serum. Conditioned media was collected, clarified by centrifugation, and diluted 1:1 with PBS with/or without detergent (i.e. Tween) in this and subsequent buffers. The diluted media was then applied to a 5ml column of Protein A-Sepharose fast flow previously equilibrated with PBS, at a flow rate of 60ml/hour. After extensive washing, the specifically bound material was eluted with 100 mM glycine/HCl, pH 3.5, directly into an aliquot of 1M Tris.HCl pH 8.0 to immediately neutralize the eluted fractions. The fractions were then analyzed by SDS-PAGE under reducing and non-reducing conditions followed by silver staining and pooled.

The pooled fractions were then applied to a 10 ml column of S-Sepharose fast flow previously equilibrated with 50 mM BES pH 7.0 at a flow rate of 120ml/hr. After application of the sample, a step elution gradient (consisting of the following 4 steps: 5 column volumes of 50mM BES pH 7.0, 4 column volumes of 50mM BES pH 7.0, 100mM NaCl, 6 column volumes of 50mM BES pH 7.0 225mM NaCl, followed by 8 column volumes of 50mM BES pH 7.0, 500mM NaCl) was employed for specific elution of the CD4-gamma2 chimeric heavy chain homodimer. The CD4-gamma2 chimeric heavy chain homodimer was eluted from the column in 50 mM BES pH 7.0, 500mM NaCl. The peak fractions were then pooled and concentrated to yield a final protein concentration of at least 1 mg/ml. The pooled and concentrated fractions were then applied to a 120 ml column of Sephacryl S-300HR previously equilibrated with PBS, at a flow rate of 8ml/hr. The CD4-gamma2 chimeric heavy chain homodimer fraction was specifically eluted in PBS, and concentrated to at least 1mg/ml.

5. Linking non-peptidic toxins to the CD4-gamma2 chimeric heavy chain homodimer:

Non-peptidic toxins suitable for conjugating to the CD4-gamma2 chimeric heavy chain homodimer include but are not limited to members of the enediyne anticancer antibiotics. This family of molecules includes the calicheamicins, esperamicins, and the dynemicins as well as derivatives and analogues of these molecules. These toxins are linked to the CD4-gamma2 chimeric heavy chain homodimer by various techniques. One example is the attachment of calicheamicin γ1 specifically to the N-linked oligosaccharide side chains on the Fc portion of the CD4-gamma2 chimeric heavy chain homodimers. In this case, the oligosaccharides are oxidized to aldehyes using sodium periodate. A derivative of calicheamicin γ1 is made using the linker 3-mercaptopropionyl hydrazide. This derivative is reacted with the aldehyde groups on the CD4-gamma2 chimeric heavy chain homodimer (44,45).

The toxin-linked dimer is purified by dialysis and/or by size-exclusion column chromatography.

In an alternative approach, the toxin is linked to lysines on the CD4-gamma2 chimeric heavy chain homodimer.

In this case, the toxin is prepared as an N-hydroxysuccinimide derivative and reacted directly with the dimer (44). The conjugate is purified as described above.

6. Linking cytotoxic radionuclides to the CD4-gamma2 chimeric heavy chain homodimer:

Cytotoxic radionuclides used for linking to the CD4-gamma2 chimeric heavy chain homodimer are those which emit high energy α- or β-particles. These radionuclides include, but are not limited to $^{90}$Y, $^{125}$I, $^{131}$I (β-particle emitters) and $^{212}$Bi (α-particle emitter). A variety of linking technologies are available, and have been used successfully to label monoclonal anti-tumor antibodies for therapy (39). The method used depends on the chemical nature of the radionuclide, in particular whether the isotope is metallic (e.g. $^{90}$Y, $^{212}$Bi) or nonmetallic (e.g. halides such as $^{125}$I or $^{131}$I). The CD4-gamma2 chimeric heavy chain homodimer is either labeled at specific sites, such as the N-glycosylation sites on the Fc portion of the molecule, or in an undirected approach, where the radionuclide is linked through many different sites, possibly including sites on the CD4 portion of the dimer. In either case, the dimer is labelled to a variety of specific activities to find the highest which does not cause radiolytic damage to the dimer. To assess the activity of the dimer after conjugation, and possible effects of conjugation or radiolytic damage on the properties of the dimer, a number of functional tests are performed (sections 8–13 below).

By way of example, appropriate radionuclide linking technologies include, but are not limited to the following:

For $^{125}I$ and $^{131}I$, which are readily available commercially, the radionuclide is oxidized to the I+ cation using an oxidizing agent such as chloramine T or Iodo-gen (Pierce Scientific). This oxidized halide can be attached to proteins via an electrophilic substitution reaction on an aromat such as tyrosine (39). In the case of both chloramine T and Iodo-gen, beads coated with the reagent are added to a mixture of dimer and carrier free $Na^{125}I$ or $Na^{131}I$ (a ratio of 1mCi isotope to 200 μg protein is one which has been used successfully with other proteins). Following an appropriate incubation period, the beads are removed and the radionuclide-linked dimer separated from free radionuclide by size exclusion gel chromatography.

In the case of the metallic radionuclides, $^{90}Y$ and $^{212}B$, a bifunctional chelator is used to link the isotope to the CD4-gamma2 chimeric heavy chain homodimer. The bifunctional chelator consists of a chelating agent such as diethylenetriamine pentaacetic acid (DTPA), which has been made bifunctional by, for example, the formation of a cyclic anhydride which will react with a free amino group on the protein (e.g. a lysine residue) (39). For the purposes of site-directed labeling of the dimer, a bifunctional chelator is used which attaches specifically to the N-linked oligosaccharide side chains on the Fc portion of the molecules. In this case, the oligosaccharides are oxidized to aldehyes using sodium periodate. The oxidized dimers are then run over a gel chromatography column and reacted with the amino groups of a bifunctional chelator such as glcyltyrosyllysyl-DTPA (46). A stable amine is formed by reduction using sodium borohydride. The derivatized dimer is then radiolabelled with, for example, $^{90}Y$ (a commercially available radionuclide) or $^{212}Bi$ (available via a $^{224}Ra$ generator system), at specific activities typically in the range of 1–50μCi/μg protein.

7. Linking of diagnostic/imaging radionuclides to the CD4-gamma2 chimeric heavy chain homodimer:

Radionuclides linked to the CD4-gamma2 chimeric heavy chain homodimer for diagnostic or imaging purposes include γ-radiation emitters such as $^{131}I$, $^{111}In$ and $^{99m}Tc$. A variety of linking technologies are used, such as those described in section 6 above, to link γ-radiation emitting radionuclides to the dimer.

$^{131}I$ for imaging purposes is linked to the CD4-gamma chimeric heavy chain dimer by methods such as those described in section 6 above, although lower specific activity is required for imaging than for therapeutic purposes. $^{111}In$ is a metallic radionuclide which is commercially available and is linked to the dimer using bifunctional chelators, such as those described in section 6 above for linking $^{90}Y$ or $^{212}Bi$. $^{99m}Tc$ is linked directly to the dimer using methods such as the stannous reduction technique (39). In this technique, the disulfide bonds of the dimer are reduced by mixing the dimer with a mixture of a stannous reducing agent and a phosphonic acid derivative. $^{99m}Tc$, derived from a commercially available generator, is added to the mixture and is chelated by the sulfhydryl groups on the protein, giving a stable complex.

8. Demonstration of binding of CD4-gamma2 chimeric heavy chain homodimer, or the toxin-dimer or radionuclide-dimer conjugates, to HIV gp120:

The ability of the CD4-gamma2 chimeric heavy chain homodimer, or conjugates of this dimer with non-peptidyl toxins or radionuclides, to bind gp120 is tested as follows. Medium from cells expressing CD4-gamma2 chimeric heavy chain homodimer, the purified dimer, or the toxin or radionuclide conjugates are incubated with $^{35}S$-methionine-radiolabelled HIV gp120. After incubation the complexes are adsorbed to Protein A-sepharose. Protein A-sepharose complexes are recovered by centrifugation, and the precipitates are analyzed by SDS-PAGE under reducing conditions followed by fluorography.

9. Demonstration of binding of the CD4-gamma2 chimeric heavy chain homodimer, or the toxin-dimer or radionuclide-dimer conjugates, to cells expressing the HIV envelope glycoprotein gp120/gp41:

Determination of binding of the CD4-gamma2 chimeric heavy chain homodimer or the toxin-conjugated dimer is performed by flow cytometry. Briefly, the molecules are incubated with HIV-infected cells, cells which have been engineered to stably express HIV gp120/gp41, or control cells of the same lineage which do not express gp120/gp41. Following extensive washing, the cells are incubated with an antibody which specifically reacts with the dimer, such as goat anti-(human IgG heavy and light chain). This antibody is obtained already conjugated with fluorescein isothiocyanate (FITC). Following further washing, the amount of cell-associated fluorescence is measured by flow cytometry, as a measure of the binding of the CD4-gamma2 chimeric heavy chain homodimer or toxin-dimer conjugate to the cells. To show the specificity of the interaction, the CD4-gamma2 heavy chain dimer is incubated with cells in the presence of excess sCD4 or the anti-CD4 antibody, OKT4a, which block the interaction between gp120 and CD4.

Binding of radionuclide-conjugated CD4-gamma2 chimeric heavy chain homodimer to cells expressing HIV gp120/gp41is measured by incubating the molecules with the cells, washing extensively and measuring the amount of radioactive material bound to the cell using an appropriate detection system (e.g. a liquid scintillation counter). Cell types and controls are described above.

10. Determination of FcR binding by the CD4-gamma2 chimeric heavy chain homodimer, or toxin-dimer or radionuclide-dimer conjugates:

The U937 macrophage cell line, which expresses FcγRI and FcγRII was used for these studies. In the case of the CD4-gamma2 chimeric heavy chain homodimer and the toxin-dimer conjugate, FcR binding was determined by analyzing the binding of the molecules to U937 cells using flow cytometry. The procedure for detecting bound molecules was performed as discussed in section 9 above. The binding of the dimer was compared to that of purified human IgG1 and human IgG2. The specificity of binding of the molecules to cells was determined by pre-incubating cells with monoclonal anti-FcγRI antibody, which blocks specific interactions with the high affinity Fc receptor.

Binding of radionuclide-conjugated CD4-gamma2 chimeric heavy chain homodimer to U937 cells is measured by incubating the molecules with cells, washing extensively and measuring the amount of radioactive material bound to the cell using an appropriate detection system (e.g. a scintillation counter) . Controls include radiolabelled purified human IgG1 and IgG2. The specificity of binding is determined as described above for the unconjugated and toxin-conjugated molecules.

11. Demonstration of killing of gp120/gp41-expressing cells by the toxin-conjugated and radionuclide-conjugated CD4-gamma2 chimeric heavy chain homodimer.

A variety of standard procedures are used to measure cell killing by cytotoxic CD4-gamma2 chimeric heavy chain homodimer conjugates. Several different target cells are used, including HIV-infected primary monocytes/macrophages, dendritic cells, T lymphocytes, peripheral blood mononuclear cells (PBMC), and cell lines derived from these cell types. Cells which stably or transiently express the HIV envelope glycoprotein are also used. Cells infected with primary HIV isolates, or cells expressing the envelope glycoprotein of primary isolates are used as well as those infected with or expressing the envelope glycoprotein of laboratory HIV isolates.

In brief, the cytotoxic conjugates or control proteins are incubated with HIV-infected cells, or cells engineered to express the HIV envelope glycoprotein, and the cell viability is determined at intervals afterwards. Several methods are used to determine cell viability. For example, cells are stained with trypan blue. Live cells exclude this dye, so the number of stained cells is a measure of cell death. Alternatively, a tetrazolium salt assay is used (47). In this case, the cells are incubated with a solution of the tetrazolium salt MTT (3(4,5-dimethylthiazol-2-yl)-2,5-diphenyl tetrazolium bromide). This salt is colorless until the tetrazolium ring is cleaved by dehydrogenase enzymes in viable cells, giving a colored product which can be measured by spectrophotometry. In an alternative approach, the rate of cell growth is determined by measuring the incorporation of $^3$H-thymidine into viable cells, using standard techniques.

In all these assays, a number of controls are used, including testing cells which do not express HIV-gp120/gp41, such as FcR-bearing U937 cells, and testing the reactivity of toxin-linked or cytotoxic radionuclide-linked monoclonal antibodies to antigens not present on the cells used in the test.

12. Determination of the effect of cytotoxic radionuclide-conjugated, or toxin-conjugated, CD4-gamma2 chimericheavy chain homodimer on HIV-infected cell cultures:

A number of standard assays are used to measure the effect of the CD4-gamma2 chimeric heavy chain homodimer-toxin or radionuclide conjugates on HIV cultures. To measure the effect of the conjugates on spreading of the virus in cell cultures cells of the various types described in section 11 above, are infected with HIV. Both clinical and laboratory strains are used, in separate experiments. These cells are incubated with a range of concentrations of the toxin-dimer or radionuclide-dimer conjugates for several days. Cultures are regularly diluted and fresh medium containing the conjugate is added. Spread of infection within the culture is determined by a number of procedures, such as measuring the level of p24 antigen or reverse transcriptase (RT) activity in the cell supernatant at regular intervals after initiation of the experiment. Controls in these experiments include unconjugated CD4-gamma2 chimeric heavy chain homodimer, and irrelevant monoclonal antibodies linked to the toxin or radionuclide.

Similar experiments are done to see if the conjugates can eliminate HIV-infected cells and HIV from cultures. In this case, the effect of combining the toxin or radionuclide-conjugated dimers with other drugs such as the RT inhibitor AZT is also examined. In the event that one of the drugs or drug combinations reduces the level of virus in the supernatant to below detectable levels while maintaining viable cells in the culture (measured by techniques described in section 11 above), the presence of HIV proviral DNA in the cells is examined. In this case, the polymerase chain reaction (PCR) technique is used to amplify regions of the HIV genome from cell lysates, and the amplified DNA is detected by hybridization with a probe to the appropriate DNA fragment.

13. Determination of plasma half-life of the CD4-gamma2 chimeric heavy chain homodimer, or conjugates of this molecule with toxins or radionuclides:

Determination of the plasma half-life is performed by well established techniques. Briefly, rabbits or monkeys are injected intravenously or intramuscularly with purified CD4-gamma2 chimeric heavy chain homodimer, or the toxin or radionuclide derivatives thereof. At various post-injection time points, plasma samples are taken, and the concentration of the drug in the plasma is measured by an enzyme-linked immunosorbent assay (ELISA). For example, 96-well plastic ELISA plates are coated with purified anti- (human IgG heavy and light chain) antibody. After washing, appropriate dilutions of plasma or standards containing known concentrations of the CD4-gamma2 chimeric heavy chain homodimer are added to the plate. Following incubation and washing, the dimer is detected by incubating with a mouse monoclonal anti-CD4 antibody, then with a peroxidase-linked anti-mouse IgG antibody and finally with a chromogenic peroxidase substrate measured by spectrophotometry.

14. Construction of CD4-IgG2 chimeric heavy chain expression vector and CD4-kappa chimeric light chain expression vector for production of CD4-IgG2 chimeric heterotetramers.

a. Construction of CD4-IgG2 chimeric heavy chain mammalian expression vector.

The human CD4 cDNA sequence is excised from the plasmid pSP6T4 (6) as an EcoR1/Stu1 restriction fragment. The 0.70 kilobase fragment is isolated and cloned into EcoR1/Sma1-digested M13mp18. The resulting vector (M13mp18(CD4)) is then isolated and digested with BamH1. The BamH1 sites of the M13mp18(CD4) are made flush ended with the Klenow fragment of DNA polymerase 1. After heat inactivation of the polymerase for 15 minutes at 65 degrees Celsius, the linearized M13mp18(CD4) vector is then digested with Pst1 and purified.

In order to excise a fragment containing the CH1 exon of the human gamma2 heavy chain gene, the plasmid pBr gamma2 (43) is digested with SacII, and the SacII sites are then made flush using T4 DNA polymerase. After heat inactivation of the polymerase, the fragment is then digested with Pst1. The resulting SacII(flush)-Pst1 fragment containing the CH1 exon is then purified and ligated to the M13mp18(CD4) vector described in the above paragraph. After transformation of competent TG1 cells, the resulting recombinants are screened by restriction analysis for the presence of both CD4 and CH1 sequences which contain in tandem CD4 (EcoR1/Stu1)—CH1 (SacII(flush)/Pst1). Oligonucleotide-mediated site-directed mutagenesis is then performed to juxtapose the CD4 and CH1 sequences in frame. The resulting chimeric DNA molecule contains the V1V2 domains of CD4 fused to the CH1 domain of gamma2 heavy chain. Mutagenesis is performed on single-stranded DNA isolated from recombinant phage from transformed TG1 cells (Amersham). Template DNA is annealed with a 33-mer oligonucleotide (5'-GGGCCCTTGGTGGA GGCGAAAGCTAGCACCACG-3') (SEQ ID NO:8) containing sequences which join the last codon encoding Phe (179) from V1V2 of CD4 to the first codon of the CH1 domain for gamma2 heavy chain (encoding Ala). After second strand synthesis, double stranded DNA is transformed into competent TG1 cells. Isolated plaques are then grown in fresh TG1 cells and single-stranded DNA is purified for DNA sequencing. All mutations are confirmed by dideoxy sequencing using the Sequenase system (USB). Plaques containing the chimeric genes with the correct sequence as determined by restriction analysis are then grown in TG1 cells, and the Rf DNA is isolated from the cells.

Rf DNA from the CD4-CH1 chimeric gene is then linearized by digestion with Pst1. The Pst1 linearized vector is then BAP treated and ligated to the Pst1—Pst1 DNA fragment of the plasmid pBr gamma2 containing the hinge, CH2, and CH3 exons of the human gamma2 heavy chain gene. The correct orientation of the Pst1—Pst1 fragment with respect to the chimeric CD4-CH1 fragment is then verified by restriction analysis. The resulting chimeric gene encodes a protein containing the V1V2 domains of CD4 followed by the CH1, hinge, CH2, and CH3 regions of gamma2 heavy chain (FIGS. 2A, 2B, and 4A–4H). The CD4-IgG2 chimeric heavy chain DNA molecule is isolated from the recombinant Rf DNA following Rf linearization with EcoR1. The EcoR1 sites in the linearized DNA are filled in with the Klenow fragment of DNA polymerase I. The flush ended DNA is then ligated overnight at 15 degrees Celsius with T4 DNA ligase to a 100-fold molar excess of HindIII linkers. After heat inactivation of T4 DNA ligase for 15 minutes at 70 degrees Celsius, the HindIII-linkered DNA is extensively digested with HindIII to liberate a fragment containing the CD4-IgG2 chimeric heavy chain gene. This HindIII fragment is then purified and ligated to the expression vector pcDNA-1 (Invitrogen), which was previously digested with HindIII and BAP treated. The resulting plasmid is then transformed into MC1061/P3 cells. Plasmid DNA is isolated from recombinant clones, and verification of the presence of the HindIII insert and orientation of the insert with respect to the cytomegalovirus (CMV) promoter in the plasmid is made by restriction analysis. The resulting mammalian expression plasmid which encodes a CD4-IgG2 chimeric heavy chain is designated CD4-IgG2HC-pRcCMV.

b. Construction of a CD4-kappa chimeric light chain mammalian expression vector:

The human kappa light chain constant region is excised from the plasmid pCNkappa light as an Mse1 fragment. The purified Mse1 fragment is then made flush ended using the Klenow fragment of DNA polymerase 1. M13mp18 Rf is then linearized with HincII, and the flush ended Mse1 kappa light chain fragment is ligated to M13mp18 at the flush ended HincII site in the vector. After transformation of TG1 cells, the recombinants are confirmed for the presence of the insert and the correct orientation within the vector by restriction analysis. Rf is purified from infected TG1 cells and digested with EcoR1 and Sma1. The purified vector containing the kappa light chain constant region is then ligated to the EcoR1/Stu1 fragment of the human CD4 cDNA described above. The resulting recombinants are then verified for the presence and orientation of both inserts containing in tandem CD4 (EcoR1/Stu1)—Ckappa (MseI (flush)/MseI(flush)), and single-stranded DNA is purified for oligonucleotide-mediated site directed mutagenesis. Template DNA is annealed to a 33-mer oligonucleotide (5'GATGGTGCAGCCACAGTGAAAGCTAGCACCACG-3') (SEQ ID NO:9) containing sequences which join the last codon encoding Phe(179) from V1V2 of CD4 to the first codon of the kappa light chain constant domain (encoding thr). After second strand synthesis, double-stranded DNA is transformed into competent TG1 cells, and isolated plaques are grown in fresh TG1 cells for DNA sequencing. The presence of the mutation is confirmed by dideoxy sequencing. Plaques containing chimeric genes with the correct sequence are then grown in TG1 cells, and Rf DNA is isolated from the cells. The resulting DNA molecule encodes a protein containing the V1V2 domains of CD4 followed by the constant region of kappa light chains (FIGS. 2A, 2B and 5A–5D).

The CD4-kappa chimeric light chain DNA molecule is isolated from the recombinant Rf DNA following Rf linearization with EcoR1. The EcoR1 sites in the linearized DNA are filled in with the Klenow fragment of DNA polymerase I. The flush ended DNA is then ligated overnight at 15 degrees Celsius with T4 DNA ligase to a 100-fold molar excess of HindIII linkers. After heat inactivation of T4 DNA ligase for 15 minutes at 70 degrees Celsius, the HindIII linkered DNA is extensively digested with HindIII to liberate a fragment containing the CD4-kappa chimeric light chain gene. This HindIII fragment is then purified and ligated to the expression vector pcDNA-1, which was previously digested with HindIII and BAP treated. The resulting plasmid is then transformed into MC1061/P3 cells. Plasmid DNA is isolated from recombinant clones, and verification of the presence of the HindIII insert and orientation of the insert with respect to the cytomegalovirus (CMV) promoter in the plasmid is made by restriction enzyme analysis. The resulting mammalian expression plasmid which encodes a CD4-kappa chimeric light chain is designated CD4-kLCp-RcCMV.

15. Co-expression of CD4-IgG2HC-pRcCMV and CD4-kLC-pRcCMV in mammalian cells to produce a CD4-IgG2 chimeric heterotetramer.

a. Transient expression.

CosM5 cells grown in DMEM containing 10% fetal calf serum are split to 75% confluence. On the following day, the cells are transfected for 16–20 hours with 5 micrograms of CsCl-purified CD4-IgG2HC-pRcCMV DNA and 5 micrograms of CsCl-purified CD4-kLC-pRcCMV plasmid DNA by the standard CaPO (6) precipitation technique. After transfection, fresh medium is added to the cells.

Analysis of the products synthesized 48-72 hours post-transfection is performed by radiolabelling of transfectants with $^{35}$S-methionine for 12–18 hours followed by precipitation of media and cell lysates using anti-CD4 antibodies or by incubation with Protein A-sepharose beads alone followed by SDS-PAGE under reducing or non-reducing conditions. In addition, analysis of media and cell lysates is performed 48–72 hours post-transfection by standard Western blotting procedures.

b. Stable expression.

Dhfr-Chinese hamster ovary cells (CHO) are transfected with 20 micrograms of CsCl-purified DNA in a ratio of 1000:1000:1 CD4-IgG2HC-pRcCMV:CD4-kLC-pRcCMV:p410 (p410 is an expression plasmid containing the dhfr gene), although other ratios may also be used. At approximately 3–5 days post-transfection, cells are placed in selective medium (nucleoside-free alpha MEM containing 10% dialyzed fetal calf serum) . At approximately 10–15 days post-selection, individual cell clones are picked. The clones are then analyzed for stable expression of CD4-IgG2 chimeric heterotetramers by several screening techniques, such as ELISA and precipitation with Protein A-sepharose beads followed by SDS-PAGE under reducing or non-reducing conditions. Clones expressing the highest levels are subjected to successive rounds of amplification of the newly introduced DNA sequences in increasing concentrations of methotrexate. Stable CHO cell lines are thus generated which secrete high levels of CD4-IgG2 chimeric heterotetramer.

16. Purification of CD4-IgG2 chimeric heterotetramers from CHO conditioned media:

CD4-IgG2 chimeric heterotetramers are purified using Protein A-Sepharose column chromatography. CHO cells secreting CD4-IgG2 chimeric heterotetramers are grown to high density in roller bottles in medium containing alpha MEM with 10% IgG-free fetal calf serum. Conditioned media is collected, clarified by centrifugation, and diluted 1:1 with PBS with/or without detergent (i.e. Tween) in this and subsequent buffers. The diluted media is then applied to a 5ml column of Protein A-Sepharose fast flow previously equilibrated with PBS, at a flow rate of 60ml/hour. After extensive washing, the bound material is eluted with 100 mM glycine/HCl, pH 3.5, directly into an aliquot of 1M Tris.HCl pH 8.0 to immediately neutralize the eluted fractions. Fractions are then analyzed by SDS-PAGE under reducing and non-reducing conditions followed by silver staining and pooled. Further purification involves a series of chromatographic steps, including affinity chromatography using anti-kappa light chain antibodies attached to a sepharose matrix, to separate CD4-IgG2 chimeric heterotetramers from heavy chain dimers.

17. Linking non-peptidyl toxins to the CD4-IgG2 chimeric heterotetramer:

Non-peptidyl toxins suitable for conjugating to the CD4-IgG2 chimeric heterotetramer include, but are not limited to, members of the enediyne anticancer antibiotics. This family of molecules includes calicheamicin, esperamicins, and the dynemicins, as well as derivatives and analogues of these molecules. These toxins are linked to the CD4-IgG2 chimeric heterotetramer by various techniques. One example is the attachment of calicheamicin γ1 specifically to the N-linked oligosaccharide side chains on the Fc portion of the tetramer. In this case, the oligosaccharides are oxidized to aldehyes using sodium periodate. A derivative of calicheamicin γ1 is made using the linker 3-mercaptopropionyl hydrazide. This derivative reacts with the aldehyde groups on the CD4-IgG2 chimeric heterotetramer (44, 45). The toxin-linked tetramer is purified by dialysis and/or by size-exclusion column chromatography.

In an alternative approach, the toxin is linked to lysines on the CD4-IgG2 chimeric heterotetramer. In this case, the toxin is prepared as an N-hydroxysuccinimide derivative and reacted directly with the tetramer (44). The conjugate is purified as described above.

18. Linking cytotoxic radionuclides to the CD4-IgG2 chimeric heterotetramer:

Cytotoxic radionuclides used for linking to the CD4-IgG2 chimeric heterotetramer are those which emit high energy α- or β-particles. These radionuclides include, but are not limited to $^{90}$Y, $^{125}$I, $^{131}$I (β-particle emitters) and $^{212}$Bi (α-particle emitter). A variety of linking technologies are available, and have been used successfully to label monoclonal anti-tumor antibodies for therapy (39). The method used depends on the chemical nature of the radionuclide, in particular whether the isotope is metallic (e.g. $^{90}$Y or $^{212}$Bi) or non-metallic (e.g. halides such as $^{125}$I or $^{131}$I). The CD4-IgG2 chimeric heterotetramer is either labeled at specific sites, such as the N-glycosylation sites on the Fc portion of the molecule, or in an undirected approach, where the radionuclide is linked through many different sites, possibly including sites on the CD4 portion of the tetramer. In either case, the tetramer is labelled to a variety of specific activities to find the highest which does not cause radiolytic damage to the tetramer. To assess the activity of the tetramer after conjugation, and possible effects of conjugation or radiolytic damage on the properties of the tetramer, a number of functional tests are performed (sections 8–13 below).

By way of example, appropriate radionuclide linking technologies include, but are not limited to, the following techniques. For $^{125}$I and $^{131}$I, which are readily available commercially, the radionuclide is oxidized to the I+ cation using an oxidizing agent such as chloramine T or Iodo-gen (Pierce Scientific). This oxidized halide can be attached to proteins via an electrophilic substitution reaction on an aromatic residue such as tyrosine (39). In the case of both chloramine T and Iodo-gen, beads coated with the reagent are added to a mixture of tetramer and carrier-free Na$^{125}$I or Na$^{131}$I (a ratio of 1mCi isotope to 200 μg protein is one which has been used successfully with other proteins). Following an appropriate incubation period, the beads are removed and the radionuclide-linked tetramer is separated from free radionuclide by size exclusion gel chromatography.

In the case of the metallic radionuclides $^{90}$Y and $^{212}$B, a bifunctional chelator is used to link the isotope to the CD4-IgG2 chimeric heterotetramer. The bifunctional chelator consists of a chelating agent such as diethylenetriamine pentaacetic acid (DTPA), which has been made bifunctional, for example, by the formation of a cyclic anhydride which will react with a free amino group on the protein (e.g. a lysine residue) (39). For the purposes of site-directed labeling of the tetramer, a bifunctional chelator is used which attaches specifically to the N-linked oligosaccharide side chains on the Fc portion of the molecules. In this case, the oligosaccharides are oxidized to aldehyes using sodium periodate. The oxidized tetramers are then run over a gel chromatography column and reacted with the amino groups of a bifunctional chelator such as glcyltyrosyllysyl-DTPA (46). A stable amine is formed by reduction using sodium borohydride. The derivatised tetramer is then radiolabelled with, for example, $^{90}$Y (a commercially available radionuclide) or $^{212}$Bi (available via a $^{224}$Ra generator system) , at specific activities typically in the range of 1–50μCi/μg protein.

19. Linking of diagnostic/imaging radionuclides to the CD4-IgG2 chimeric heterotetramer:

Radionuclides used for linking to the CD4-IgG2 chimeric heterotetramer for diagnostic or imaging purposes include γ-radiation emitters such as $^{131}$I, $^{111}$In and $^{99m}$Tc. A variety of linking technologies are used, such as those described in section 6 above, to link γ-radiation-emitting radionuclides to the tetramer.

$^{131}$I for imaging purposes is linked to the CD4-IgG2 chimeric heterotetramer by methods such as those described in section 6 above, although lower specific activity is required for imaging than for therapeutic purposes. $^{111}$In is a metallic radionuclide which is commercially available and is linked to the tetramer using bifunctional chelators, such as those described in section 6 above for linking $^{90}$Y or $^{212}$Bi. $^{99m}$Tc is linked directly to the tetramer using methods such as the stannous reduction technique (39). In this case the disulfide bonds of the dimer are reduced by mixing the tetramer with a mixture of a stannous reducing agent and a phosphonic acid derivative. $^{99m}$Tc, derived from a commercially available generator, is added to the mixture and is chelated by the sulfhydryl groups on the protein, giving a stable complex.

20. Demonstration of binding of CD4-IgG2 chimeric heterotetramer, or the toxin-tetramer or radionuclide-tetramer conjugates, to HIV gp120:

The ability of the CD4-IgG2 chimeric heterotetramer, or conjugates of this tetramer with non-peptidyl toxins or radionuclides, to bind gp120 is tested as follows. Medium from cells expressing CD4-IgG2 chimeric heterotetramer, the purified tetramer, or the toxin or radionuclide conjugates are incubated with $^{35}$S-methionine-radiolabelled HIV gp120. After incubation, the complexes are adsorbed to Protein A-sepharose. Protein A-sepharose complexes are recovered by centrifugation, and the precipitates are analyzed by SDS-PAGE under reducing conditions followed by fluorography.

21. Demonstration of binding of the CD4-IgG2 chimeric heterotetramer, or the toxin-tetramer or radionuclide-tetramer conjugates, to cells expressing the HIV envelope glycoprotein gp120/gp41:

Determination of binding of the CD4-IgG2 chimeric heterotetramer or the toxin-conjugated tetramer is performed by flow cytometry. Briefly, the molecules are incubated with HIV-infected cells, cells which have been engineered to stably express HIV gp120/gp41, or control cells of the same lineage which do not express gp120/gp41. Following extensive washing, the cells are incubated with an antibody which reacts with the tetramer, such as goat (anti-human IgG heavy and light chain). This antibody is obtained already conjugated with fluorescein isothiocyanate (FITC).

Following further washing, the amount of cell-associated fluorescence is measured using a flow cytometer, as a measure of the binding of the CD4-IgG2 chimeric heterotetramer, or the toxin-tetramer conjugate, to the cells. To show the specificity of this interaction, the CD4-IgG2 chimeric heterotetramer is incubated with cells in the presence of excess sCD4 or the anti-CD4 antibody, OKT4a, which blocks the interaction between gp120 and CD4.

Binding of radionuclide-linked CD4-IgG2 chimeric heterotetramer to cells expressing HIV gp120/gp41 is measured by incubating the molecules with the cells, washing extensively and measuring the amount of radioactive material bound to the cell using an appropriate detection system (e.g. a beta counter or gamma counter). Cell types and controls are as described above.

22. Determination of FcR binding by the CD4-IgG2 chimeric heterotetramer, or toxin-tetramer or radionuclide-tetramer conjugates:

The U937 macrophage cell line, which expresses FcγRI and FcγRII, was used for these studies. In the case of the CD4-IgG2 chimeric heterotetramer and the toxin-linked tetramer, FcR binding is determined by analyzing the binding of the molecules to U937 cells using flow cytometry. The procedure for detecting bound molecules is as discussed in section 21 above. The binding of the tetramer is compared to that of purified human IgG1 and human IgG2. The specificity of binding of the molecules to cells is determined by pre-incubating cells with monoclonal anti-FcγRI antibody, which blocks specific interactions with the high affinity Fc receptor.

Binding of radionuclide-conjugated CD4-IgG2 chimeric heterotetramer to U937 cells is measured by incubating the molecules with cells, washing extensively and measuring the amount of radioactive material bound to the cell using an appropriate detection system (e.g. a liquid scintillation counter). Controls include radiolabelled purified human IgG1 and IgG2. The specificity of binding is determined as described above for the unconjugated and toxin-conjugated molecules.

23. Demonstration of killing of gp120/gp41-expressing cells by the toxin-conjugated and radionuclide-conjugated CD4-IgG2 chimeric heterotetramers:

A variety of standard procedures are used to measure cell killing by cytotoxic CD4-IgG2 chimeric heterotetramer conjugates. Several different target cells are used, including HIV-infected primary monocytes/macrophages, dendritic cells and T lymphocytes, peripheral blood mononuclear cells (PBMC), and cell lines derived from these cell types. Cells which stably or transiently express the HIV envelope glycoprotein are also used. Cells infected with primary HIV isolates, or expressing the envelope glycoprotein of primary isolates are used, as well as those infected with or expressing the envelope glycoprotein of laboratory HIV isolates.

In brief, the cytotoxic conjugates or control proteins are incubated with HIV-infected cells, or cells engineered to express the HIV envelope glycoprotein, and the cell viability is determined at intervals afterwards. Several methods are used to determine cell viability. For example, cells are stained with trypan blue. Live cells exclude this dye, so the number of stained cells is a measure of cell death. Alternatively, a tetrazolium salt assay is used (47). In this case, the cells are incubated with a solution of the tetrazolium salt MTT (3(4,5-dimethylthiazol-2-yl)-2,5-diphenyl tetrazolium bromide). This salt is colorless until the tetrazolium ring is cleaved by dehydrogenase enzymes in viable cells, giving a colored product which can be measured by spectrophotometry. In an alternative approach, the rate of cell growth is determined by measuring the incorporation of $^3$H-thymidine into viable cells using standard techniques.

In all these assays, a number of controls are used, including testing of cells which do not express HIV-gp120/gp41, such as FcR-bearing U937 cells, and testing toxin or radionuclide-linked monoclonal antibodies to antigens not present on the cells used in the assay.

24. Determination of the effect of cytotoxic radionuclide-conjugated, or toxin-conjugated, CD4-IgG2 chimeric heterotetramers on HIV-infected cell cultures:

A number of standard assays are used to measure the effect of the CD4-IgG2 chimeric heterotetramer-toxin or radionuclide conjugates on HIV cultures. To measure the effect of the conjugates on spreading of the virus in cell cultures, cells of the various types described in section 23 above are infected with HIV. Both clinical and laboratory strains are used, in separate experiments. These cells are incubated with a range of concentrations of the toxin-tetramer or radionuclide-tetramer conjugates for several days. Cultures are regularly diluted and fresh medium containing the conjugate is added. Spread of infection within culture is measured by a number of procedures, such as measuring the level of p24 antigen, or reverse transcriptase (RT) activity in the cell supernatant at regular intervals after initiation of the experiment. Controls in these experiments include unconjugated CD4-IgG2 chimeric heterotetramer, and irrelevant monoclonal antibodies linked to the toxin or radionuclide.

Similar experiments are done to see if the conjugates can eliminate HIV-infected cells and HIV from cultures. In this case, the effect of combining the toxin or radionuclide-conjugated tetramers with other drugs such as the RT inhibitor AZT is also examined. In the event that one of the drugs or drug combinations reduces the level of virus in the supernatant to below detectable levels while maintaining viable cells in the culture (measured by techniques described in section 23 above), the presence of proviral HIV DNA in the cells is examined. In this case, the polymerase chain reaction (PCR) technique is used to amplify regions of the HIV genome from cell lysates, and the amplified DNA is detected by hybridization with a probe to the appropriate DNA fragment.

25. Determination of plasma half-life of the CD4-IgG2 chimeric heterotetramer, or conjugates of this molecule with toxins or radionuclides:

Determination of the plasma half-life is performed by well established techniques. Briefly, rabbits or monkeys are injected intravenously or intramuscularly with purified CD4-IgG2 chimeric heterotetramer, or the toxin or radionuclide derivatives. At various post-injection time points, plasma samples are taken, and the concentration of the drug in the plasma is measured by an enzyme-linked immunosorbent assay (ELISA). For example, 96-well plastic ELISA plates are coated with purified (anti-human IgG heavy and light chain) antibody. After washing, appropriate dilutions of plasma or standards containing known concentrations of the CD4-IgG2 tetramer are added to the plate. Following incubation and washing, the tetramer is detected by incubating with a mouse monoclonal anti-CD4 antibody, then with a peroxidase-linked anti-mouse IgG antibody and finally with a chromogenic peroxidase substrate measured by spectrophotometry.

B. Results

1. Construction, expression and purification of CD4-gamma2 chimeric heavy chain homodimer and CD4-IgG2 chimeric heterotetramer A CD4-gamma2 chimeric heavy chain gene encoding a CD4-gamma2 chimeric heavy chain homodimer was generated by ligating the leader-V1-V2 segment of the human CD4 cDNA (6) to the hinge exon of the human gamma2 heavy chain gene (43) (FIG. 1A). The resulting recombinant DNA molecule (designated CD4-IgG2-Rf) encodes the signal sequence and two amino-terminal immunoglobulin-like domains of the CD4 protein (the first 179 amino acids of mature CD4) followed by the hinge (15 amino acids), CH2 (110 amino acids), and CH3 (107 amino acids) regions of the gamma2 heavy chain protein (FIG. 3A–3F). This recombinant DNA molecule also contains two introns present within the gamma2 heavy chain gene: between the H and CH2 domains, and between the CH2 and CH3 domains. This CD4-gamma2 chimeric gene was designed to encode a CD4-gamma2 chimeric heavy chain homodimer which specifically lacks the CH1 domain of the gamma2 heavy chain. Expression of the CH1 domain without accompanying light chains prevents efficient heavy chain secretion from mammalian cells (32).

Figure 1B:
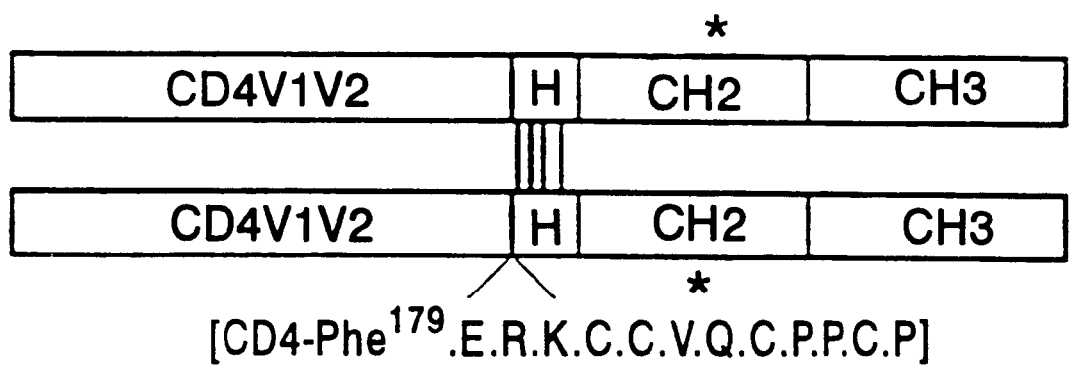

In the CD4-gamma2 chimeric heavy chain homodimer, the hinge region of one chain contains four cysteine residues, affording the potential of four interchain disulfide bonds (FIG. 1B). Similarly, naturally-occurring human IgG2 contains four interchain disulphide bonds between the gamma2 heavy chains.

The CD4-gamma2 chimeric heavy chain gene was subcloned into the mammalian expression vector pcDNA1. This vector contains the following DNA elements: the cytomegalovirus (CMV) immediate early promoter and enhancer driving transcription of the CD4-gamma2 chimeric heavy chain gene; an SV40 polyadenylation sequence; and an SV40 origin of replication which allows replication of the plasmid to high copy number in CosM5 cells. The resulting CD4-gamma2 heavy chain mammalian expression vector (designated CD4-IgG2-pcDNA1) was transfected into CosM5 cells which were then radiolabelled with $^{35}$S-methionine 48–72 hours post-transfection. The radiolabelled medium was analyzed by precipitation with Protein A-sepharose beads and SDS-PAGE followed by fluorography (FIG. 6). Under reducing conditions, a protein migrating at a relative molecular mass (Mr) of approximately 47 kilodaltons is precipitated. When the precipitated material was run on SDS-PAGE under nonreducing conditions, a protein migrating at an Mr of approximately 94 kilodaltons is observed, indicating that the CD4-gamma2 chimeric heavy chains assemble and are secreted as homodimers. In addition, these results demonstrate that the secreted CD4-gamma2 chimeric heavy chain homodimers contain an intact immunoglobulin Fc domain since they bind Protein A. Further characterization by Western blot analysis of the proteins secreted into the medium 48–72 hours post-transfection was performed using a rabbit polyclonal antiserum raised against purified soluble human CD4. Similar to the results obtained by precipitation, when the medium was run on SDS-PAGE under reducing conditions, followed by Western transfer to nitrocellulose, the major immunoreactive protein migrates at an Mr of approximately 47 kilodaltons. Under nonreducing conditions, the major immunoreactive protein migrates at an Mr of approximately 94 kilodaltons. Taken together, these results demonstrate that the CD4-gamma2 chimeric heavy chain is produced and secreted as a homodimer of the predicted molecular weight.

Figure 7:
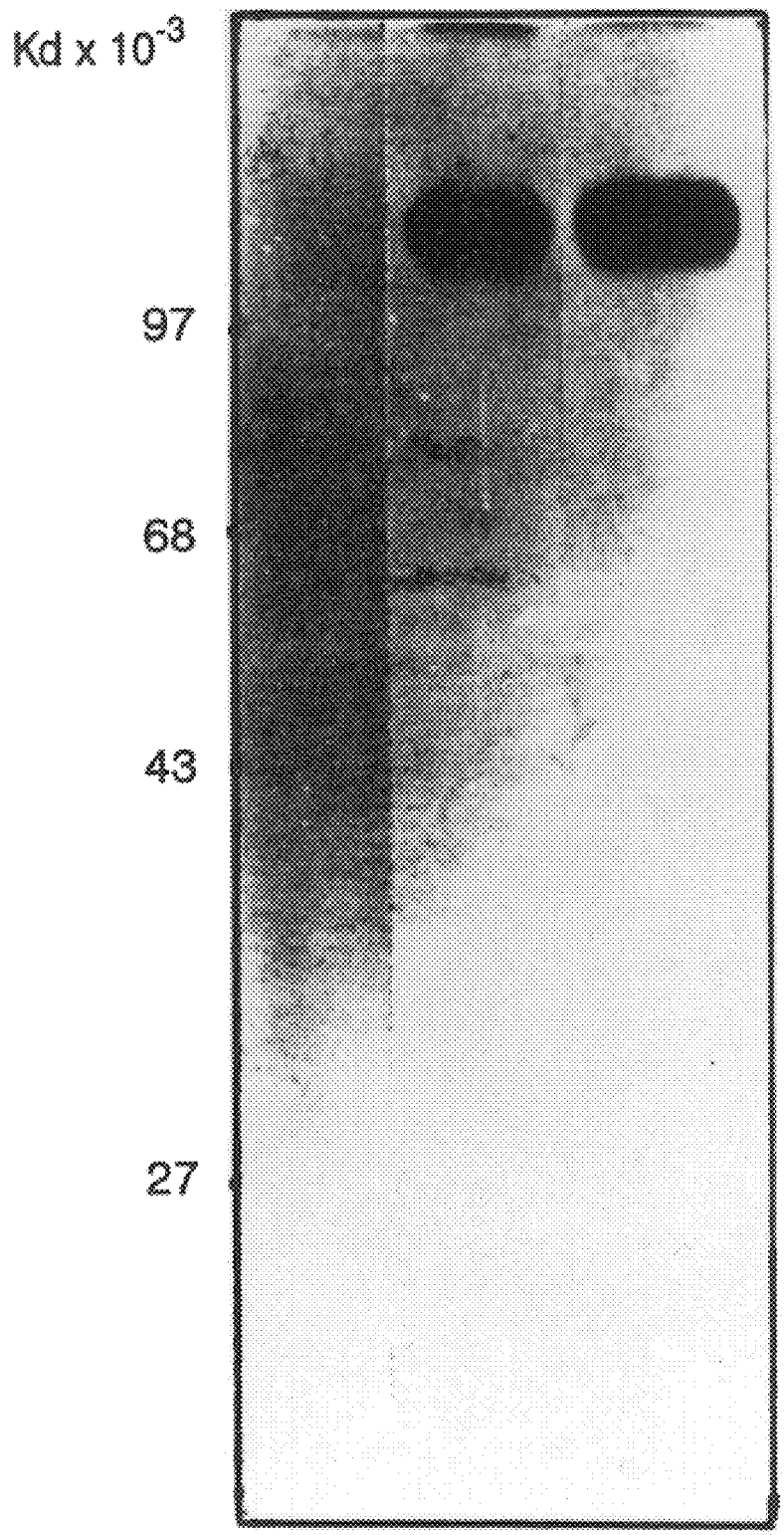
FIG. 7 Precipitation of HIV-1 gp120 with CD4-gamma2 chimeric heavy chain homodimer. Cos-M5 cells were mock transfected, transfected with CD4-gammal chimeric heavy chain mammalian expression vector DNA, or transfected with the CD4-IgG2-pcDNA1. At 48–72 hours post transfection, unlabelled aliquots of medium were incubated with an aliquot of $^{35}$S-methionine labelled gp120. The complexes were precipitated with Protein A-sepharose beads. The precipitates were then analyzed by SDS-PAGE followed by fluorography. Lane M, medium from mock transfected cells; Lane 1, medium from cells transfected with CD4-gammal chimeric heavy chain mammalian expression vector DNA; Lane 2, medium from cells transfected with CD4-IgG2-pcDNA1 DNA.

The above results demonstrate that the Fc portion of CD4-gamma2 chimeric heavy chain homodimer encoded by the constant regions of the gamma2 heavy chain gene binds Protein A. In order to determine if the CD4 portion is functionally intact, CD4-gamma2 chimeric heavy chain homodimers were assayed for their ability to bind to the HIV exterior envelope glycoprotein, gp120 (FIG. 7). Unlabelled medium from CosM5 cells transfected with CD4-IgG2-pcDNA1 DNA was incubated with $^{35}$S-methionine-labelled gp120. CD4-gamma2 chimeric heavy chain homodimer/gp120 complexes were precipitated by incubation with Protein A-sepharose beads, and the precipitates were analyzed by SDS-PAGE under reducing conditions followed by fluorography. These results demonstrate that the CD4-gamma2 chimeric heavy chain homodimer efficiently recognizes HIV gp120 and binds with high affinity. These observations, taken together with the results described in the above paragraph, demonstrate that CD4-gamma2 chimeric heavy chain homodimer contains functionally active regions of both CD4 and gamma2 heavy chain. In order to stably produce large quantities of the CD4-gamma2 chimeric heavy chain homodimers, the CD4-IgG2pcDNA1 vector was cotransfected with the plasmid p410 (encoding the enzyme dihydrofolate reductase (dhfr)) into dhfr-Chinese Hamster Ovary (CHO) cells. Approximately two weeks post-transfection, individual clones growing in nucleoside free alpha MEM and 10% dialyzed fetal calf serum (and therefore dhfr+) were isolated and analyzed for co-expression of CD4-gamma2 chimeric heavy chain homodimers by precipitation and ELISA. The highest producing cell lines were identified and subjected to stepwise increasing concentrations of methotrexate which selects for amplification of the newly introduced DNA sequences. A CHO cell line expressing approximately 10 micrograms/milliliter/day of CD4-gamma2 chimeric heavy chain homodimer was used for stable, constitutive production in roller bottles. The cells were grown to confluence in alpha MEM containing 10% IgG-free fetal calf serum. The cells were then fed every other day and two-day-old conditioned medium was used for purification of the CD4-gamma2 chimeric heavy chain homodimer. Conditioned medium was diluted 1:1 with phosphate-buffered saline (PBS) and applied to a 5ml column of Protein A-sepharose fast flow (Pharmacia) at a flow rate of 60 milliliters/hour. The column was then washed with 10 column volumes of PBS and the bound material was eluted with 100 mM glycine pH 3.5. The eluted material was collected directly into 50µl of 1M Tris.HC1 pH 8.0 to neutralize the eluant. Fractions having an OD(280) of greater than 0.1 were analyzed by SDS-PAGE followed by silver staining or Western blot analysis, and the peak fractions were pooled. A single band was specifically eluted from the Protein A-sepharose column with an Mr corresponding to the CD4-gamma2 chimeric heavy chain homodimer. Western blot analysis confirms that the eluted protein is immunoreactive with polyclonal antiserum raised against soluble human CD4. In addition, the purified protein retains the ability to bind with high affinity to $^{35}$S-methionine-labelled gp120. These results demonstrate the stable, high-level production of CD4-gamma2 chimeric heavy chain homodimers in mammalian cells, and the purification of CD4-gamma2 chimeric heavy chain homodimer which retains biological function.

Figure 8:
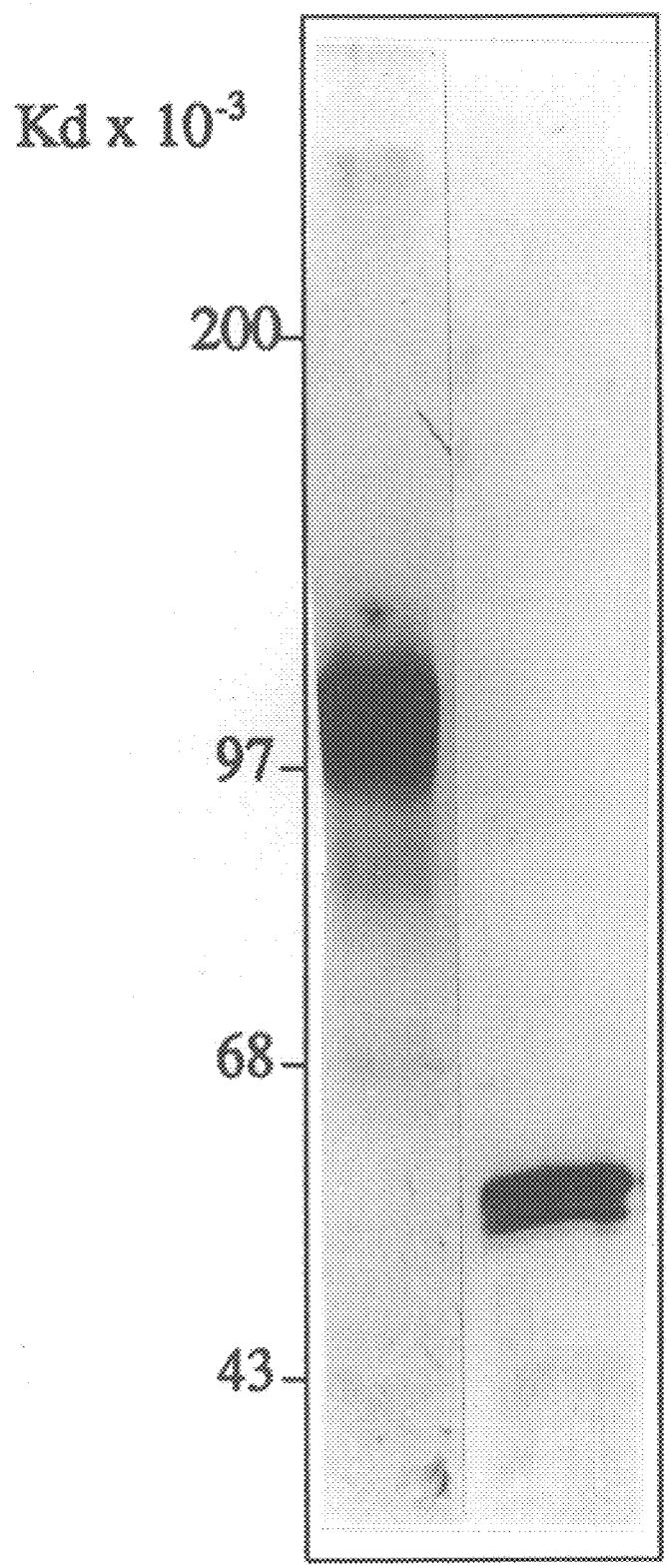
FIG. 8 Purification of CD4-gamma2 chimeric heavy chain homodimer. Stable CHO cells constitutively secreting CD4-gamma2 chimeric heavy chain homodimer were grown in roller bottles. Conditioned medium was passed over a Protein A-sepharose column and bound material was eluted from the column. The peak fractions were then pooled and passed over an S-sepharose column. After extensive washes, the CD4-gamma2 chimeric heavy chain homodimer was eluted with 50 mM BES pH 7.0, 500MM NaCl. The peak fractions were identified by SDS-PAGE followed by silver staining, pooled, and concentrated. The pooled, concentrated CD4-gamma2 chimeric heavy chain homodimer was then applied to a Sephacryl S-300HR column pre-equilibrated and run with PBS. The peak fraction corresponding to purified CD4-gamma2 chimeric heavy chain homodimer was identified by SDS-PAGE followed by silver staining. The peak fractions were then pooled and concentrated. The purified protein was then analyzed by SDS-PAGE under non-reducing and reducing conditions followed by silver staining. Lane 1: approximately 1.5 µg protein run under non-reducing conditions, Lane 2: approximately 1.5µg protein run under reducing conditions.

Further purification of CD4-gamma2 heavy chain homodimer was achieved using ion-exchange chromatography. The peak fraction from the protein A-sepharose column was applied to a 10ml S-sepharose fast flow column pre-equilibrated with 50mM BES pH 7.0, at a flow rate of 120ml/hr. After application of the sample, the column was extensively washed with 50mM BES pH 7.0 with increasing salt concentration (see Materials and Methods). CD4-gamma2 heavy chain homodimer was specifically eluted from the column in 50mM BES pH 7.0 containing 500mM NaCl. Following the ion exchange chromatography, the peak fractions containing the CD4-gamma2 chimeric heavy chain homodimer were unexpectedly still impure. Therefore, the peak fractions from the S-sepharose column were pooled, concentrated and applied to a 120ml Sephacryl S-300HR column pre-equilibrated with PBS and run at a flow rate of 8 ml per hour. The peak fractions of purified CD4-gamma2 heavy chain homodimer were analyzed by SDS-PAGE and silver staining under non-reducing conditions, and the purified fractions were pooled and analyzed by SDS-PAGE followed by silver staining under non-reducing conditions (FIG. 8, lane 1) , or reducing conditions (FIG. 8, lane 2).

Figure 2A:
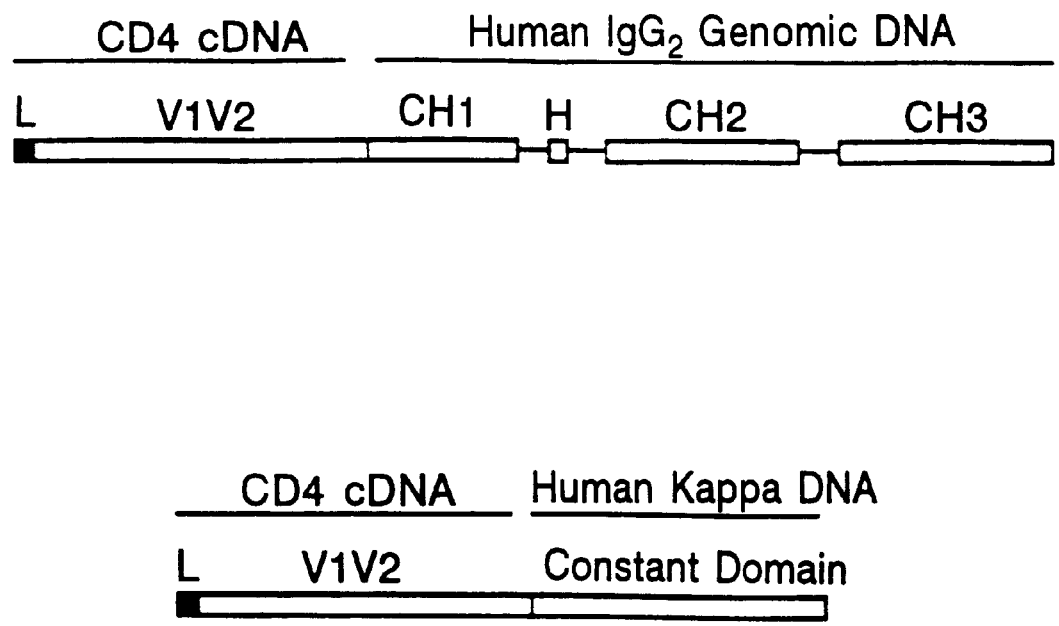
FIG. 2A–2B) Domain structure of chimeric genes used to express CD4-IgG2 chimeric heterotetramer. Top, CD4-gamma2 chimeric heavy chain gene; Bottom, CD4-kappa chimeric light chain gene. B) Protein structure of CD4-IgG2 chimeric heterotetramer. Abbreviations: CH1-CH2CH3, first, second and third constant regions of human gamma2 heavy chain; C-kappa, constant region of human kappa light chain; *, predicted N-linked glycosylation sites on CH2 domain (residues 355–357).
Figure 2B:
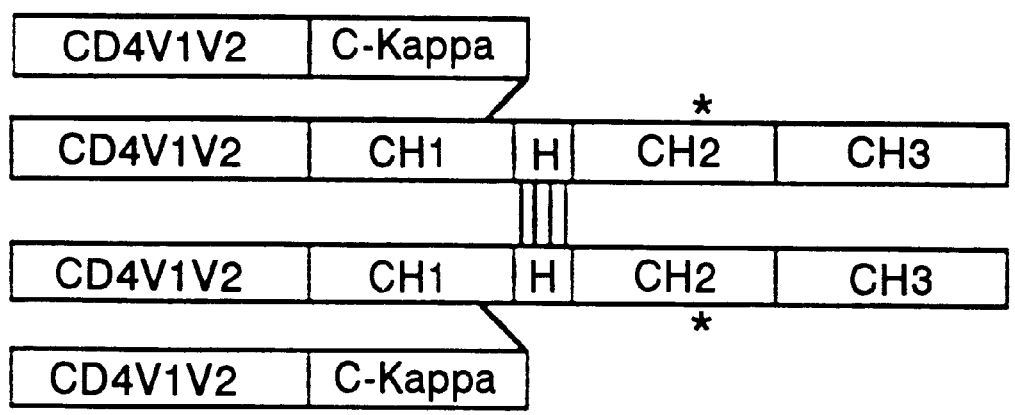
Figure 10A:
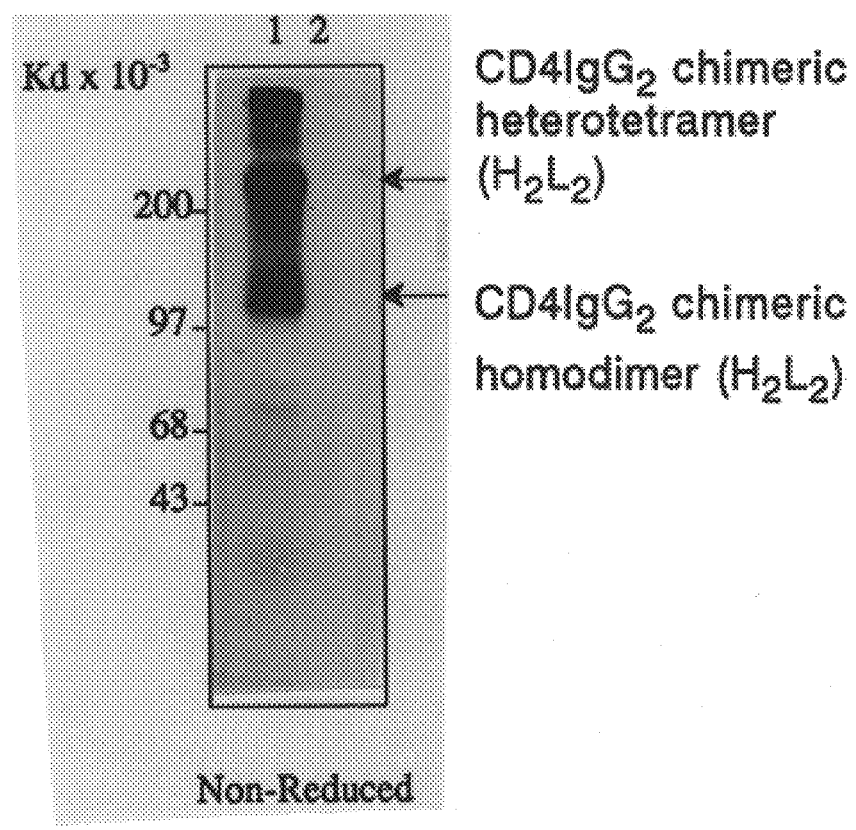
FIG. 10A–10B Secretion of CD4-IgG2 chimeric heterotetramer from stably transfected cells. CHO cells stably expressing both CD4-IgG2 chimeric heavy chains and CD4kappa chimeric light chains were radiolabelled with $^{35}$S-methionine and cysteine. Radiolabelled medium was precipitated with Protein-A sepharose beads. (A) The precipitated proteins were analyzed by SDS-PAGE under non-reducing conditions, and were visualized by fluorography. Lane 1: medium from cells stably expressing both the CD4-IgG2 chimeric heavy chains, and CD4-kappa chimeric light chains; Lane 2: medium from untransfected CHO cells. (B) An identical sample to that run in lane 1 from (A) was run on SDS-PAGE under non-reducing conditions. The lane from this SDS-PAGE gel was excised and the proteins reduced by incubation of the gel slice for 45 minutes at 4° C. in equilibration buffer (62.5mM TrisHCl pH 6.8, 2.3% SDS 5% β-mercaptoethanol, 10% glycerol). After incubation of the gel slice under reducing conditions, the proteins contained within the gel were analyzed by SDS-PAGE and visualized by fluorography.
Figure 10B:
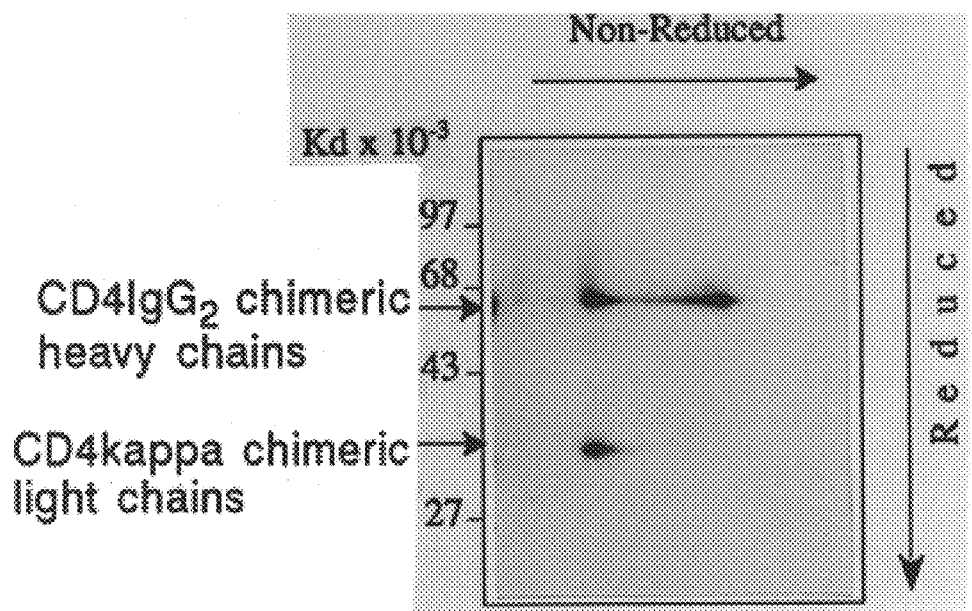

A CD4-IgG2HC chimeric heavy chain gene encoding a CD4-IgG2 chimeric heavy chain was generated by ligating the leader-V1-V2 segment of the human CD4 cDNA to the CH1 exon of the human IgG2 heavy chain gene (FIG. 2A). In addition a CD4-kappa chimeric light chain gene encoding a CD4-kappa light chain was generated by ligating the leader-V1-V2 segment of the human CD4 cDNA to the constant domain of the kappa light chain gene (FIG. 2A). These CD4-IgG2 chimeric heavy chain genes and CD4kappa chimeric light chain genes were designed to encode a CD4-IgG2 chimeric heterotetramer, in which the CD4-IgG2 heavy chain contains a CH1 domain for efficient association with kappa light chains. Both the CD4-IgG2 chimeric heavy chain and the CD4-kappa chimeric light chain genes were subcloned into the mammalian expression vectors pRcCMV or pPPI-2. Both vectors contain the cytomegalovirus immediate early promoter and enhancer driving transcription of the chimeric genes. In the vector pRcCMV, a second transcriptional cassette which contains the RSV promoter and enhancer is used to direct the transcription of the neomycin resistance gene. In pPPI-2, a second transcriptional cassette which contains the β-globin promoter directs the transcription of the dhfr gene (see supra). In order to stably produce large quantities of the CD4-IgG2 chimeric heterotetramer, the CD4-IgG2 chimeric heavy chain expression vector and the CD4-kappa chimeric light chain expression vector were transfected simultaneously (typically the CD4-IgG2 chimeric heavy chain gene cloned in pRcCMV was used, and CD4-kappa chimeric light chain gene cloned in pPPI-2 was used in a ratio of 1:1). Approximately two weeks post-transfection, individual clones growing in nucleoside-free alpha MEM containing 1 mg/ml G418 and 10% dialyzed fetal calf serum were isolated and analyzed for co-expression of both CD4-IgG2 chimeric heavy chains and CD4-kappa chimeric light chains by immunoprecipitation and ELISA. FIG. 10 demonstrates one clone which was selected and analyzed for the expression of both CD4-IgG2 chimeric heavy chains and CD4-kappa chimeric light chains. The CHO cell line or the untransfected parental CHO cell line were radiolabelled with $^{35}$S-methionine and $^{35}$S-cysteine for 16 hours. The radiolabelled medium was analyzed by precipitation with Protein A-sepharose beads and SDS-PAGE under non-reducing conditions followed by fluorography (FIG. 10A). Under non-reducing conditions 2 proteins migrating at relative molecular masses of approximately 140 kilodaltons and 210 kilodaltons are precipitated. When the precipitated material was run on SDS-PAGE under reducing conditions, 2 proteins migrating at relative molecular masses of 69 kilodaltons and 35 kilodaltons were observed, which are consistent with the relative predicted molecular masses of the CD4-IgG2 chimeric heavy chains, and CD4-kappa chimeric light chains, respectively (data not shown). Further characterization has shown that the protein migrating at 210 kilodaltons on SDS-PAGE under non-reducing conditions contains both CD4-IgG2 chimeric heavy chains and CD4kappa chimeric light chains which are covalently associated, while the protein migrating at 140 kilodaltons on SDS-PAGE under non-reducing conditions contains only CD4-IgG2 chimeric heavy chains (FIG. 10B) . These data are consistent with the predicted molecular weight of the 210 kilodalton protein having 2 CD4-IgG2 chimeric heavy chains and 2 CD4-kappa chimeric light chains, covalently associated to form a molecule with the structure $H_2L_2$ (H=heavy chain, L=light chain). Furthermore, the 140 kilodalton protein seen on SDS-PAGE under non-reducing conditions is consistent with the predicted molecular weight of a CD4-IgG2 chimeric homodimer having the structure $H_2$. Taken together, these results indicate that a CHO cell line which expresses both CD4-IgG2 chimeric heavy chains and CD4-kappa chimeric light chains is able to efficiently assemble and secrete CD4-IgG2 chimeric heterotetramers.

The cell lines producing the largest quantities of the CD4-IgG2 chimeric heterotetramer were identified and subjected to step-wise increasing concentrations of methotrexate which selects for amplification of the newly introduced DNA sequences. A CHO cell line expressing approximately 10 micrograms/milliliter/day of CD4-IgG2 chimeric heterotetramer was used for stable, constitutive production in roller bottles. Production of protein and purification on Protein A-Sepharose fast flow was similar to that described above for the CD4-gamma2 dimer and yielded protein which was greater than 90% pure CD4-IgG2 chimeric heterotetramer when analyzed by polyacrylamide gel electrophoresis under reducing and non-reducing conditions followed by silver staining (not shown).

Western blot analysis confirmed that the purified CD4-IgG2 chimeric heterotetramer is immunoreactive with polyclonal antiserum raised against soluble human CD4. In addition, the purified protein retains the ability to bind with high affinity to $^{35}$S-methionine-labelled gp120 (not shown). These results demonstrate the stable, high-level production of CD4-IgG2 chimeric heavy chain heterotetramer in mammalian cells, and the purification of CD4-IgG2 chimeric heterotetramer which retains biological function.

2. Binding of CD4-gamma2 chimeric heavy chain homodimer and CD4-Ig2 heterotetramer to cells expressing the HIV-1 envelope glycoprotein and lack of binding to U937 cells expressing Fc receptors By flow cytometry analysis (not shown) it was found that both the CD4-gammal chimeric heavy chain homodimer and the CD4-IgG2 heterotetramer bound to cells expressing the HIV-1 envelope glycoprotein.

Figure 9:
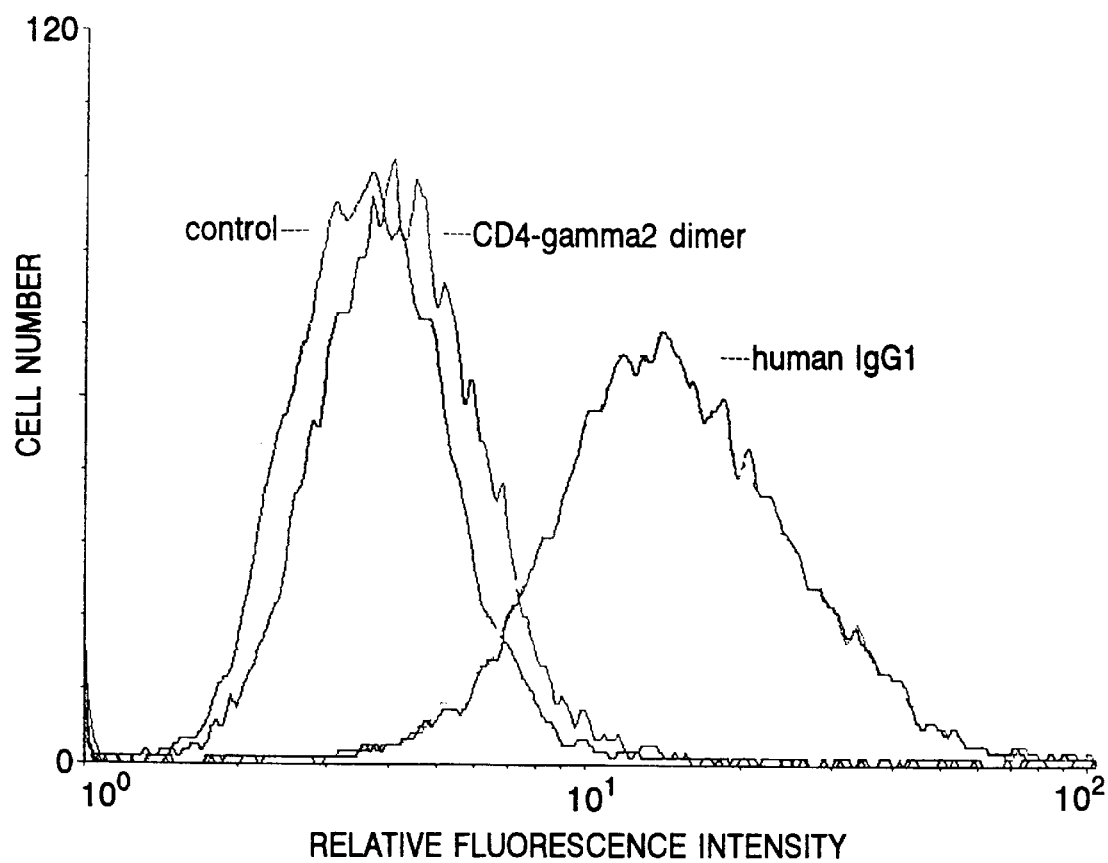
FIG. 9 Flow cytometric analysis of the binding of purified CD4-gamma2 chimeric heavy chain homodimer and human immunoglobulin gamma 1 to FcR-bearing U937 cells. U937 cells were incubated with 1 µg/ml human IgG1 or 1µg/ml CD4-gamma2 dimer for 2 hours at 4° C., washed extensively and incubated with fluorescein isothiocyanate-labelled goat anti-(human IgG heavy and light chain) antibody. Following washing, the fluorescence was analyzed on a Becton-Dickinson FacScan flow cytometer. The control peak indicates fluorescence of cells incubated with the FITC-labelled antibody only.

The purified CD4-gamma2 chimeric heavy chain homodimer did not bind significantly to U937 cells, in contrast to human IgG1 which bound well to these cells (FIG. 9).

Very similar results were obtained using the purified CD4-IgG2 heterotetramer (not shown). Human IgG2 exhibited minimal binding to U937 cells, as expected (result not shown). The specificity of binding of human IgG1 to FcγRI was demonstrated by pre-incubating the U937 cells with a monoclonal anti-human FcγRI antibody. Following this treatment, binding of IgG1 to the cells was minimal (result not shown). These results demonstrate that the CD4-gamma2 chimeric heavy chain homodimer and the CD4-IgG2 chimeric heterotetramer have minimal or no binding to FcγRI, the high affinity Fc receptor, or to FcγRII.

3. Pharmacokinetics of the CD4-gamma2 chimeric heavy chain homodimer and CD4-IgG2 chimeric heterotetramer in rabbits Samples (0.2–0.25mg) of soluble CD4, the purified homodimer or purified heterotetramer were injected into the ear veins of 5 replicate New Zealand White rabbits and blood samples collected from the opposite ear vein artery before injection and at pre-determined intervals following injection. The concentrations of the CD4-gamma2 chimeric heavy chain homodimer or CD4-IgG2 chimeric heterotetramer were determined by enzyme-linked immunosorbent assay of the plasma samples. α and β half-lives were calculated using a two compartment model (PCNONLIN version 4; SCI Software, Lexington, Kentucky).

The following results were obtained:
sCD4:
  α half-life: 7.6 minutes
  β half-life: 16.8 minutes
CD4-gamma2 chimeric heavy chain homodimer:
  α half-life: 3.4 hours
  β half-life: 30.0 hours
CD4-IgG2 chimeric heterotetramer:
  α half-life: 1.3 hours
  β half-life: 26.4 hours These values are similar to those found in other studies of sCD4 and CD4-immunglobulin constructs (28). Based on previous studies, it is likely that the terminal (β) half-life in humans will be greater than that in rabbits (28). These results indicate that the CD4-gamma2 chimeric heavy chain homodimer and the CD4-IgG2 chimeric heterotetramer have much longer terminal half lives than that of sCD4, and as a result would be appropriate candidates for making immunoconjugates suitable for killing HIV-infected cells or detecting these cells in vivo.

4 Conjugation of radioiodine to CD4-gamma2 or CD4-IgG2:

Both CD4-gamma2 and CD4-IgG2 have been radioiodinated successfully, retaining the ability to bind HIV-1 gp120 or cells expressing HIV-1 gp120/gp41. For example, CD4-gamma2 has been conjugated with $^{131}$I by the the iodogen procedure. CD4-gamma2 and CD4-IgG2 have been conjugated with $^{125}$I by the chloramine T procedure.

5. Binding of radio-iodinated CD4-gamma2 and CD4-IgG2 to HIV-1 gp120:

We used a modified ELISA method to determine 50% maximal binding (EC$_{50}$) of radiolabeled CD4-gamma2 and CD4-IgG2, in comparison with unlabeled proteins, to gp120 from the laboratory-adapted strain HIV-1$_{LAI}$ and the primary isolate HIV-1$_{JR-FL}$. The EC$_{50}$ value is a reasonable approximation of the dissociation constant (Kd). Briefly, recombinant gp120 (Progenics) was captured onto an ELISA plate and a range of concentrations of CD4-gamma2, CD4-IgG2, $^{125}$I-CD4-gamma2 or $^{125}$I-CD4-IgG2 were added. Following a 1 hour incubation at 37° C., the amount of bound protein was measured by immunoassay, and the concentration of each CD4-based molecule giving 50% of maximal binding (EC$_{50}$) was determined.

As shown in Table 1, there was no significant difference between the EC50 values obtained using the radioiodinated proteins and those obtained using the unlabelled proteins. In the case of the radioimmunoconjugates, similar EC$_{50}$ values were obtained when bound protein was determined by gamma counting rather than by ELISA.

TABLE 1

Binding affinity of radioiodinated and unlabeled CD4-based molecules to HIV-1$_{LAI}$ gp120 using an ELISA assay.

| Molecule | EC$_{50}$ (nM) - gp120 | |
|---|---|---|
| | HIV-1$_{LAI}$ | HIV-1$_{JR-FL}$ |
| CD4-gamma2 | 2.02 | 1.90 |
| $^{125}$I-CD4-gamma2 | 2.16 | 3.69 |
| CD4-IgG2 | 1.47 | 1.27 |
| $^{125}$I-CD4-IgG2 | 1.05 | 2.36 |

These results demonstrate that the radioiodinated CD4-gamma2 and CD4-IgG2 proteins bind with high affinity to HIV-1 gp120 from a laboratory-adapted strain and a primary isolate of the virus.

Figure 11:
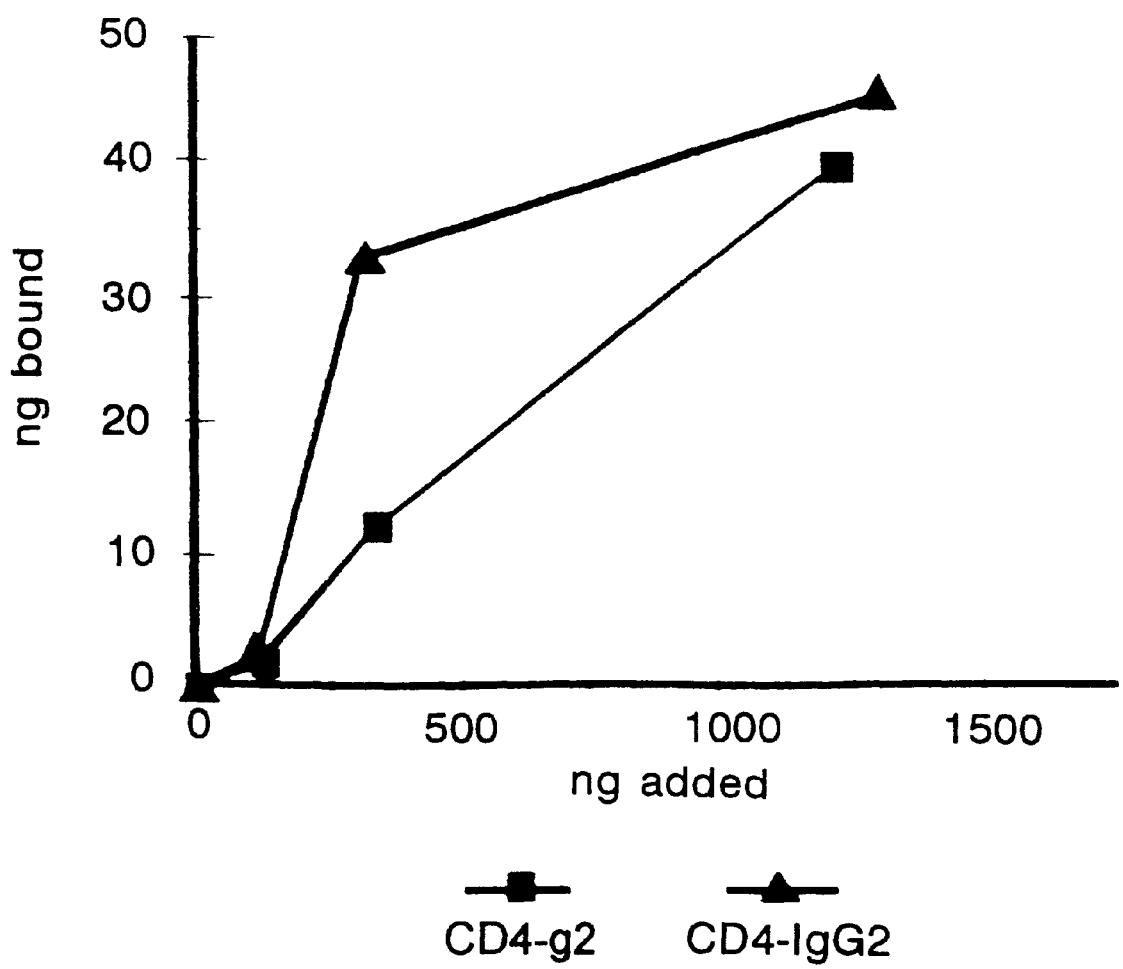
FIG. 11: Binding of $^{125}$I-CD4-gamma2 and $^{125}$I-CD4-IgG2 to HIV-1$_{LAI}$-infected H9 cells.

6. Binding to cells expressing gp120/gp41:

The binding specificity of radioiodinated CD4-gamma2 and CD4-IgG2 molecules to HIV-1$_{LAI}$-infected H9 cells, and control uninfected cells was tested at 0° C. $^{125}$I-CD4-gamma2 and $^{125}$-CD4-IgG2 bound specifically to HIV-1$_{LAI}$ infected H9 cells (FIG. 11). In addition, $^{125}$I-CD4-IgG2 bound more avidly than $^{125}$I-CD4- gamma2 to HIV-1 infected cells.

7. Measurement of the binding affinity of radioiodinated CD4-gamma2 and CD4-IgG2 to cells expressing gp120/gp41 from a laboratory-adapted strain and a primary isolate of HIV-1:

We then investigated the binding affinity of the radioimmunoconjugates to recombinant vaccinia virus-infected HeLa cells expressing gp120/gp41 from HIV-1$_{LAI}$ and HIV-1$_{JR-FL}$. The binding affinity was determined by incubating cells with various concentrations of $^{125}$I-labeled CD4-gamma2 or $^{125}$I-CD4-IgG2 (0.3–500 nM) for 45 minutes at 25° C. The fraction of labeled molecule bound was determined by gamma counting. A saturation plot of bound versus free $^{125}$I-labeled protein was used to determine the calculated EC$_{50}$ value (50% maximal binding). The results are summarized in Table 2:

TABLE 2

Binding affinity (EC$_{50}$) of radioiodinated CD4-based molecules to cells expressing gp120/gp41 from HIV-1$_{LAI}$ and HIV-1$_{JR-FL}$

| Molecule | EC$_{50}$ (nM) - gp120/gp41 | |
|---|---|---|
| | HIV-1$_{LAI}$ | HIV-1$_{JR-FL}$ |
| $^{125}$I-CD4-gamma2 | 24.51 | 36.37 |
| $^{125}$I-CD4-IgG2 | 18.97 | 12.84 |

These results demonstrate that both CD4-gamma2 and CD4-IgG2 proteins bind with affinity in the 10–40 nM range to cells expressing HIV-1 gp120/gp41 from a laboratory-adapted strain and a primary isolate of HIV-1.

8. Binding to virions:

The binding of radiolabelled CD4-gamma2 and CD4-IgG2 to intact HIV-1$_{LAI}$ virions was determined as follows. Plastic culture tubes (Luckam tubes, UK), were coated with a purified anti-HIV-1 human IgG and blocked with BSA.

The radioiodinated proteins were mixed with culture supernatant containing HIV-1$_{LAI}$ virions, or control virion-free supernatant. Following overnight incubation at 4° C., the cells were washed three times and the tubes gamma counted. Specific binding to the virions was demonstrated.

These results demonstrate that CD4- gamma2 and CD4-IgG2 have suitable properties for use as in vivo imaging agents, in which case they would be conjugated to a gamma-emitting nuclide and used to detect HIV-1 infected cells or virions in vivo. Moreover, CD4- gamma2 and CD4-IgG2 have suitable properties for use as therapeutic agents, in which case they would be conjugated to cytotoxic radionuclides or drugs and used to kill HIV-1 infected cells and reduce the viral load in vivo.

C: Example: immaging HIV-infected cells in an HIV-infected patient using an $^{131}$I-radiolabeled CD4-gamma2 chimeric heavy chain homodimer Prior to and during administration of the $^{131}$I-radiolabeled CD4-gamma2 chimeric homodimer, the patient is treated with non-radioactive iodine to prevent uptake of $^{131}$I by the thyroid. The CD4-gamma2 chimeric homodimer is labeled with $^{131}$I at a specific activity of 1–5mCi/mg using the chloramine T method, and radiolabeled protein separated from free radioiodine by size exclusion chromatography or other appropriate technique. The labeled protein is mixed with unlabeled protein as necessary to obtain the desired dose level. The $^{131}$I-radiolabeled CD4-gamma2 chimeric heavy chain homodimer is injected intravenously at an appropriate dose level, for example in the range of 1–20mg/patient, with a final activity in the range of 1–5mCi/patient.

Localization of the radiolabeled molecule in vivo is performed using a gamma camera at appropriate time intervals after injection, for example daily for the first 3 days following injection. Both single organ and whole body imaging is done to determine the distribution of HIV and HIV-infected cells in addition to the total viral burden.

REFERENCES

1. Klatzmann, D. R., et al., Immunodeficiency Reviews 2, 43–66 (1990).

2. Macatonia, R. L., et al., Immunology 71, 38–45 (1990).

3. Langhoff, E., et al., Proc. Natl. Acad. Sci. USA 88, 7998–8002 (1991).

4. Lasky, L. A., et al., Cell 50, 975–985 (1987).

5. Maddon, P. J., et al., Cell 47, 333–348 (1986).

6. Maddon, P. J., et al., Cell 42, 93–104 (1985).

7. Wain-Hobson, D., et al., Cell 40, 9–17 (1985).

8. Maddon, P. J., et al., Proc. Natl. Acad. Sci. U.S.A., 84, 9155–9159 (1987).

9. Richardson, N. E., et al., Proc. Natl. Acad. Sci. U.S.A. 85, 6102–6106 (1988).

10. Chao, B. H., et al., J. Biol. Chem. 264, 5812–5817 (1989).

11. Arthos, J., et al., Cell 57, 469–481 (1989).

12. Wang, J., et al., Nature 348, 411–418 (1990).

13. Ryu, S-E., et al., Nature 348, 419–426 (1990).

14. Maddon, P. J., et al., PCT W088/01304 (1988).

15. Moore, J. P., et al., Science 250, 1139–1142 (1990).

16. Schooley, R. T., et al., Ann. Internal Med. 112, 247–253 (1990).

17. Kahn, J. O., et al., Ann. Internal Med. 112, 254–261 (1990).

18. Daar, E. S., et al., Proc. Natl. Acad. Sci. U.S.A. 87, 6574–6578 (1990).

19. Till, M., et al., Science 242, 1166–1168 (1988).

20. Chaudhary, V. K., et al., Nature 335, 369–372 (1988).

21. Moore, J. P., et al., J. Virol. 66, 235–243 (1992).

22. Ashorn, P., et al., Proc. Natl. Acad. Sci. USA 87, 8889–8893 (1990).

23. Aullo, P., et al., EMBO Journal 11, 575–583 (1992).

24. Pastan, I. and Fitzgerald, D., Science 254, 1173–1177 (1991).

25. Boss, M. A., et al., U.S. Pat. No. 4,816,397 (1989).

26. Cabilly S., et al., U.S. Pat. No. 4,816,567 (1989).

27. Morrison, S. L., et al., Proc. Natl. Acad. Sci. 81, 6851–6855 (1984).

28. Capon, D. J., et al., Nature 337, 525–531 (1989).

29. Byrn, R. A., et al., Nature 344, 667–670 (1990).

30. Berger, E. A., et al., PCT W090/01035 (1990).

31. Seed, B., PCT W089/06690 (1989).

32. Hendershot, L., et al., J. Cell Biol. 104, 761–767 (1987).

33. Gartner, S., et al., Science 233, 215–219 (1986).

34. Traunecker, A., et al., Nature 339, 68–70 (1989).

35. Pound, J. D., and Walker, M. R., In: The Human IgG Subclasses, Ed. F. Shakib, Pergamon Press, Oxford, UK. pp.111–133 (1990).

36. Capon, D. J. and Gregory, T. J., PCT W089/02922 (1989).

37. Jarman, M., Nature 349, 566–567 (1991).

38. Nicolaou, K. C., et al., Science 256, 1172–1178 (1992).

39. Magerstadt, M., Antibody Conjugates and Malignant Disease. CRC Press, Boca Raton, Fla. (1991).

40. Okayama, H., Mol. Cell. Biol. 3, 280 (1983).

41. Remington's Pharmaceutical Science, 16th Ed., Mack Ed. (1980).

42. Maniatis, T., et al., Molecular Cloning, Vol. 1–3 (1990).

43. Oi, V. T. and Morrison, S. L., Biotechnology 4, 214–223 (1986).

44. Siegel, M. M., et al., Anal. Chem. 63, 2470–2481 (1991).

45. Lee, M.D., et al., Acc. Chem. Res. 24, 235–243 (1991).

46. Rodwell, J. D., et al., Proc. Natl. Acad. Sci. USA 83, 2632–2636 (1986).

47. Mosmann, T., J. Immunol. Methods 65, 55–63 (1983).

49. Scheinberg, D. A., et al., Science, Vol. 215, 1511–1513 (1982).

What is claimed is:

1. An immunoconjugate which consists of 1) a cytotoxic radionuclide and 2) a heterotetramer comprising two heavy chains and two light chains, both heavy chains being chimeric CD4-IgG2 heavy chains encoded by the expression vector designated CD4-IgG2HC-pRcCMV (ATCC No. 75193), and both light chains being chimeric CD4-kappa light chains encoded by the expression vector designated CD4-kLC-pRcCMV (ATCC No. 75194), the cytotoxic radionuclide being linked either to the heavy chains or to the light chains, or to all four chains directly or using a bifunctional chelator.

2. A composition which comprises the immunoconjugate of claim 1 and an acceptable carrier.

3. The immunoconjugate of claim 1, wherein the cytotoxic radionuclide is an alpha-emitting isotope.

4. The immunoconjugate of claim 3, wherein the alpha-emitting isotope is $^{225}$Ac, $^{211}$At, $^{212}$Bi, or $^{213}$Bi.

5. The immunoconjugate of claim 3, wherein the cytotoxic radionuclide is a beta-emitting isotope.

6. The immunoconjugate of claim 5, wherein the beta-emitting isotope is $^{186}$Rh, $^{188}$Rh, $^{90}$Y, $^{131}$I, or $^{67}$Cu.

7. The immunoconjugate of claim 3, wherein the cytotoxic radionuclide is emitting Auger and low energy electron.

8. The immunoconjugate of claim 7, wherein the Auger and low energy electron emitting isotope is $^{125}$I, $^{123}$I or $^{77}$Br.

* * * * *